US011969371B2

(12) United States Patent
Binmoeller et al.

(10) Patent No.: US 11,969,371 B2
(45) Date of Patent: Apr. 30, 2024

(54) DUODENAL GASTROINTESTINAL DEVICES AND RELATED TREATMENT METHODS

(71) Applicant: Endosphere, Inc., Columbus, OH (US)

(72) Inventors: Kenneth F. Binmoeller, Rancho Santa Fe, CA (US); James T. McKinley, Redwood City, CA (US); Fiona M. Sander, Los Altos Hills, CA (US); John P. Lunsford, San Carlos, CA (US); Hoang G. M. Phan, Fremont, CA (US); Christopher Thorne, Columbus, OH (US)

(73) Assignee: Endosphere, Inc., Columbus, OH (US)

(*) Notice: Subject to any disclaimer, the term of this patent is extended or adjusted under 35 U.S.C. 154(b) by 41 days.

(21) Appl. No.: 17/332,866

(22) Filed: May 27, 2021

(65) Prior Publication Data
US 2021/0386571 A1 Dec. 16, 2021

Related U.S. Application Data

(63) Continuation of application No. 15/231,642, filed on Aug. 8, 2016, now Pat. No. 11,020,259, which is a continuation of application No. 13/666,919, filed on Nov. 1, 2012, now abandoned.

(60) Provisional application No. 61/699,172, filed on Sep. 10, 2012, provisional application No. 61/647,396, filed on May 15, 2012, provisional application No. 61/554,429, filed on Nov. 1, 2011.

(51) Int. Cl.
*A61F 5/00* (2006.01)

(52) U.S. Cl.
CPC .......... *A61F 5/0076* (2013.01); *A61F 5/0079* (2013.01)

(58) Field of Classification Search
CPC .............................. A61F 5/0076; A61F 5/0079
See application file for complete search history.

(56) References Cited

U.S. PATENT DOCUMENTS

| | | | | |
|---|---|---|---|---|
| 3,312,215 A | * | 4/1967 | Silber | A61M 3/0279 604/104 |
| 3,811,423 A | * | 5/1974 | Dickinson, III | A61D 17/002 128/830 |
| 4,878,905 A | * | 11/1989 | Blass | A61F 5/0036 604/285 |
| 7,931,693 B2 | * | 4/2011 | Binmoeller | A61F 5/0079 606/191 |
| 9,060,835 B2 | * | 6/2015 | Binmoeller | A61F 5/0036 |
| 2005/0277975 A1 | * | 12/2005 | Saadat | A61B 17/0218 606/191 |
| 2008/0065168 A1 | * | 3/2008 | Bitton | A61N 1/36007 607/40 |

(Continued)

*Primary Examiner* — Phong Son H Dang
(74) *Attorney, Agent, or Firm* — Erickson Law Group, PC

(57) ABSTRACT

An intragastric device includes an elongated member having a proximal end and a distal end and an anchor connected to the elongated member. The anchor includes a stem, a first arch and a second arch, and a curvilinear element. The stem includes a proximal end and a distal end. The distal end of the stem is attached to the proximal end of the elongated member. Each arch has first and second ends and a proximal peak therebetween. The first end of each arch is attached to the proximal end of the stem, and the second end of each arch extends radially away from the stem. The curvilinear element connects the second end of the first arch to the second end of the second arch.

16 Claims, 68 Drawing Sheets

FIG. 35B

(56) References Cited

U.S. PATENT DOCUMENTS

| | | | |
|---|---|---|---|
| 2011/0307075 A1* | 12/2011 | Sharma | A61F 5/0013 623/23.65 |
| 2012/0004676 A1* | 1/2012 | Vargas | A61F 5/0076 606/153 |
| 2012/0179086 A1* | 7/2012 | Shank | A61F 2/04 604/8 |
| 2015/0094753 A1* | 4/2015 | Dominguez | A61F 5/0086 606/198 |

* cited by examiner

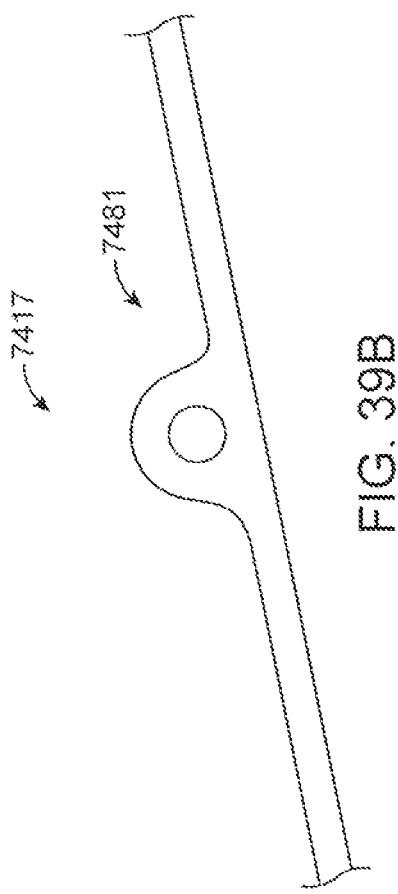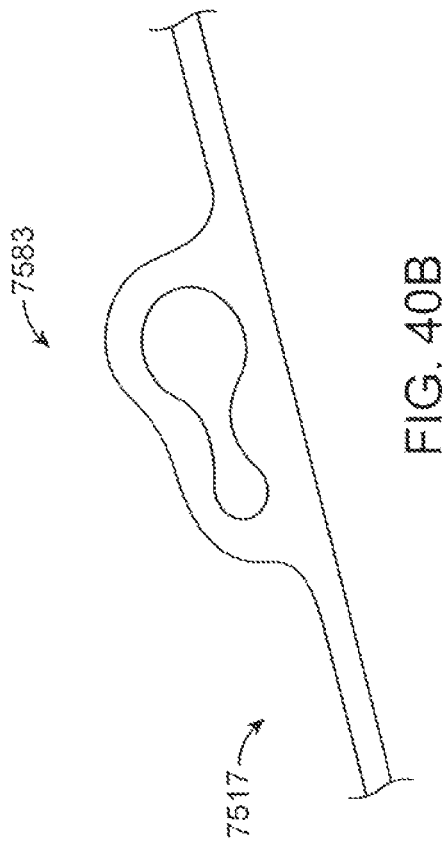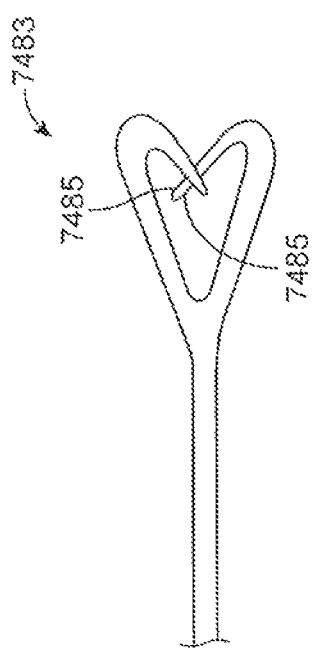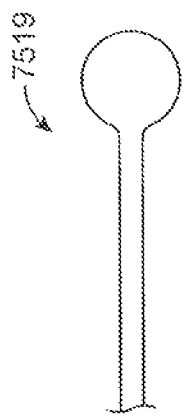
FIG. 39A
FIG. 39B
FIG. 40A
FIG. 40B

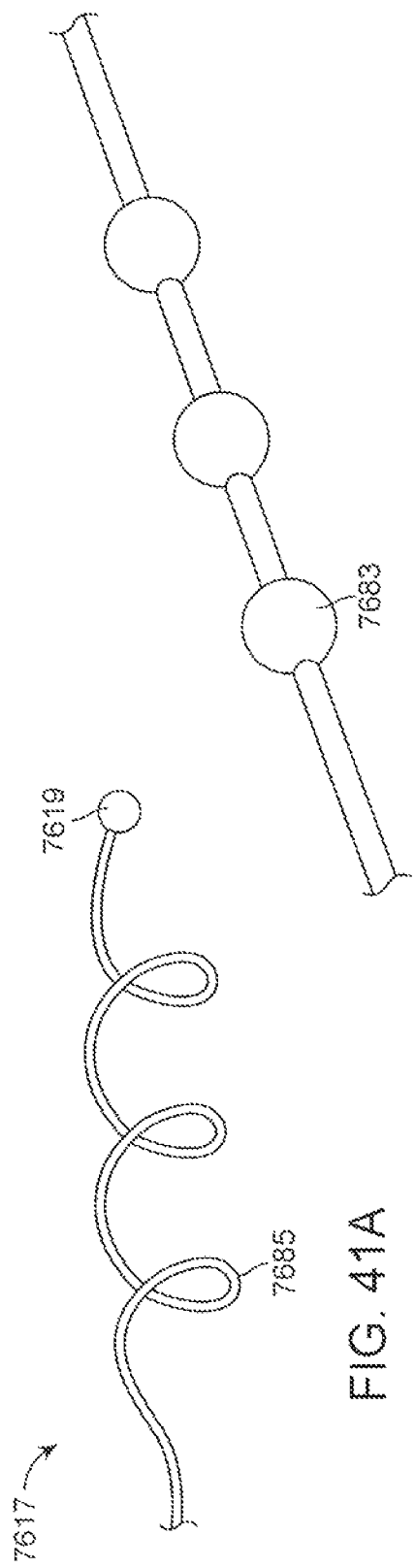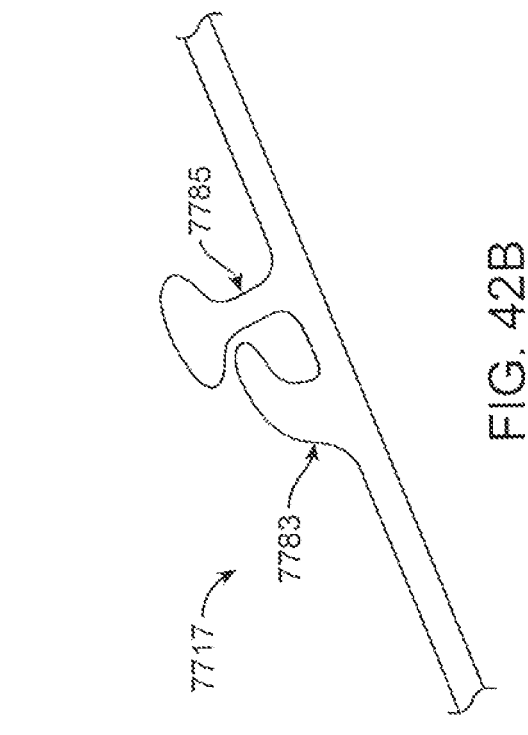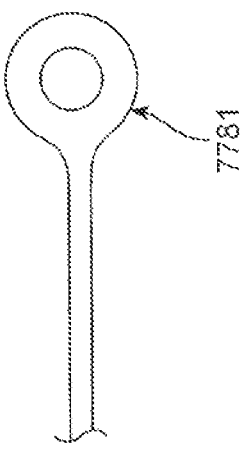
FIG. 41A
FIG. 41B
FIG. 42A
FIG. 42B

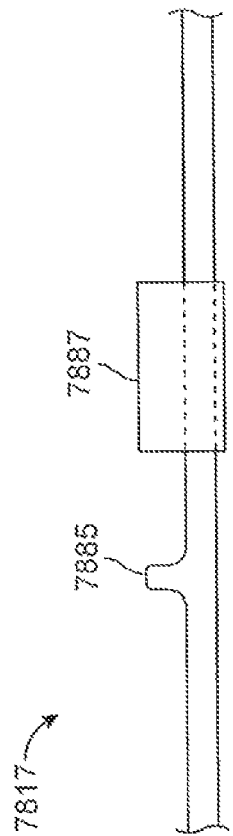
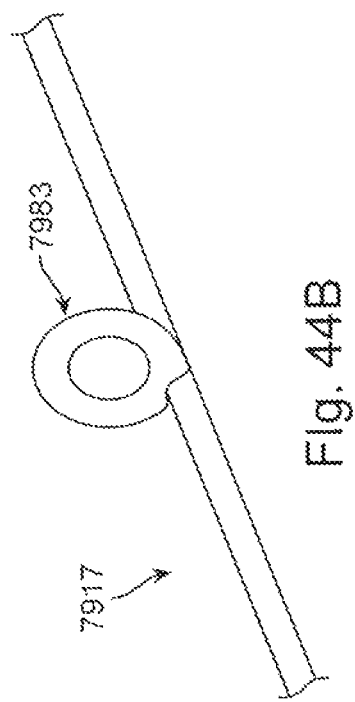
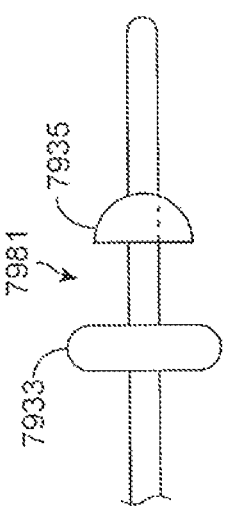

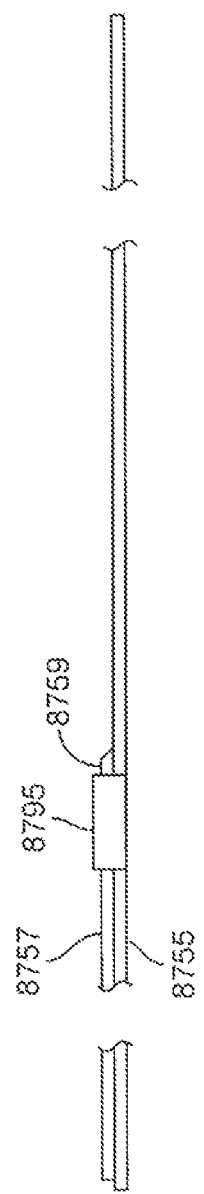

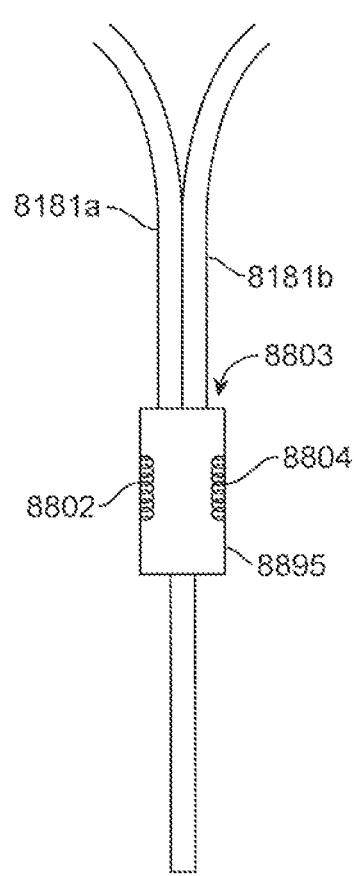
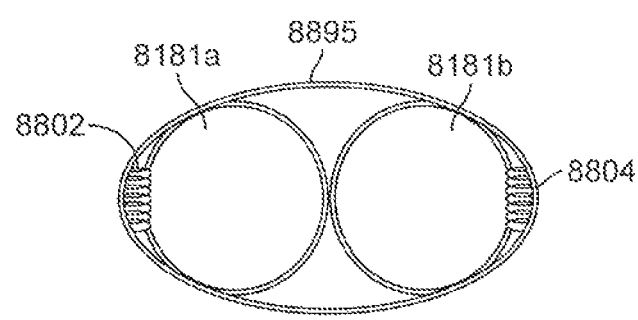
FIG. 53B
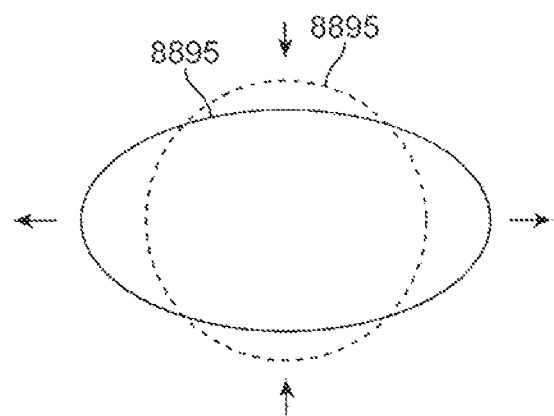
FIG. 53C
FIG. 53A

DUODENAL GASTROINTESTINAL DEVICES AND RELATED TREATMENT METHODS

CROSS REFERENCE TO RELATED APPLICATIONS

This application claims priority as a continuation of U.S. patent application Ser. No. 15/231,642, filed Aug. 8, 2016 which claims priority as a continuation of U.S. patent application Ser. No. 13/666,919, filed Nov. 1, 2012, titled "DUODENAL GASTROINTESTINAL DEVICES AND RELATED TREATMENT METHODS," now U.S. Patent Application Publication No. 2013-0109912, which claims priority to the following provisional patent applications: U.S. Provisional Patent Application No. 61/554,429, filed Nov. 1, 2011, titled "DUODENAL GASTROINTESTINAL DEVICES AND RELATED TREATMENT METHODS;" U.S. Provisional Patent Application No. 61/647,396, filed May 15, 2012, titled "DUODENAL GASTROINTESTINAL DEVICES AND RELATED TREATMENT METHODS;" and U.S. Provisional Patent Application No. 61/699,172, filed Sep. 10, 2012, titled "DUODENAL GASTROINTESTINAL DEVICES AND RELATED TREATMENT METHODS."

INCORPORATION BY REFERENCE

All publications, patents and patent applications mentioned in this specification are herein incorporated by reference to the same extent as if each individual publication, patent or patent application was specifically and individually indicated to be incorporated by reference.

FIELD

The invention is in the field of medical devices that reside within a lumen of the gastrointestinal tract and provide a platform for medical applications. More particularly, embodiments of the invention stabilize at a luminal residence site by virtue of their physical conformation.

BACKGROUND

Obesity, defined as a body mass index (BMI) of greater than 30, is a major health concern in the United States and other countries; it has been estimated that one in three Americans and more than 300 million people world-wide are obese. Complications of obesity include many serious and life-threatening diseases including hypertension, diabetes, coronary artery disease, stroke, congestive heart failure, pulmonary insufficiency, multiple orthopedic problems, various cancers and a markedly decreased life expectancy. Intentional weight loss, however, can improve many of these medical complications associated with obesity.

While weight loss can improve many of the medical complications associated with obesity, its management as a health concern has proven troublesome. A variety of approaches including dietary methods, psychotherapy, behavior modification, and pharmacotherapy have each met with some success but as a whole failed to effectively control the rapid growth in the incidence and severity of obesity seen in the United States. The severity of problems associated with obesity also has led to the development of several drastic surgical procedures. One such procedure physically reduces the size of the stomach so that a person cannot consume as much food as was previously possible. These stomach reduction surgeries had limited early success, but now it is known that the stomach can stretch back to a larger volume over time, limiting the achievement of sustained weight loss in many individuals. Another drastic surgical procedure induces the malabsorption of food by reducing the absorptive surface of the gastrointestinal (GI) tract, generally via by-passing portions of the small intestine. This gastric by-pass procedure further has been combined with stomach reduction surgery. While these described surgical procedures can be effective to induce a reduction in food intake and/or overall weight loss in some, the surgical procedures are highly invasive and cause undue pain and discomfort. Further, the described procedures may result in numerous life-threatening postoperative complications. These surgical procedures are also expensive, difficult to reverse, and place a large burden on the national health care system.

Non-surgical approaches for the treatment of obesity also have been developed. For example, one non-surgical endoscopic approach to treating obesity includes the placement of a gastric balloon within the stomach. The gastric balloon fills a portion of the stomach, providing the patient with a feeling of fullness, thereby reducing food intake. This approach has yet to be convincingly shown to be successful, and a number of problems are associated with the gastric balloon device, however, including poor patient tolerance and complications due to rupture and/or migration of the balloon. Other non-surgical devices designed to induce weight loss limit the absorption of nutrients in the small intestine by funneling food from the stomach into a tube found within the small intestine so that the food is not fully digested or absorbed within the small intestine. While this type of device may be somewhat effective at limiting the absorption of consumed food, there is still room for a variety of improvements in non-surgical devices designed to induce weight loss and/or a reduction in food intake.

An understanding of biological events that contribute to the creation of satiety signals provides an opportunity to develop "smart" nonsurgical devices that can trigger such events. The amount of food that individuals consume is largely dependent on biological signals between the gut and the brain. Specifically, hormonal signals from the gut to the brain are correlated with both the onset and cessation of food intake. While increased levels of hormones such as ghrelin, motilin and agouti-related peptide are involved in the promotion of appetite and the onset of food intake, increased levels of a number of other hormones are involved in the cessation of food intake.

Various biologic events contribute to the physiologic cessation of food intake. Generally, as a meal is consumed, the ingested food and by-products of digestion interact with an array of receptors along the GI tract to create satiety signals. Satiety signals communicate to the brain that an adequate amount of food has been consumed and that an organism should stop eating. Specifically, GI tract chemoreceptors respond to products of digestion (such as sugars, fatty acids, amino acids and peptides) while stretch receptors in the stomach and proximal small intestine respond to the physical presence of consumed foods. Chemoreceptors respond to the products of digestion by causing the release of hormones or other molecular signals. These released hormones and/or other molecular signals can stimulate nerve fibers to send satiety signals to the brain. The arrival of these signals in the brain can trigger a variety of neural pathways that can reduce food intake. The released hormones and/or other molecular signals can also travel to the brain themselves to help create signals of satiety. Mechanoreceptors generally send satiety signals to the brain through stimulation of nerve fibers in the periphery that signal the brain. The present invention provides methods and devices that help to reduce food intake by providing non-surgical devices and methods that trigger the aforementioned biological events that contribute to the creation of satiety signals.

SUMMARY OF THE DISCLOSURE

Described herein are intragastric devices.

In general, in one embodiment, an intragastric device includes an elongated member having a proximal end and a distal end and an anchor connected to the elongated member. The anchor includes a stem, a first arch and a second arch, and a curvilinear element. The stem includes a proximal end and a distal end. The distal end of the stem is attached to the proximal end of the elongated member. Each arch has first and second ends and a proximal peak therebetween. The first end of each arch is attached to the proximal end of the stem, and the second end of each arch extends radially away from the stem. The curvilinear element connects the second end of the first arch to the second end of the second arch.

This and other embodiments can include one or more of the following features. The stem, the first arch, the second arch, and the curvilinear element can be formed from a single piece of wire. The elongated member can be formed from the same single piece of wire. The curvilinear element can include at least one coil that loops around and substantially perpendicular to the stem. The coil can form at least one complete loop around the stem. The distance between the second end of the first arch and the second end of the second arch can be greater than the diameter of the coil. The second end of the first arch can curve in the same clockwise or counterclockwise direction as the second end of the second arch. The first arch and second arch can extend in substantially opposite radial directions. The curvilinear element can include a pull loop extending proximal to the proximal end of the stem between the first and second arches. The pull loop can be configured such that, when the pull loop is moved proximally away from the stem, the curvature of the first arch and the second arch are reduced. The curvilinear element can include at least one counterarch, and the counterarch can have a distal peak. In use within the gastrointestinal tract, the diameter of the anchor can be larger than an opening through which the elongated member passes. The opening can be a pylorus. The arches and curvilinear element can be configured to be unwound to form a straightened anchor for delivery or removal of the anchor from the gastrointestinal tract. The straightened anchor can include two substantially parallel and straight wires for delivery or removal. The device can further include a fastening element configured to fasten at least one portion of the anchor to another portion of the anchor to hold the shape of the anchor during use in the gastrointestinal tract.

In general, in one embodiment, a method of anchoring a treatment device in the stomach includes: advancing the treatment device through the pylorus and into position within the gastrointestinal tract; positioning an anchor connected to the device in the stomach in a stowed configuration; and expanding the anchor from the stowed configuration into a deployed configuration. The deployed configuration has a stem with a first arch and a second arch radially extending therefrom. The anchor in the deployed configuration has a diameter that is larger than the diameter of the pylorus.

This and other embodiments can include one or more of the following features. In the stowed configuration, then anchor can include two substantially parallel and straight wires, and the substantially parallel and straight wires can form the first and second arches in the deployed configuration. The method can further include pulling proximally on a portion of the anchor in the deployed configuration to collapse the anchor back to the stowed configuration. The portion of the anchor can be a pull loop connected to the arches. The anchor can further include a curvilinear element connecting the first and second arches together. Pulling proximally on the pull loop can cause the curvilinear element to move proximally past the first and second arches and pull the first and second arches substantially straight. The method can further include locking the anchor in the deployed configuration with a fastening element.

In an alternative to the embodiments described above, an anchor may include a single arch. In another alternative embodiment, the anchor may include single or multiple coils or loops of wire without any arches.

Any of the embodiments described above can include one or more of the following features.

The device can include a conformationally-stabilized spine. Flow reduction elements can surround the elongated member. The flow reduction elements can be formed of an expandable sleeve. The flow reduction elements and/or the elongated member can include bioactive materials therein. The distal end of the elongated member can terminate near the duodenojejunal junction. The anchors can include a fastener to lock two portions of the anchor together, such as a cinching mechanism, a ball and spring fastener, and eyelet and double barbed fastener, a ball and doubled-lumen eyelet fastener, a helical and multi-ball fastener, an eyelet and post/tab fastener, a sleeve fastener, or a multi-tabbed and eyelet fastener. The elongated member can be a floppy cord or tube. The anchor or elongated member can have shape lock features. The ends of the device can be bulbous or coiled. The stem can be formed of two wires that are joined together. The joint between the two wires can be a sleeve welded to each wire without welding between the two wires. The joint can include welding between the two wires. The anchor can be asymmetric with respect to the stem. The anchor can have a "figure 8" shape. The anchor can be formed of a single wire having a break therein. The break can be closed with a fastener. The device can include a secondary anchor for use in the duodenal bulb. The device can include a pusher thereon configured to provide a location for contact during delivery or removal of the device.

BRIEF DESCRIPTION OF THE DRAWINGS

FIG. 16A depicts a device with a relatively long separation between ends and a relatively large end-end cross over dimension. FIG. 16B depicts a device with a relatively short separation between ends and a relatively small end-end cross over dimension.

FIGS. 39A and 39B show another embodiment of a fastener for locking a proximal anchor.

FIGS. 40A and 40B show another embodiment of a fastener for locking a proximal anchor.

FIGS. 41A and 41B show another embodiment of a fastener for locking a proximal anchor.

FIGS. 42A and 42B show another embodiment of a fastener for locking a proximal anchor.

FIGS. 43A and 43B show another embodiment of a fastener for locking a proximal anchor.

FIGS. 44A and 44B show another embodiment of a fastener for locking a proximal anchor.

FIG. 51 shows the stem portion of an exemplary proximal anchor.

FIGS. 53A, 53B and 53C show an exemplary sleeve and welding configuration for a stem of a proximal anchor.

DETAILED DESCRIPTION

Embodiments of the Device In Situ

Figure 1:
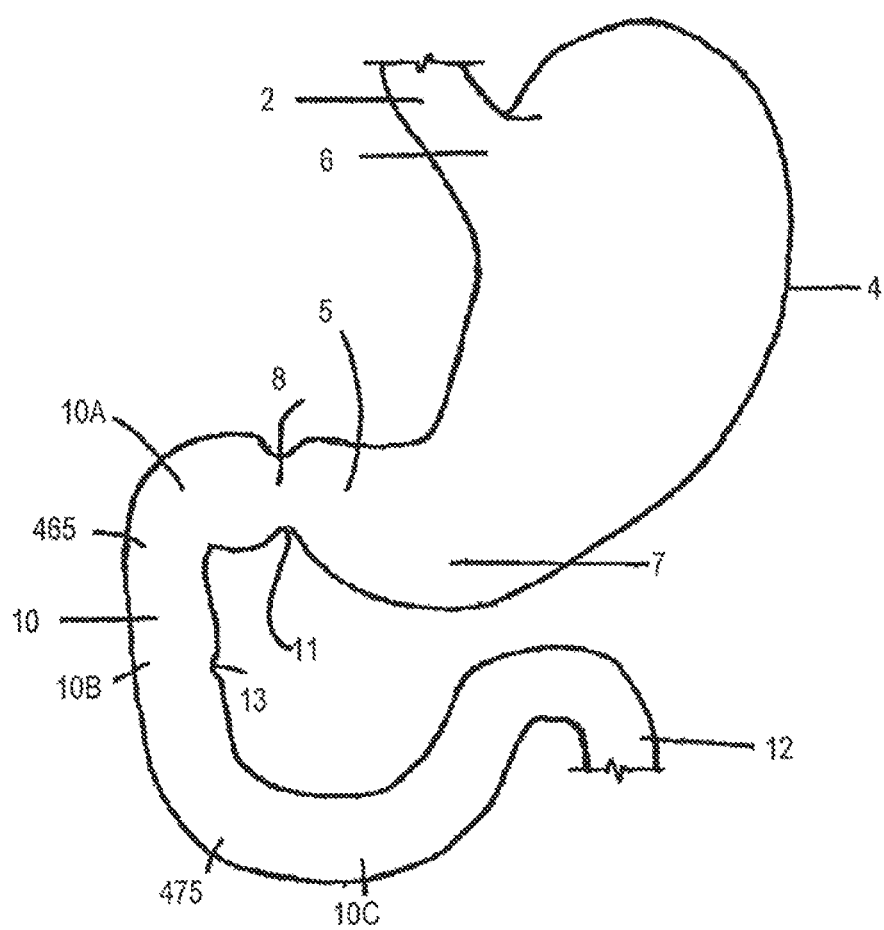
FIG. 1 is a general drawing of the stomach and duodenum of the small intestine.

FIG. 1 provides a view of the human gastrointestinal tract, including the stomach 4 and duodenum of the small intestine 10. Important features are the esophagus 2, stomach 4, antrum 7, pylorus 8, pyloric valve 11, duodenum 10, jejunum 12 and ampulla of Vater (or hepatopancreatic ampulla) 13, which is formed by the union of the pancreatic duct and the common bile duct. Functionally, the esophagus 2 begins at the nose or mouth at its superior end and ends at the stomach 4 at its inferior end. The stomach 4 encloses a chamber which is characterized, in part, by the esophageal-gastric juncture 6 (an opening for the esophagus 2) and the antrum-pyloric juncture 5 (a passageway between the antrum 7 through the pylorus 8 to the duodenum 10 of the small intestine). The pylorus 8 controls the discharge of contents of the stomach 4 through a sphincter muscle, the pyloric valve 11, which allows the pylorus 8 to open wide enough to pass sufficiently-digested stomach contents (i.e., objects of about one cubic centimeter or less). These gastric contents, after passing into the duodenum 10, continue into the jejunum 12 and on into the ileum (not shown). The duodenum 10, jejunum 12 and ileum make up what is known as the small intestine. However these individual portions of the alimentary canal are sometimes individually referred to as the small intestine. In the context of this invention the small intestine can refer to all or part of the duodenum, jejunum and/or ileum. The ampulla of Vater 13, which provides bile and pancreatic fluids that aid in digestion, is shown as a small protrusion on the medial wall of the duodenum 10.

Embodiments of the inventive device include various forms that provide stability in a residence site in the gastrointestinal tract, particularly the duodenum. Some embodiments of the device, which may be synonymously referred to as an intestinal insert, are stabilized in the intestine by way of an anchoring member that resides in the stomach and is too large to be swept through the pylorus. In other embodiments, stabilizing features in the intestine may include expanded portions of the device in the duodenal bulb, which is larger than the more distal portion of the duodenum, and which thereby effectively prevents distal movement (as in FIGS. 89-90, for example).

Some embodiments of the device and associated methods of using the device are directed toward reducing the rate of food transit through the intestine by physical mechanisms of intervening in the rate of food transit. In other aspects, embodiments of the invention act by eliciting satiety signals by way of physiological mechanisms, or, alternatively, by directly providing satiety signals through bioactive materials or agents, or by neuronal stimulation, thereby reducing food intake behaviorally. Some embodiments of the device are directed toward medical purposes broader than satiety and digestive physiology alone, although the satiety and food consumption functionalities of embodiments of the device and method will be described herein in greater detail. As an example of non-obesity or satiety-inducing medical use, some embodiments of the devise may be used as an eluting source for bioactive agents, and as such any medically appropriate drug could be delivered by such a device. In some aspects, embodiments of the device may contribute to slowing food transit and/or reducing food intake by the satiety signals generated by the intestine in direct response to the mere physical presence of the device. Such signals could, for example, be mediated by stretch-responsive neurons or mechanoreceptors in the intestinal wall. In other embodiments, satiety signals could be mediated by hormones that are responsive to physical presence of material in the intestine, or which are secondarily responsive to mechano-receptors. In other embodiments, the slowing of food or the increased residency time, and the consequent change in the chemical environment of the intestine, may elicit responses from chemoreceptors residing in the intestine to signal either neurally or hormonally in such a way that has a net effect of signaling satiety.

In still other embodiments of the invention, the device may convey bioactive material or agents that are released over time within the intestine, the bioactive agents conveying a net signal of satiety. In some embodiments, the bioactive agents with a net satiety signaling effect are passively released from sites such as coatings, depots, or reservoirs within the device. Bioactive materials or agents have been described in detail above, but briefly and in broad aspect may include any of hormones, drugs, or cells. In some embodiments, bioactive agents may be held in osmotic pumps and released by osmotic drive. Release mechanisms such as osmotic pumps provide a level of control and predictability to bioactive agent release, but the mechanism remains relatively passive and without means of intervention. Other embodiments of the invention, however, may include more active mechanisms for bioactive agents release or delivery, as could be provided by electrically driven pumps, or by piezoelectric elements that allow or promote the release stored bioactive agents in response to applied current. Such devices may include power storage elements, or may be provided power by external sources by wired or wireless approaches.

In still other embodiments of the invention, the device may include electrodes or conductive elements that provide electrical stimulation to nerves in the intestine, such resulting neural activity contributing to a net effect of signaling satiety to the brain. In some embodiments, satiety-related neuronal activity may further be mediated by endocrine mechanisms. As in embodiments of the invention with powered mechanisms for bioactive agent release, embodiments with electrical capability may include power storage devices, or be enabled to receive energy conveyed from external sources.

In other aspects of the invention, embodiments of the inserted device, with or without an anchor, may provide a platform for bioactive agent delivery, neural stimulus delivery, or radiation therapy delivery, for medical purposes more broad than inducing satiety, or intervening in food transit. For the delivery of some bioactive agents, there may be considerable advantage associated with local delivery of an agent to an intestinal site. Such advantages may include localization of dosing, lack of exposure to stomach acid as occurs in oral delivery or diminished exposure to the metabolic machinery of the liver and kidney that i. v. drug delivery, or any form of systemic delivery faces. Further, embodiments of the device may accommodate multiple drugs; in some embodiments the release of such multiple drugs may be independently controlled.

Digestive System Context of Invention

The description now addresses the digestive system, the digestive process, and aspects of the endocrinology and neurophysiology of satiety as they relate to embodiments of the invention. The adult duodenum is about 20-25 cm long and is the shortest, widest, and most predictably placed part of the small intestine. The duodenum forms an elongated C-shaped configuration that lies between the level of the first and third lumbar vertebrae in the supine position. Susan Standring (ed.), Gray's Anatomy, 39$^{th}$ Ed., 1163-64 (2005), provides a standard reference. Returning to FIG. 1 for reference and further detail of aspects of the digestive system, the first part of the duodenum, often referred to as the duodenal bulb 10a, is about 5 cm long and starts as a continuation of the duodenal end of the pylorus 8. This first part of the duodenum passes superiorly, posteriorly and laterally for 5 cm before curving sharply inferiorly into the superior duodenal flexure 465, which marks the end of the first part of the duodenum. The second part of the duodenum, often called the vertical duodenum 10b, is about 8-10 cm long. It starts at the superior duodenal flexure 465 and runs inferiorly in a gentle curve towards the third lumbar vertebral body. Here, it turns sharply medially into the inferior duodenal flexure 475 which marks its junction with the third part of the duodenum. The third part of the duodenum, often called the horizontal duodenum 10c, starts at the inferior duodenal flexure and is about 10 cm long. It runs from the right side of the lower border of the third lumbar vertebra, angled slightly superiorly, across to the left and ends in continuity with the fourth part of the duodenum in front of the abdominal aorta. The fourth part of the duodenum is about 2.5 cm in length; it starts just to the left of the aorta and runs superiorly and laterally to the level of the upper border of the second lumbar vertebra. It then turns antero-inferiorly at the duodenojejunal flexure and is continuous with the jejunum. Some embodiments of the present invention take advantage of this predictable configuration of the small intestine to provide duodenal/small intestinal implants that do not require anchoring within the pylorus or stomach, as described more fully below.

The digestive process starts when consumed foods are mixed with saliva and enzymes in the mouth. Once food is swallowed, digestion continues in the esophagus and in the stomach, where the food is combined with acids and additional enzymes to liquefy it. The food resides in the stomach for a time and then passes into the duodenum of the small intestine to be intermixed with bile and pancreatic juice. Mixture of the consumed food with bile and pancreatic juice makes the nutrients contained therein available for absorption by the villi and microvilli of the small intestine and by other absorptive organs of the body.

Robert C. Ritter, author of "Gastrointestinal mechanisms of satiation for food", published by Physiology & Behavior 81 (2004) 249-273, summarizes our understanding of the various means the gastrointestinal tract uses to control appetite. He states that the role of the stomach in satiation is to sense the volume of ingesta arriving from a meal and to produce a variety of signaling substances that may be involved in satiation. It is, however, the small intestine specifically that receives these signals. Further, it is the intestine that responds to the energy density of ingesta, limiting further gastric emptying and signally satiety when adequate calories have passed. Through analysis of the location of afferent nerves (p. 255), Ritter shows that vagal nerve afferents are most concentrated in the duodenum and least concentrated more distally in the ileum. This early concentration of afferents will moderate appetite early in the eating process. The timeliness of the response to nutrient intake has been further demonstrated by others in a variety of mammals including monkeys, rats and humans. It is clear that the reduction in food intake begins within minutes of the start of intake and that this reduction is not therefore a response to postabsorptive or systematic metabolic effects. These passages of Ritter are specifically incorporated herein by reference as relates to the positioning of the devices described herein or for the placement and size of flow reduction elements of embodiments of the present invention.

The presence of partially digested food within the stomach and small intestine initiates a cascade of biological signals that create satiety signals principally emanating from the proximal small intestine that contribute to the cessation of food intake. One such satiety signal is initiated by the release of cholecystokinin (CCK). Cells of the small intestine release CCK in response to the presence of digested foods, and in particular, in response to dietary fat, fatty acids, small peptides, and amino acids. Elevated levels of CCK reduce meal size and duration and may do so through a number of different mechanisms. For example, CCK may act on CCK-A receptors in the liver and within the central nervous system to induce satiety signals. CCK stimulates vagal afferent fibers in both the liver and the pylorus that project to the nucleus tractus solitarius, an area of the brain that communicates with the hypothalamus to centrally regulate food intake and feeding behavior. CCK also stimulates the release of enzymes from the pancreas and gall bladder and inhibits gastric emptying. Because CCK is a potent inhibitor of gastric emptying, some of its effects on limiting food intake may be mediated by the retention of food in the stomach.

Cells of the small intestine (particularly L cells) also release glucagon-like peptide 1 (GLP-1) and oxyntomodulin (OXM) in response to nutrient signals of digestion. Elevated levels of GLP-1 and OXM are associated with satiety signals and the cessation of food intake. These hormones may signal satiety by activating receptors on afferent vagal nerves in the liver and/or the GI tract and/or by inhibiting gastric emptying.

Pancreatic peptide (PP) is released in proportion to the number of calories ingested, and in response to gastric distension. Elevated levels of PP have been shown to reduce food intake and body weight. PP may exert some of its anorectic effects via vagal afferent pathways to the brainstem, as well as through more local effects, such as by suppression of gastric ghrelin production.

Peptide $YY_{3-36}$ ($PYY_{3-36}$) is another biological signal whose peripheral release may be correlated with reduced food intake and/or the cessation of eating. Specifically, low levels of $PYY_{3-36}$ have been correlated with obesity while its administration decreases caloric intake and subjective hunger scores. Intravenous administration of $PYY_{3-36}$ may reduce food intake through its effects of suppressing ghrelin expression, delaying gastric emptying, delaying various secretion from the pancreas and stomach and increasing the absorption of fluids and electrolytes from the ileum after a meal.

Insulin and leptin are two additional biological signals that regulate satiety and eating behavior. Through parasympathetic innervation, beta cells of the endocrine pancreas release insulin in response to circulating nutrients such as glucose and amino acids, and in response to the presence of GLP-1 and gastric inhibitory peptide (GIP). Insulin stimulates leptin production from adipose tissue via increased glucose metabolism. Increased insulin levels in the brain leads to a reduction in food intake. Elevated leptin levels also decrease food intake and induce weight loss. Insulin and leptin have also been implicated in the regulation of energy expenditure since their administration induces greater weight loss than can be explained by reduction in food intake alone. Both insulin and leptin act within the central nervous system to inhibit food intake and to increase energy expenditure, most likely by activating the sympathetic nervous system. Insulin's effects to decrease food intake also involve interactions with several hypothalamic neuropeptides that are also involved in the regulation of feeding behavior such as, by way of example, NPY and melanocortin ligands.

Other hormones or biological signals that are involved in the suppression or inhibition of food intake include, by way of example, GIP (secreted from intestinal endocrine K cells after glucose administration or ingestion of high carbohydrate meals; enterostatin (produced in response to dietary fat; amylin (co-secreted with insulin from pancreatic beta cells); glucagon, gastrin-releasing peptide (GRP), somatostatin, neurotensin, bombesin, calcitonin, calcitonin gene-related peptide, neuromedin U (NMU), and ketones.

In relation to embodiments of the present invention, when the passage of partially digested food or chyme is partially impeded within the duodenum of the small intestine and the flow rate through this area is reduced (or to express the same phenomenon in another way, as residency time is increased), the emptying of the stomach and the duodenum will occur more slowly. This slowing, by itself, may create extended feelings of satiety and thus lead to a decrease in food intake (due to the longer retention time of food in the stomach). The slowing of the passage of food also provides more time for the partially digested food to interact with chemoreceptors, stretch receptors, and mechanoreceptors along the GI tract so that stimulation of satiety signals may be increased and/or prolonged, which may, in turn, lead to a reduction in food intake during an eating period and/or longer periods between food intake.

In addition to keeping partially-digested food within the small intestine for an extended period of time, the methods and devices of the present invention may also enhance and/or prolong the release of satiety signals by releasing signals into the small intestine themselves. For example, in some embodiments, the methods and devices of the present invention may release nutrient products of digestion to stimulate chemoreceptors to cause the release of hormones and/or other molecular signals that contribute to the creation of satiety signals. In another embodiment, the methods and devices of the present invention may exert a small amount of pressure on the walls of the GI tract to stimulate stretch (mechanoreceptors) to generate and send satiety signals to the brain. In another embodiment, the methods and devices of the present invention may release signals, such as, by way of example, nutrient by-products of digestion of food, to stimulate chemoreceptors as described above and may exert a small amount of pressure on the walls of the small intestine as described above to contribute to the generation of satiety signals.

Device with Flow Reduction Elements

Figure 2:
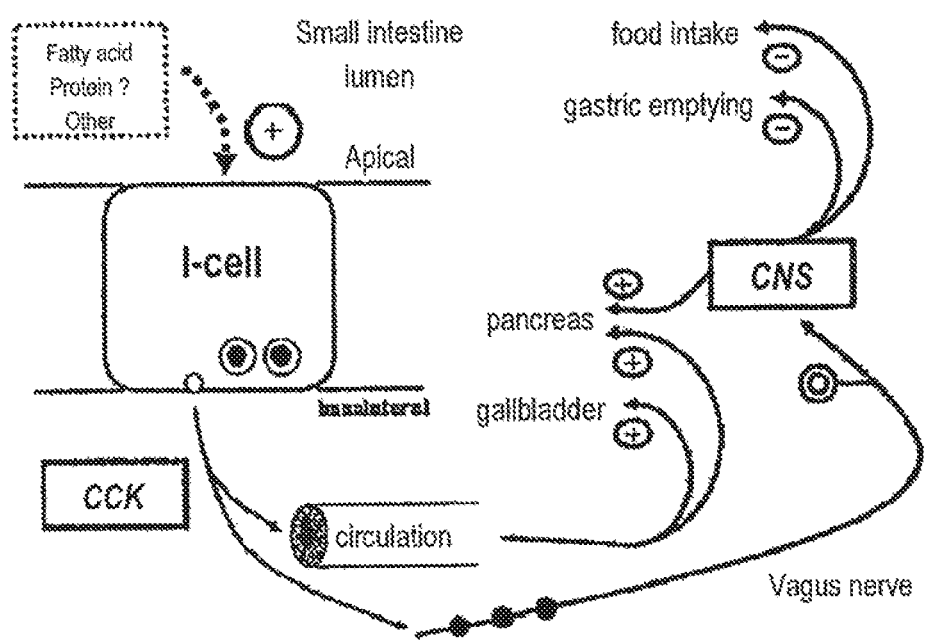
FIG. 2 depicts several exemplary mechanisms through which satiety signals may be generated.

FIG. 2 depicts several exemplary non-limiting mechanisms through which satiety signals may be generated. As shown FIG. 2, a by-product of digestion, such as a fatty acid or other protein, stimulates an L-cell of the small intestine to release CCK locally and into the circulation. CCK released locally may stimulate vagal afferent nerve fibers in the area to generate satiety signals to the central nervous system (CNS). CCK that enters the circulation may travel to the liver to stimulate vagal afferent nerve fibers in the liver to generate satiety signals to the CNS. CCK in the circulation may travel to the gall bladder and pancreas to upregulate the digestion-related activities of these organs. CCK in the circulation also may travel to the CNS itself to contribute to the creation of a satiety signal. Once satiety signals are received and integrated within the CNS, the CNS may trigger physiological effects that serve to contribute to a feeling of fullness and/or the cessation, slowing or reduction of food intake.

Figure 3:
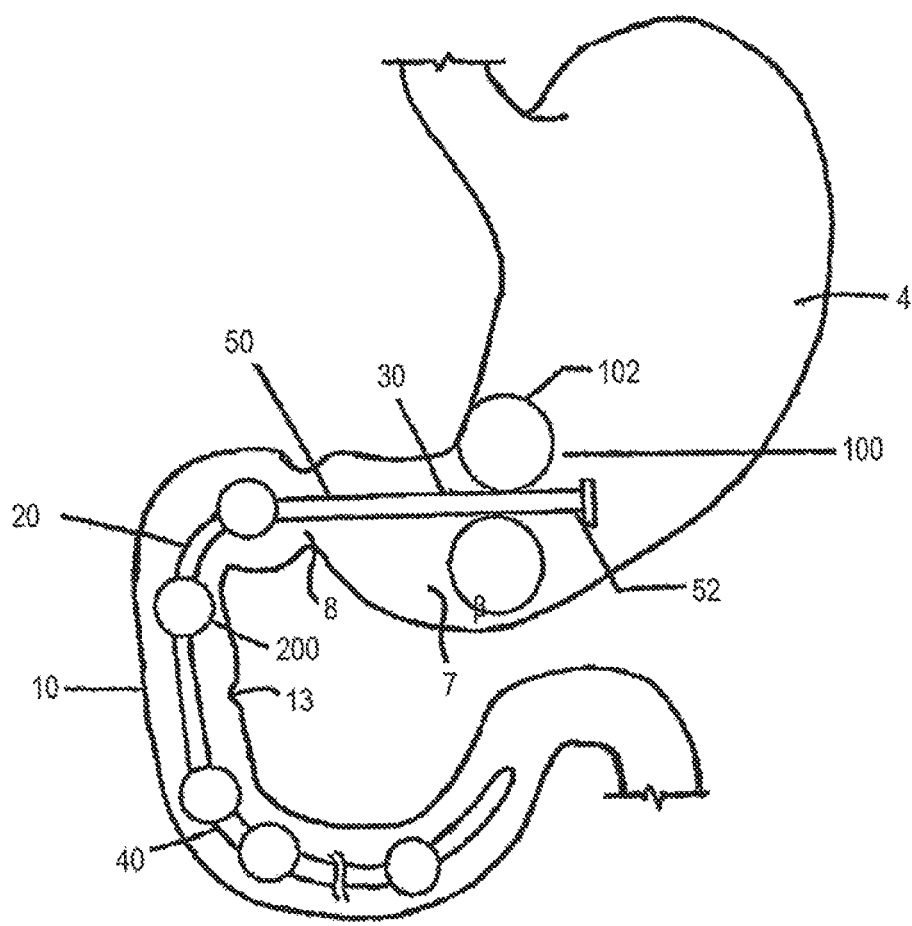
FIG. 3 is a perspective view of one embodiment of a duodenal/small intestinal insert in accordance with the present invention positioned inside the stomach and small intestine.

Turning now to embodiments of the invention, FIG. 3 shows an exemplary small intestinal insert 20 made in accordance with the present invention that may contribute to the creation of satiety signals. The insert 20 is positioned in the stomach 4 and small intestine 10. The insert 20 has a proximal portion 30 and a distal portion 40, and a central tube 50 that extends from the proximal portion 30 to the distal portion 40. One or more flow reduction elements 200 that are sized to fit within the small intestine 10 may be attached to the central tube 50. While not required, the portion of the central tube 50 near the ampulla of Vater 13 generally will not include a flow reduction element 200 so that the introduction of bile and pancreatic fluid into the small intestine is not impeded.

In some embodiments, the central tube or spine 50 has an anchoring member 100 near its proximal end 52, with the anchoring member 100 securing the proximal end 52 of the central tube 50 in the stomach. The anchoring member 100 is sized so that it will not pass through the pylorus 8. In this way, embodiments of the present invention including an anchoring member anchor the flow reduction elements 200 within the small intestine. In some embodiments, the anchoring member may be established by one or more inflatable balloons 102 that when inflated are larger than the pylorus 8. The inflatable balloons 102 may be deflated for delivery into the stomach and then inflated inside the stomach. The inflatable balloons 102 may also be deflated for later removal using endoscopic techniques.

Figure 16A:
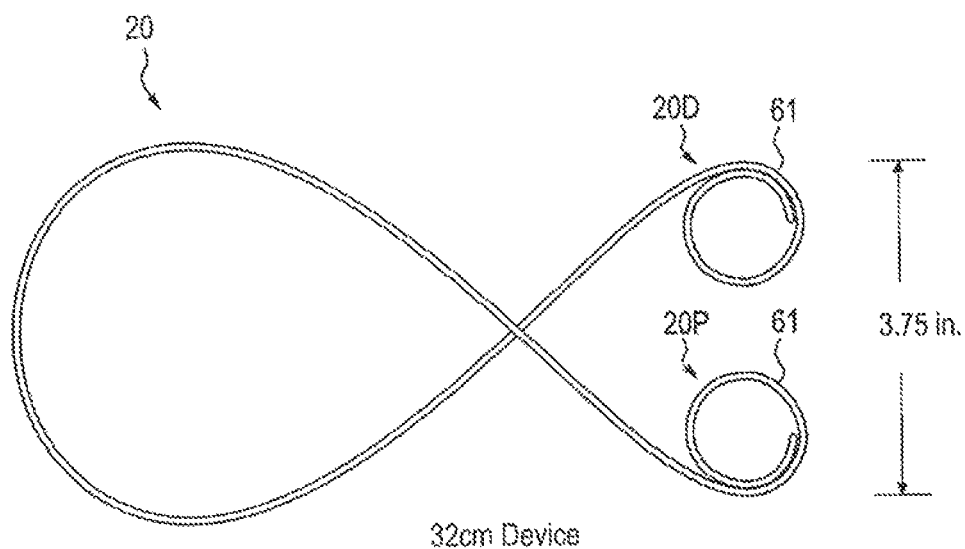
FIGS. 16A and 16B show two devices with a varying amount of end-end crossover.
Figure 16B:
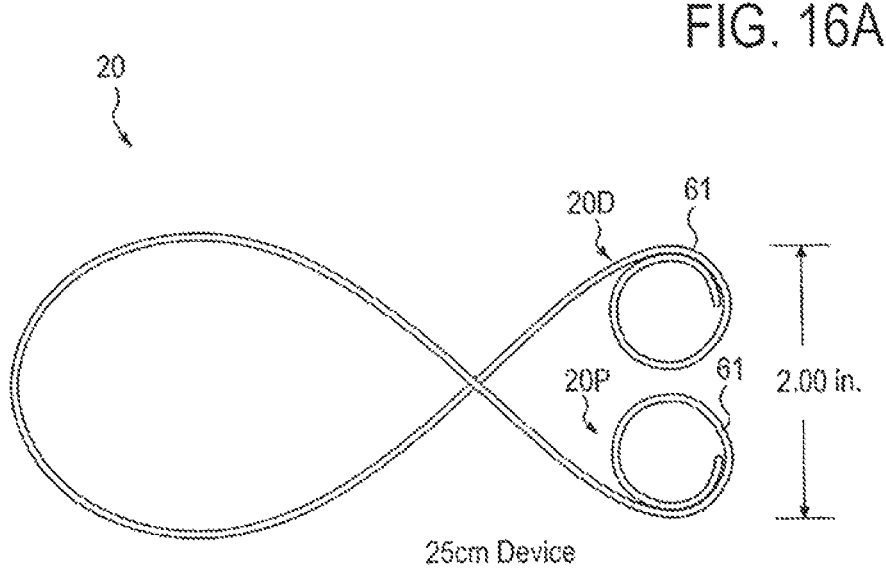

As will be described in further detail below, embodiments of flow reduction elements 200 may assume many configurations, and may vary further with regard to physical features such as composition, nature of the surface, and porosity of the bulk material. Some further exemplary embodiments of flow reduction elements 200 are depicted in FIGS. 16-25. In some embodiments, as depicted in FIG. 16, the central tube or member, also referred to as an elongated member, may, itself, be configured into a form that reduces chyme flow in the duodenum. A functional property that embodiments of flow reduction elements have in common is that they slow the transit of digesting food without blocking it, and within clinically appropriate guidelines. The process of slowing the transit rate may also have effects on the composition of the digesting food material, such as varying its biochemical profile with regard to the nutritional compounds being metabolized. Chemical receptors and nerves of the duodenum are sensitive to the biochemical profile of metabolites within the chyme, and participate in the coordination of physiology of digestion and satiety and hunger, accordingly. As such, by altering the flow rate and hence, the biochemical profile of chyme, embodiments of the inventive small intestinal insert contribute to the generation of signals associated with satiety. Flow reduction elements may further effect the composition of the digesting food material by the mixing action the flow reduction elements may provide.

Figure 4:
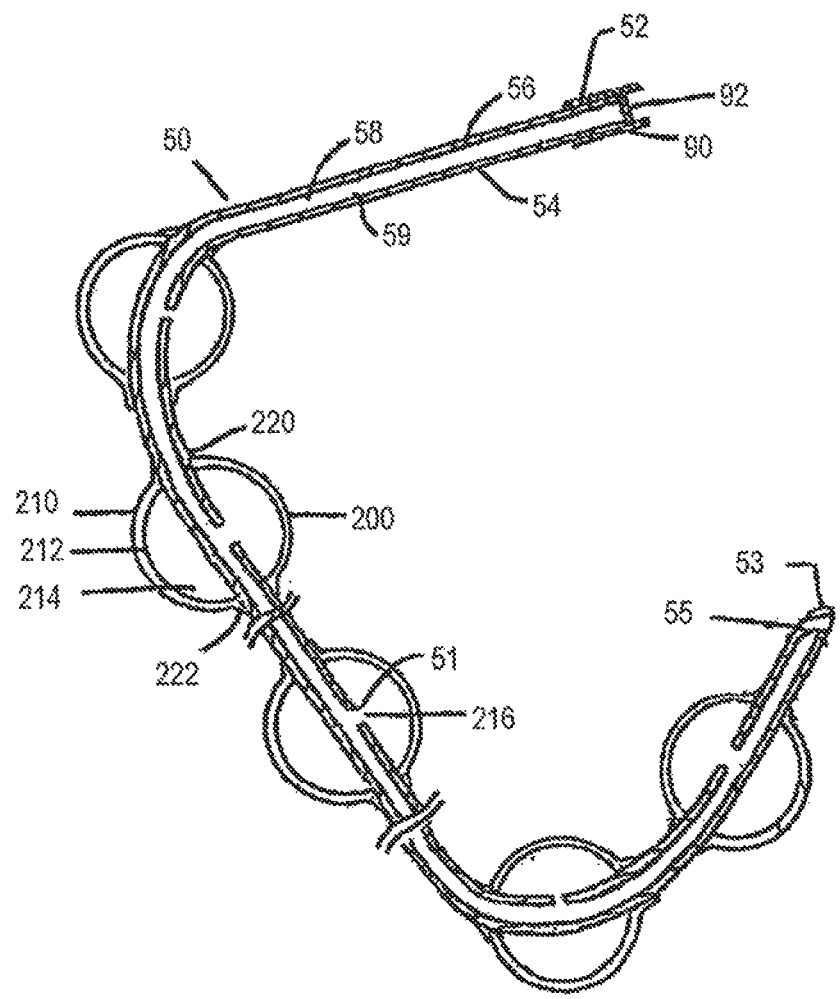
FIG. 4 is a partial section view of a central tube illustrating attached flow reduction elements and a central lumen.

FIG. 4 shows an embodiment of the invention with a central tube 50 that includes an outer wall 54 and an inner wall 56 that define an interior space 58. The interior space 58 forms an inner lumen 59 that may be continuous from the proximal end 52 of the central tube 50 to just short of the distal end 53 of the central tube 50. The distal end 53 of the central tube 50 is sealed at a point 55 so that fluid introduced into the central tube 50 does not leak out distally into the small intestine. In some embodiments a valve 90 may be located substantially at the proximal end of the inner lumen 59. The valve 90 may be a self-sealing valve that has a septum 92 that may be accessed by a needle or blunt tip tube for introduction of fluid into the inner lumen 59. The valve 90 also may be accessed so that the fluid inside the inner lumen 59 of the central tube 50 may be aspirated for removal. It is to be understood that the valve type is not limited to a septum type valve only, and that other types of mechanical valves may also be used in place of the septum valve described. Particular embodiments of the present invention are adapted to accept fluids in this manner so that the devices of the present invention may be implanted in a deflated configuration and later expanded into an inflated configuration.

As shown in FIG. 4 and as mentioned above, one or more flow reduction elements 200 may be attached to the central tube 50. In some embodiments the diameter of each flow reduction element 200 may be concentric with the axis of the central tube 50. In the embodiment depicted in FIG. 4, each flow reduction element 200 has an outer wall 210, an inner wall 212, and an inner space 214. At or near its proximally-oriented surface 220 and also at or near its distally-oriented surface 222, each flow reduction element 200 may be attached to the central tube 50 with the inner space 214 of the flow reduction element 200 in fluid communication with the lumen 59 of the central tube 50, such that the inner space 214 surrounds the outer wall 54 of the central tube 50. Each flow reduction element 200 may be attached to the central tube 50 by, for example, adhesives, heat bonding, mechanical restraint or other suitable methods.

As also depicted in FIG. 4, the central tube 50 may be formed with plural inlet/exit ports 216 that are located inside respective flow reduction elements 200. More specifically, each port 216 is formed completely through the central tube wall 51 to establish a pathway for fluid communication between the inner lumen 59 of the central tube 50 and the inner space 214 of the respective flow reduction elements 200. Consequently, the inner lumen 59 of the central tube 50 may be used to introduce fluid into the inner spaces 214 of the flow reduction elements 200 and to inflate the flow reduction elements 200 from a collapsed configuration, in which insertion and removal of the flow reduction elements 200 is facilitated, to an inflated configuration shown in FIG. 4, in which resistance to food passage is increased to induce satiety. Thus, as suggested earlier, the flow reduction element or elements 200 in this embodiment act as balloons that may be deflated and collapsed around the central tube 50 for introduction into the small intestine and then inflated to the desired diameter once in position.

Embodiments of the flow reduction elements may assume other forms, such as coils, ribs, fans, baffles, either peripherally-mounted or centrally-mounted, as well as sleeves, mesh cages or baskets. Embodiments such as these are described further, below, in the section entitled "Further exemplary embodiments of the invention", which also includes description of embodiments with biodegradable components, active biomaterial release mechanisms, and nerve stimulation features, and as depicted in FIGS. 15-31.

In some embodiments, individual flow reduction elements 200 of the present invention may be elastic balloons or inelastic balloons. When an elastic balloon material is used to establish a flow reduction element 200, the flow reduction element 200 inflates to a diameter that is dependent on the volume of fluid introduced into the inner space of the flow reduction element. This embodiment permits adjustment of the balloon size as determined by the physician. If the balloon is too small, for instance, additional fluid could be introduced to enlarge the balloon diameter. Alternatively, if the balloon is too large, additional fluid could be removed to shrink the balloon diameter. It is understood that an alternate embodiment consisting of an inelastic balloon that inflates to a diameter that is independent of a volume of fluid introduced into its inner space is also included within the present invention. The diameter of this type of balloon is fixed when manufactured and does not permit in situ adjustment of the balloon size. However, this type of balloon prevents possible over inflation and rupture if too much fluid is introduced into the balloon.

The flow reduction elements 200 shown in FIG. 4 have the shape of a round sphere. However, other shapes are contemplated and any shape that effectively functions to inhibit the passage of partially digested food in the small intestine is acceptable in accordance with the present invention. It is understood that the ability of the small intestinal insert to remain within the small intestine may be affected by the shape, orientation and tautness of the flow reduction elements 200. For example alternate shapes such as ovoid, elliptical, elongated ellipse and even irregular non-geometrical shapes could be used in accordance with the present invention.

Figure 5:
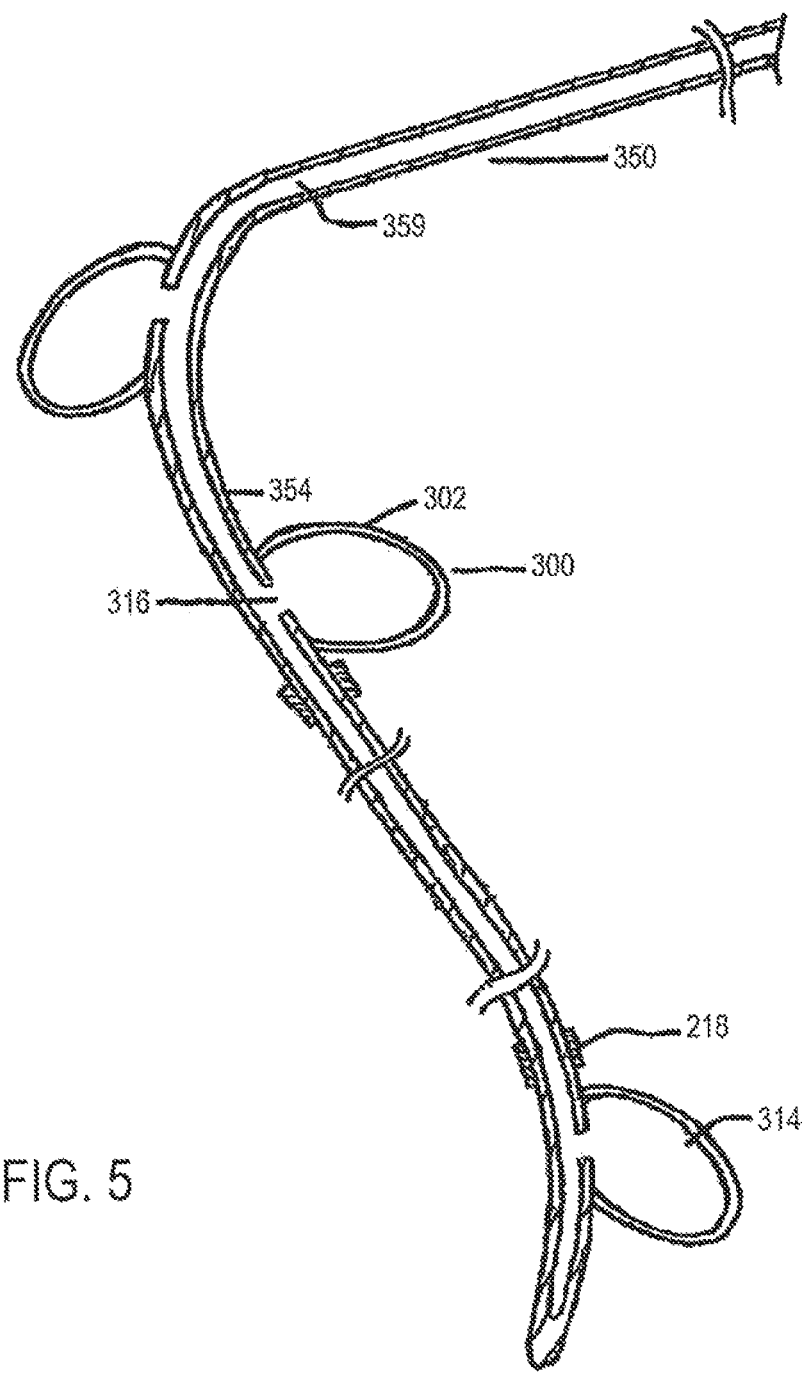
FIG. 5 is a partial section view of a central tube illustrating eccentrically attached flow reduction elements and a central lumen.

FIG. 5 illustrates an alternative embodiment of the present invention in which one or more flow reduction elements 300 are eccentrically attached to a central tube 350. In this embodiment the axis or diameter of the flow reduction element or elements 300 is not concentric with the axis of the central tube. The outer wall 302 of the flow reduction element is attached to the side of an outer wall 354 of the central tube 350. An inner space 314 of each flow reduction element 300 is eccentric relative to the axis of the central tube 350 and is in fluid communication with an inner lumen 359 of the central tube 350 through a respective opening 316. As was the case with the embodiment shown in FIG. 4, in the embodiment shown in FIG. 5 the inner lumen 359 may be used to introduce and remove fluid into the inner space 314 of the flow reduction element 300 to move the flow reduction element 300 between inflated and deflated configurations.

In some embodiments of the present invention, the flow reduction elements 300 may be inflated with a fluid, including a liquid and/or a gas. In some embodiments, the gas may be, for example, air, nitrogen or carbon dioxide. In another embodiment a liquid may be, for example, water or water mixed with other solutions. Any appropriate inflation medium may be modified to deliver bioactive materials or other solutions that may diffuse from the insert of the present invention into the small intestine to trigger biological signals of satiety. When bioactive materials are delivered through an inflation medium, the design of or the materials selected for all or a portion of the spine or central tube and/or flow reduction elements should be permeable to the bioactive materials. Porosity may be adjusted to control the diffusion rate of the bioactive materials.

In one alternative aspect, one or more reservoirs may be provided to store and/or control the release of one or more bioactive materials. In an alternative configuration of FIG. 7, one or more of the inflatable balloons 102 contain a bioactive material for delivery via the lumen 59 and ports to one or more elements on the spine or via the spine itself. The balloons may be filled before or after a device has been placed in a body or refilled while the device remains in the body. Filling may be performed using a valve, a port, a septum or a self-sealing mechanism provided for that purpose and accessible to a health care provider using endoscopic techniques. In still further aspects, the bioactive material within the balloons 102 may be used in conjunction with a fluid delivery system as described elsewhere in this application whereby the balloons 102 are the reservoir for the fluid being delivered based on the desired therapeutic outcome or therapy being performed When inflating the flow reduction elements of the present invention, it may be important for the physician to monitor the flow reduction element 300 location in the small intestine and the diameter of the flow reduction element relative to the diameter of the small intestine. For this purpose, the flow reduction element may be inflated with a radio opaque fluid that is visible on X-ray. When the flow reduction element contains radio opaque fluid, a physician may non-invasively visualize the size and placement of the flow reduction element(s) from outside the patient's body. This knowledge enables the physician to adjust the size and/or placement of the flow reduction element(s). Likewise radio opaque marker bands 218 as shown in FIG. 5 may be placed around the central tube to facilitate visualization of the central tube's location in the small intestine. The radio opaque marker bands 218 may be placed at predetermined intervals so that the distance inside the small intestine may be used as depth markers and may be measured from outside of the body.

The central tube and flow reduction elements of the present invention may be flexible. In some embodiments, they may be constructed of a polymeric material that may be easily formed or extruded and delivered with the aid of an endoscope by known techniques. A central tube 50 that is soft and flexible will contour to the anatomy of the gastro-intestinal tract and provide less irritation of the stomach and intestinal lining.

Figure 6:
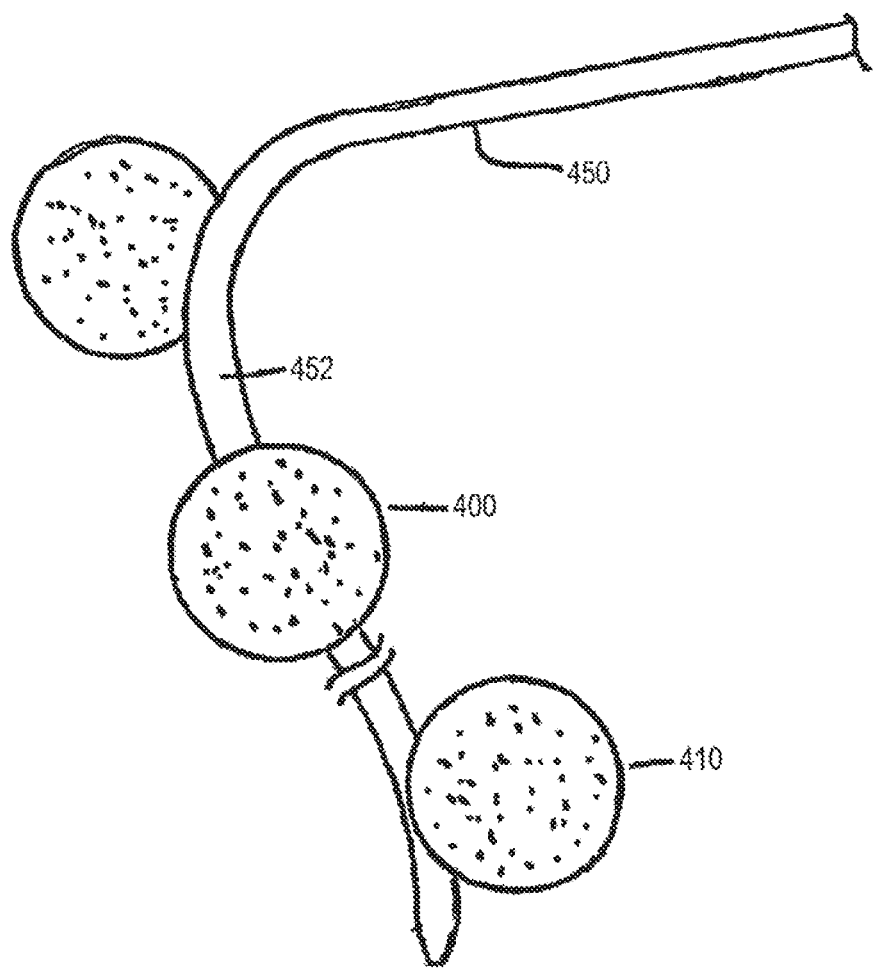
FIG. 6 is a perspective view of an alternative embodiment showing an elongated member and illustrating attached flow reduction elements.

FIG. 6 shows an alternative embodiment of the invention with flow reduction elements that are generally self-expanding, and do not necessarily include a central lumen. These embodiments include a central shaft 450 around which flow reduction elements are concentrically attached 400 and/or are eccentrically attached 410. The elements 400 and 410 may be attached to the central shaft 450 by, for example, heat fusing, adhesives or other suitable methods as known in the art. These flow reduction elements 400 may be made from material that may be folded or collapsed to a first volume suitable for insertion with the aid of an endoscope and then may self-expand to a second volume suitable for restricting the flow of partially digested food according to the present invention. These flow reduction elements may be made from materials, or materials may be configured so as to take the form of such as, by way of example, a sponge, a foam, a hydrogel, or springs that may be compacted into a small volume and then self-expand to a pre-determined shape and volume when unrestricted. Gel- or sponge-based embodiments may include open cell or closed cell forms. In addition to having features that allow such gel- or sponge-based embodiments to be collapsible and expandable for deployment, such embodiments typically have a high surface area which is beneficial in embodiments that may include bioactive agents, and may further be conducive for purposes of biodegradability. Another foam-related embodiment is described below in the section entitled "Further embodiments of the invention", and depicted in FIG. 21. Because the flow reduction elements self-expand, the need for an inflation system is eliminated and this embodiment represents a simple mechanical design. These flow reduction elements may also be impregnated with bioactive materials or other signals that may trigger biological signals of satiety.

The central shaft 450 of an embodiment such as that depicted in FIG. 6 may be solid and without an inner lumen or inner space. In another embodiment the central shaft 450 may include a passageway for consumed food so that the food may pass through the small intestine without being fully absorbed.

Deployment of Inserts and Flow Reduction Elements

Figure 9:
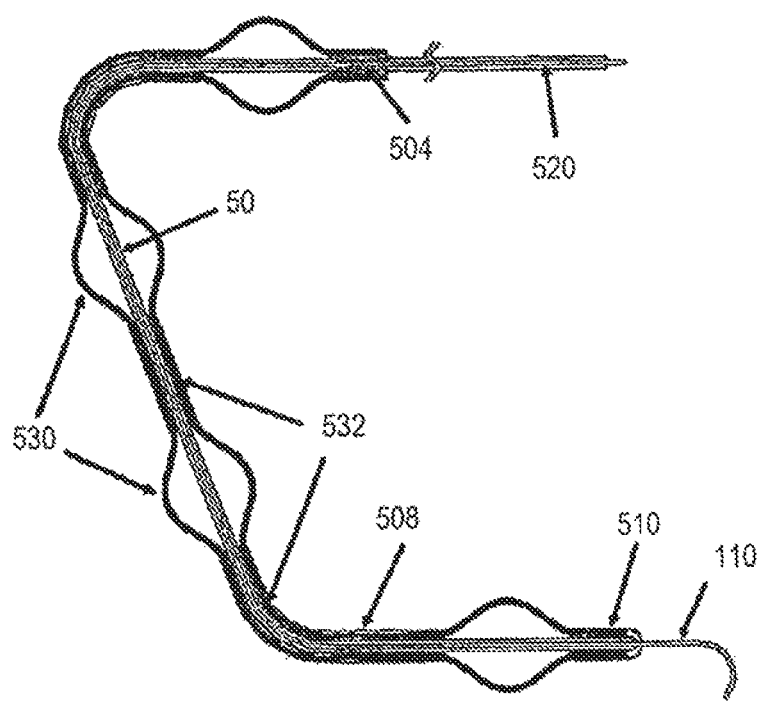
FIG. 9 illustrates a central tube attached to an expandable sleeve, the expandable sleeve allowing expansion of particular segments of the central tube to form flow reduction elements.

The description now turns to considerations related to deployment of the inventive insert, some embodiments of which include flow reduction elements. Flow reduction elements are referenced in a generic sense with the label 200, but some exemplary embodiments make use of different label numbers, for their particular features. FIG. 9 illustrates an embodiment of the present invention where flow reduction elements may be created through the expansion of portions of an expandable sleeve; this embodiment will be used in the context of describing an example of how to deploy a device with flow reduction elements. In the embodiment depicted in FIG. 9, a central tube 50 is attached to an expandable sleeve 508 at the expandable sleeve's distal end 510 near the distal portion of a duodenal/small intestinal insert of the present invention. In a delivery configuration of the depicted embodiment, the opposite proximal end of the central tube 50 is attached to a detachable extension tube 520 that may lock onto a proximal portion of the central tube 50 when the flow reduction elements 530 are expanded (post-delivery). One non-limiting method of detachable attachment is the use of one or more screws 504, whereby the extension tube 520 screws into the central tube 50. The central tube 50 may be pre-formed to have a configuration that conforms to the anatomy of the duodenum 10 shown in FIG. 1. A central tube 50 so described would force the expandable sleeve 508 to assume the configuration of the central tube 50. The central tube 50 may be constructed, merely by way of example, of wire, spring, superelastic or shape memory alloys, hollow steel tubing or plastic polymers. In some embodiments a stiffening rod or guide wire 110 may also be inserted through the lumen of central tube 50.

The expandable sleeve 508 herein described is designed to expand at predefined segments to allow the formation of flow reduction elements 530. In some embodiments, the non-expanded segments 532 of expandable sleeve 508 may be coated with a polymer to prevent their expansion. In another embodiment, the flow reduction elements 530 may be covered with a flexible polymer to prevent partially digested food from entering the flow reduction elements 530. In another embodiment, a stiffening rod or guide wire 110 may be inserted through the lumen of central tube 50 to straighten the central tube 50 when the device is delivered into the duodenum.

The expandable sleeve 508 may, merely by way of example be configured as any one or more of a knit, a weave, a mesh or a braid that may be formed, merely by way of example from any one or more of a metal, a wire, a ribbon, a plastic polymer or a biodegradable material.

Figure 10:
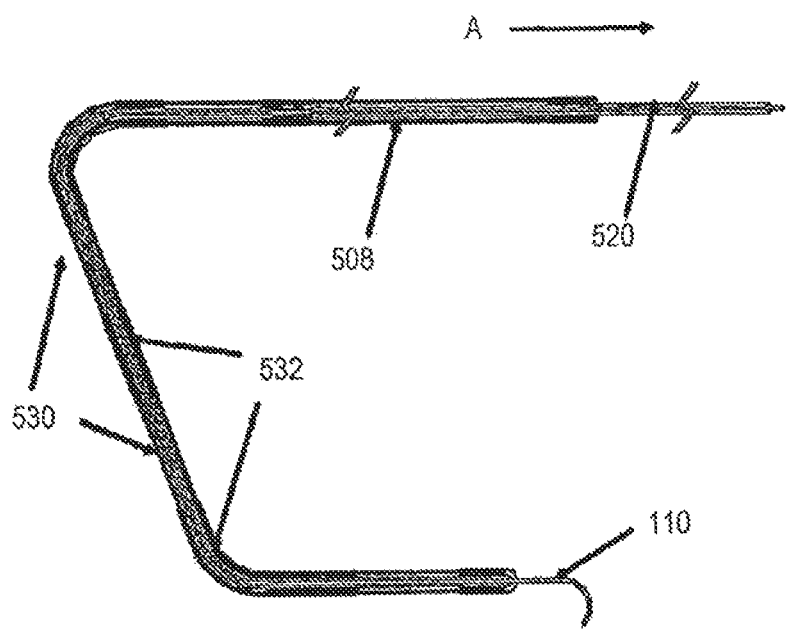
FIG. 10 illustrates an expandable sleeve in a collapsed configuration for insertion into the small intestine.

FIG. 10 illustrates the expandable sleeve 508 consisting of flow reduction elements 530 in a collapsed configuration for insertion into the small intestine. In this configuration a force A is applied to the expandable sleeve 508 to collapse the flow reduction elements 530. The collapsed form may be restrained by a constraining mechanism such as, merely by way of example, a sheath or a tightly wound string, or by applying sustained traction on the proximal end of the expandable sleeve 508. FIG. 10 also shows portions of the central tube that will remain unexpanded 532, a detachable extension tube 520 and a guidewire 110.

The expansion of the flow reduction elements 530 in the embodiments depicted in FIGS. 9 and 10 may occur passively or actively. One example of passive expansion may be the removal of a constraining mechanism to allow the flow reduction elements 530 to expand to an original expanded state. Another non-limiting mechanism can be to release traction on the proximal end of an expandable sleeve 508 to allow the flow reduction elements 530 to expand to an original expanded state.

Figure 11:
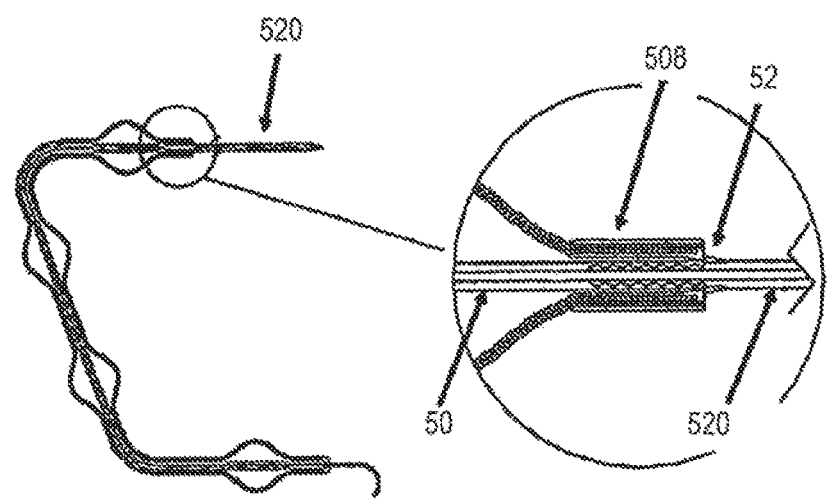
FIG. 11 illustrates one mechanism for keeping flow reduction elements formed with an expandable sleeve in a desired expanded configuration.

The flow reduction elements 530 of the embodiments depicted in FIGS. 10 and 11 can expand in a distal to proximal fashion, a proximal to distal fashion or in a central fashion depending on their relative position in relation to, in some embodiments, motion of the expandable sleeve 508 and the central tube 50 to one another. For example, if the proximal end of the flow reduction element lumen is held in the duodenal bulb and the central tube 50 is pulled back, the distal end of the flow reduction element lumen may expand first. Expansion in this direction may be advantageous because the position of the proximal end of the flow reduction element lumen remains in the duodenal bulb.

FIG. 11 illustrates some embodiments of the present invention that may lock the proximal end of the expandable sleeve 508 to the central tube 50 at a position to keep the flow reduction elements in a desired expanded configuration. Traction on the extension tube 520 retracts central tube 50 until wedge 52 engages the proximal end of the expandable sleeve 508. The central tube 50 may have multiple ratchet-like wedges that may lock the expandable sleeve 508 at different degrees of expansion. The extension tube may be unscrewed from the central tube 50 after deployment of the device and expansion of the expandable sleeve 508.

Use of the Device

Figure 12:
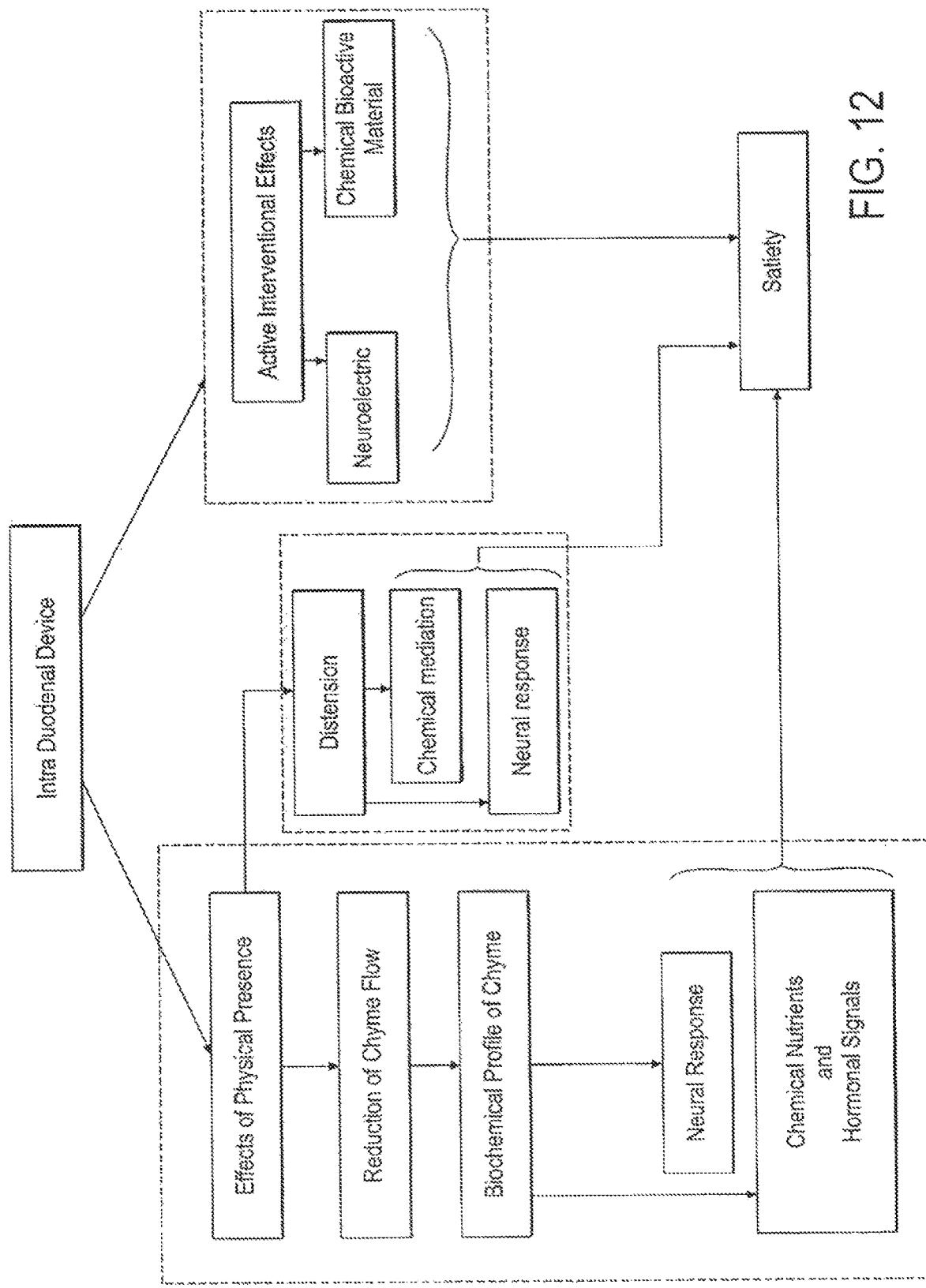
FIG. 12 is a flow diagram depicting the intestinal insert's role in contributing to the generation of one or more signals of satiety.

FIG. 12 is a schematic flow diagram of various embodiments of a method by which embodiments of the device engage the physiology of the host subject, and intervene in ways to generate a sense of satiety that ultimately reduces food intake. Embodiments of the inventive device intervene in the physiology of digestion and satiation by two broad approaches, each of which mimic or exploit the natural mechanisms of satiety. Embodiments may engage the physiology of the host subject by (1) their mere physical presence having effects, and/or (2) they may intervene more directly or actively by the direct provision of bioactive agents or direct neural stimulation. FIG. 12 and this associated description are provided as a simplified theoretical framework for understanding the invention; it is not intended to be complete in all detail; various interactions, dotted lines, and blurring of distinctions are omitted for sake of simplicity.

First, the mere physical presence of a device has two main effects, it has distensional effects and, if it has distinct flow reduction elements, it impedes the flow of chyme. Each of these two broad effects is dependent on the dimensions of the device and its flow reduction system, if the latter is present. First, then, the presence of the device distends the duodenum, and such distension may be neurally-sensed or detected, as for example, by stretch-sensitive neurons in the duodenum. Accordingly, any physical dimension, aspect, or feature, such as, by way of example, any of length, width, total volume, overall conformation or topography, density, weight, or surface properties may affect distension, or may be neurally detected in some way. Secondly, with regard to physically impeding the flow of chyme, this impeding process may alter the biochemical profile of digesting chyme, and chemoreceptors in the duodenum sense that profile as being more fully digested. It may also be that there is neural recognition more specifically of longer chyme residency time, as information separate from the altered biochemical profile per se; an effect such as that also then may be related to neural detection of distension. Neuronal pathways are indeed stimulated by distension, and neuroelectric signals and/or neuropeptides and neurotransmitters may be released for local or more distant sites of action. Joining neural feedback are chemical signals, both from the metabolite profile per se, and by the secretion of hormones such as CCK. Neural and chemical responses emanate to the central nervous system and other organs which, in sum, indicate that enough has been eaten, and satiation is achieved. In further response, the central nervous system supports a cessation of eating and digestive processes slow.

Second, with further reference to FIG. 12, embodiments of the device may intervene in a more active manner, beyond that which is provoked by mere physical presence. Embodiments of the device may assertively provide (1) bioactive agents and/or (2) provide electrical stimulation of nerves which then engage the physiology of satiety and digestion in the much the same manner, or through the same physiological pathways described above. In sum, a variety of effects of the presence of the device in the duodenum result in biochemical effects or signals (such as hormonal responses, and/or biochemical profile of metabolites both within the intestine and in the blood stream) and neural activity involving electrical signals, all of which converge physiologically to result in "satiety", with its complement of sensed satiety, sensed or perceived appetite, psychological correlates, and behavioral and habitual responses. As such, the action of the device or the presence of the device could be part of a method of providing therapy. The therapy may include providing a bioactive agent from the device to a portion of the gastrointestinal site. Moreover, this step of providing may produce a sensation of satiety in the patient.

Embodiments of the invention, a small intestinal insert, typically include an elongated member including at least one angled portion and at least one flow reduction element, for slowing the passage of chyme (or, stated in other terms, increasing the residency time of chyme) in the duodenum, although some embodiments of the device do not necessarily include a flow reduction element, and in some embodiments, the central or elongated member itself may be configured to reduce flow. These embodiments typically do have one or two angled portions that correspond to angled target portions of the duodenum. The configuration of the angled portions of the insert, including the flow reduction elements, is such that the device resides stably in the duodenum for a period of time. Embodiments of the insert may include adaptations that contribute to the generation of one or more physiological signals of satiety. Embodiments of the insert may include other features, such as the inclusion of biodegradable portions, a neurological stimulator, and one or more releasable reservoirs of bioactive materials that can be actively released by a bioactive material release mechanism.

Residency time of embodiments of the insert within the targeted angled site within the duodenum will vary according to the configuration of the embodiment and according to the particulars of the biodegradable materials that comprise portions of the device. Degradation of the device by biological processes is typically what causes release or unseating, or disengagement of the device from the target site, and elimination of the device through the intestinal tract. It may be understood therefore, that the device may be configured initially to sit or be seated in the targeted angled portion of the small intestine, and then, following a period of residency and through the effects of biodegradation, then configured to be unseated from the target site, and eliminated from the body by way of defecation. Biodegradability is feature of some polymers, and may be included in polymeric portions of any embodiment described herein.

Embodiments of the device elicit physiological signals of satiety typically through hormonal or neurological pathways. In some embodiments, the pathways are stimulated by the physical presence of the device, including a portion of or the sum total of a central member and flow reduction elements, whose collective or individual dimensions, either length, width, or total volume, or surface properties, are such that neuronal elements of the intestine, such as mechanoreceptors or stretch receptors, sense the presence of material which is interpreted as the presence of partially digested food, and therefore stimulate neuronal messages to the central nervous system that are interpreted as food satiation. In some embodiments, the central member, elongated body or spine may primarily provide the trigger for signaling. In some other embodiments, one or more flow reduction elements may primarily provide the trigger for signaling. In still other embodiments, a combination of the flow reduction element or elements and the elongated body provide the trigger for signaling.

In other embodiments, the satiety signal may be hormonal. Flow reduction elements slow the passage of chyme being processed in the duodenum, the biochemical profile of the food breakdown products is altered, and chemoreceptors in the duodenum respond to the altered biochemical profile in a manner that conveys satiety to the central nervous system and other portions of the digestive system.

In still other embodiments, the device includes reservoirs of bioactive materials that may be released, either by passive or active mechanisms. In the embodiments, the satiety signals are provided directly by the device, not by the endocrine pathways of the insert's host. Embodiments of the device may include material reservoirs of any type, including, for example, drug coatings that elute passively, or in concert with degradation of a host coating material, and some embodiments include reservoirs that are coupled with pumps. Such pumps may be mechanical, harnessing for example, biological energy conveyed by peristalsis, or electrical energy, or mechanical energy. Some embodiments may include osmotic pumps. which do not require input of electrical energy, but instead tap into the stored energy of osmotic gradients. Embodiments that are dependent on electrical energy for release by a pump typically include an energy storage device, such as a battery or a capacitor. Some of the powered embodiments include, as part of a larger system, a remote stimulator that can control the action of the pump. In some embodiments, the device may provide direct neural stimulation, through electrodes that stimulate local nerves in the duodenum, which convey a sensation of satiety to the central nervous system. As with pumps, devices that include neural stimulation features, may also include energy storage devices and external on/off or variable power control devices that communicate either by direct wired connection or wirelessly, as for example through radiofrequency signals.

Figure 13:
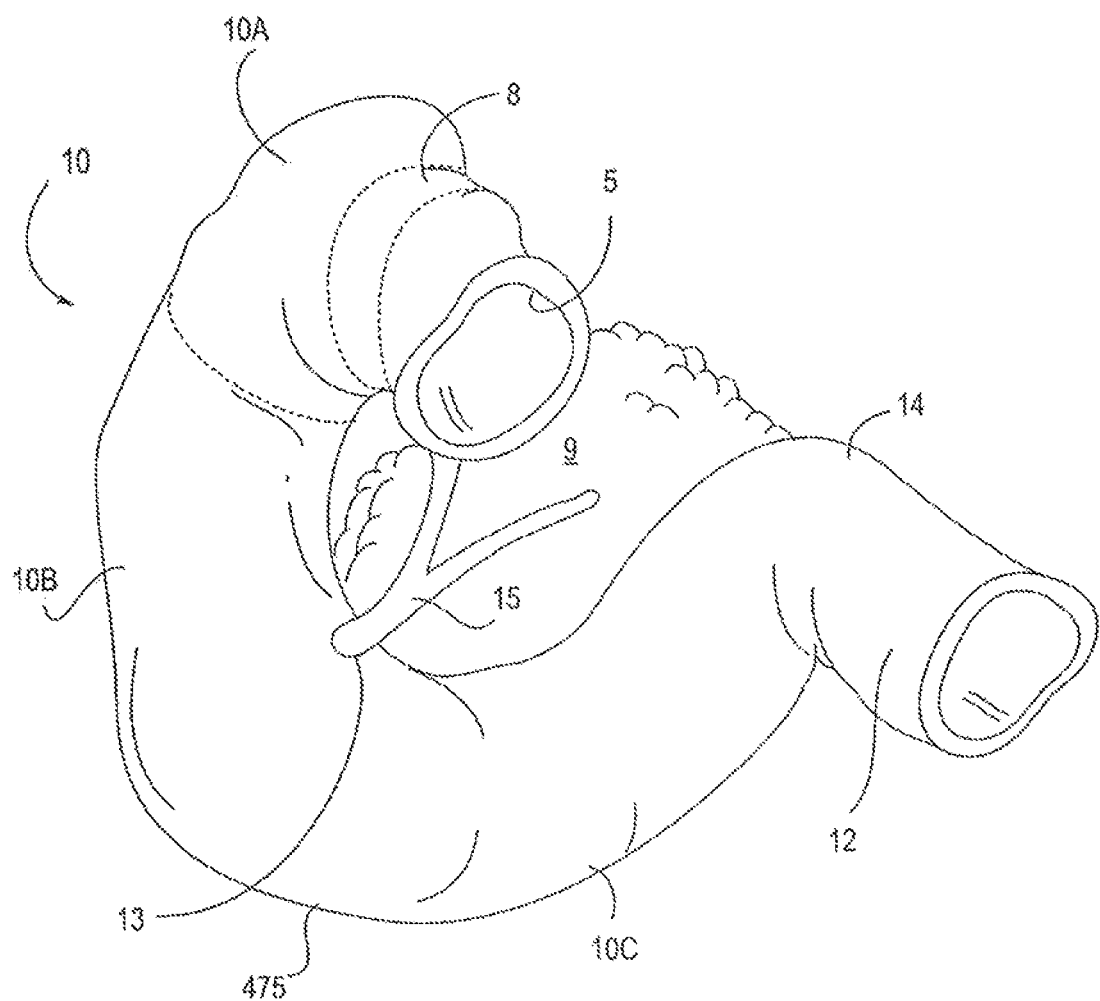
FIG. 13 is perspective view of the duodenum.
Figure 14:
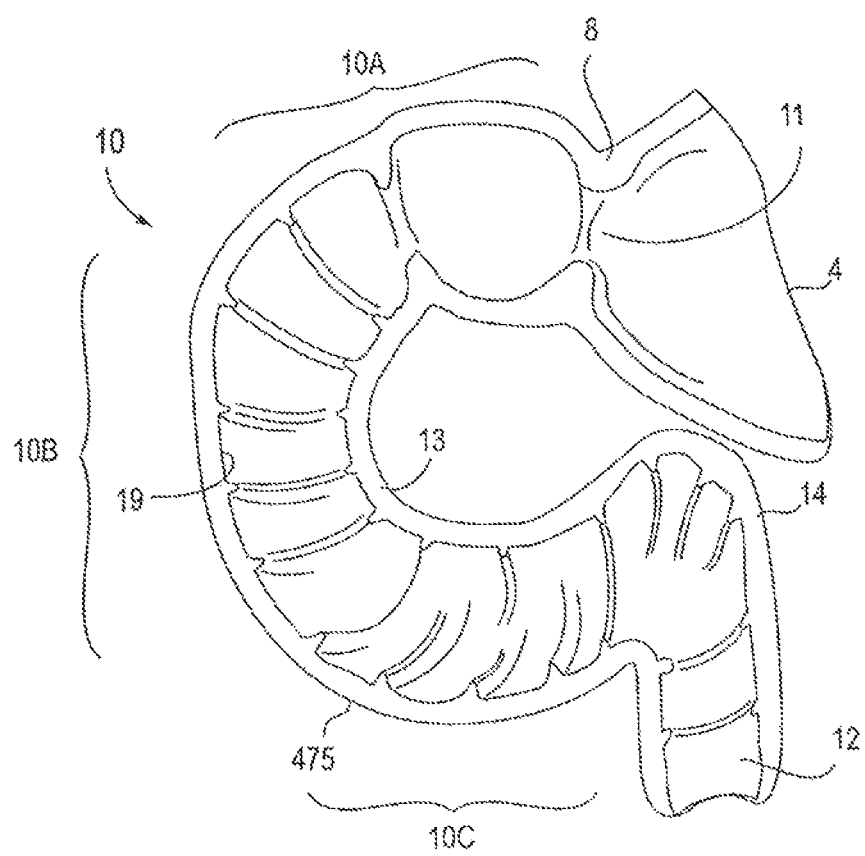
FIG. 14 depicts a side view of the duodenum, showing the folds of rugae that form the periphery of the inner space within which embodiments of the insert device are positioned.

FIG. 13 provides a perspective view of a portion of the human gastrointestinal tract that focuses on the duodenum of the small intestine 10, starting at the antrum-pyloric juncture 5, and extending to the entrance of the jejunum 12. Shown are the ampulla of Vater 13, the site of the entrance of the hepatopancreatic duct 15, which is formed by the union of the pancreatic duct (from the pancreas 9) and the common bile duct from the liver. The pylorus 8 controls the discharge of contents of the stomach through a sphincter muscle, the pyloric valve 11, which allows the pylorus 8 to open wide enough to pass sufficiently-digested stomach contents. These gastric contents, after passing into the duodenum 10, continue into the jejunum 12 and on into the ileum. The duodenum 10, jejunum 12 and ileum make up what is known as the small intestine; however the individual portions of the alimentary canal are also commonly referred to as the small intestine. In the context of this invention the small intestine can refer to all or part of the duodenum, jejunum and/or ileum. FIG. 14 provides a flattened planar view of the duodenum 10, including the rugae 19, or inner-folding lining portion of the duodenum that form the periphery of the inner space within which embodiments of the insert device are positioned. Also depicted are the pylorus 8, the pyloric valve 11, the duodenal bulb 10A, the vertical duodenum 10B, and the horizontal duodenum 10C, the ampulla of Vater 13, and the initial portion of the jejunum 12. This figure provides a visual background for many of the figures that follow, each of which depicts an embodiment of the inventive inserted device seated within the targeted site of the duodenum.

Conformationally-Stabilized Devices in a Residence Site: General Considerations

Embodiments of the invention include devices or intestinal inserts with an elongated member with a proximal end and a distal end and an angled or curved portion between the proximal end and the distal end. The curved portion typically corresponds to a curved aspect of a residence site in a lumen of the body, for example, a portion of the gastrointestinal tract, and more particularly, the duodenum. The device is stabilized against distal or proximal movement relative to the residence site by a conformation that corresponds to the residence site, and more particularly, such conformation does not correspond to a site immediately distal and/or proximal to the residence site. Depending on the particulars of device design and location of a residence site, the device conformation may stabilize the device against proximal device movement, distal device movement, rotational device movement or a combination of any of these movements. Typically in luminal sites within the gastrointestinal tract there is a greater accumulation of forces that tend to move a device situated therein in a distal direction than in a proximal direction, as the general flow of contents, and the direction of peristalsis are both distally-directed. Accordingly, it is of particular importance that the device be stabilized against a distal-ward drift. Additionally, devices described herein are also suited to resisting proximal directed forces such as regurgitation. Accordingly, some embodiments of devices described herein are configured to resist gastrointestinal forces that may dislodge the device from a residence site whether the forces are proximally directed or distally directed.

Some embodiments of conformationally-stabilized devices, as described herein, do not rely on a hard or specific attachment or tethering anchor to stabilize at a target residence site, nor do they rely on an anchoring mechanism that resists downward drift by being blocked at a site of radial dimension limitation, such as the pylorus. Instead, embodiments of the device stabilize at a residence site by virtue of the conformation of the device in part or as a whole fitting into the residence site. Moreover, the device has sufficient structural integrity that it resists being moved relative to the residence site because an immediately distal and/or proximal location does not conformationally accommodate the device. Other embodiments include a proximal anchor which, in conjunction with conformation of the device, ensures that the device will stay in place in the duodenum.

The conformation of a device that provides its stability in a residence site refers to the physical totality of the device, including the dimensions in units of measure such as length, width, and volume, as well as shape, which relates to the distribution of the dimensions in space. While not desiring to be bound by theory, it is believed that a device self-stabilizes at a residence site because that position within the residence site represents the state of least free energy in a system that includes the device and the residence site. In other aspects, ends proximal and distal to the corresponding curved portion are in proximity to one another for further stability.

Aspects of the device that are adapted to provide conformational stabilization at a target site in a lumen of the body include physical dimensions of length and width, as well as angles or curvature assumed by the lumen. Conformationally stabilized (or conformationally-stabilizable devices) may vary with respect to the degree to which their physical aspects of size and shape correspond to the size and shape of the intraluminal residence site to which they are targeted; their characteristic feature is that it is their conformation that stabilizes them against movement from the target site, once situated therein. More particularly, it is typical that such stabilization involves at least one curved or angled portion of the device that is accommodated by a corresponding at least one curved angled portion of the residence site, and the angled portion of the device characteristically provides a curvilinear retaining force within that site.

Some conformationally stabilizable embodiments may further stabilize in a residence site by providing radially outward force that meets the surrounding wall of the lumen. Conformationally stabilizing devices further may vary with regard to their stiffness or compliance in response to forces exerted upon them by the luminal residence site. A device with a high degree of stiffness bends or changes its own shape relatively little in response to forces exerted by the residence site, while a highly compliant device offers little resistance and complies with forces exerted on it by bending or changing shape. A con formationally stabilized device thus must have a sufficient degree of stiffness and overall structural integrity in order for its conformation to maintain its stability.

Some embodiments of a conformationally stabilizing device have a high degree of size and angular correspondence to their target site, in which case the residence site substantially retains its native configuration when occupied by the device. In some of these embodiments with a high degree of correspondence to the target site, the angles and the placement of angles along the length of a device substantially match the shape and linear dimensions of the residence site. In other embodiments, the device, in spite of having a conformation that as a whole stabilizes it at a residence site, the device, or more specifically, the preferred or unconstrained conformation of the device may nevertheless vary in terms of size and shape with respect to the target site. In some embodiments, a device with a preferred configuration that varies with respect to the residence site does not substantially change the shape of the residence site, as the device may be more compliant than the residence site. In some embodiments of devices that vary in conformation from that of the residence site, the device, if provided with sufficient stiffness and conformational integrity, may impart a change of shape to the luminal residence site. Typically, the configuration of devices that changes the shape of residence site is a feature that contributes to the stability of the device in that target site.

Some embodiments of the conformationally-stabilizing device are configured such that the conformation of the structure as a whole, including substantially the totality of physical features, is substantially directed toward providing conformational stability. With other embodiments, however, some aspects of the conformation of various physical features may not be directed specifically toward providing conformational stability, but rather may be directed toward another functional or therapeutic end, such as reducing the flow of chyme (as detailed in U.S. patent application Ser. Nos. 11/300,283 and 11/807,107), or toward other therapeutic purposes or modalities, as described further herein below. In other embodiments, physical features may not be designed singularly to support conformational stability, but, rather such features may be designed such that they serve one or more functional purposes. A physical feature may, for example, contribute both to providing conformational stability and toward another functional or therapeutic purpose. In any of these aforementioned embodiments that include physical features that are not specifically-focused or singularly-focused on contributing to the stability of the device within the residence site, these embodiments nevertheless have a sufficient total level or amount of conformational features that are directed toward supporting conformational stability that the device is capable of stabilizing in a residence site by virtue of such totality of conformation, particularly in gastrointestinal luminal sites that include one or more curvilinear or angled aspects.

Some embodiments are targeted to the duodenum and described in detail, but other embodiments are targeted to residence sites elsewhere in the gastrointestinal tract. Further, as mentioned above, some devices are configured to align with a high degree of correspondence with their designated residence site, while other vary in correspondence, and by such variance may alter the shape of the residence site. Further, some devices, though stabilized substantially by the conformation of the device which precludes movement that displaces it from the residence site, may further derive site-stabilizing benefit from a balance of materials-based and construction-based features such as structural integrity, elasticity, stiffness, and ability to counter lumen-generated radially-inward force with a radially-outward counterforce.

Conformation refers to the physical totality of the device, including the dimensions in units of measure such as length, width, and volume, as well as shape, which relates to the distribution of the dimensions in space. While the claims to this invention are not bound by theory, to understand the invention it can theorized that a device self-stabilizes at a duodenal residence site because its residence there represents the state of least free energy in a system that includes the device within the gastrointestinal tract.

Some embodiments of the duodenal device are configured to reside within gastrointestinal tract residence sites completely within the duodenum. The duodenum is anatomically situated distal to the pylorus and stomach and proximal to the jejunum, as illustrated in FIG. 13. Some other embodiments, however, may include portions that extend proximally in a minimal manner, into the pylorus, and some may extend further proximally into the antrum of the stomach. Some embodiments may extend further distally, past the site of the ligament of Treitz, and into the jejunum. However, even these embodiments that include portions extending proximally or distally from the duodenum still rely on conformational stabilization within the duodenum to preclude dislodgment from the residence site and consequent movement of the device as a whole. As a result, such embodiments do not rely, for example, on being constrained from distal or downstream movement by the radial constraint of the pylorus.

The duodenal residence site of embodiments of the device includes at least one angled portion, and the device, accordingly has at least one angled portion that corresponds to that angled portion within the residence site. Other embodiments of the device may include two, three, four, or more angled portions between the proximal and distal end of the device, these angles corresponding to angles in a residence site. The duodenal residence site can also be understood as a continuous curvilinear form, and accordingly, some embodiments of the device are configured as a curvilinear form, without particular angled regions.

Example of Duodenal Devices with a Proximal End Terminating in the Gastric Antrum and a Distal End Terminating Near the Duodenojejunal Junction Turning now to illustrative examples of embodiments of devices and various features, as described above, which have a proximal end terminating in the gastric antrum, a distal end terminating in the region of the duodenojejunal junction, and a central curved portion configured to conform to a duodenal lumen between its proximal and distal ends. The device described with respect to FIG. 15 (or any of the devices described herein) can further include a proximal anchor configured to anchor the device in the duodenum.

Figure 15:
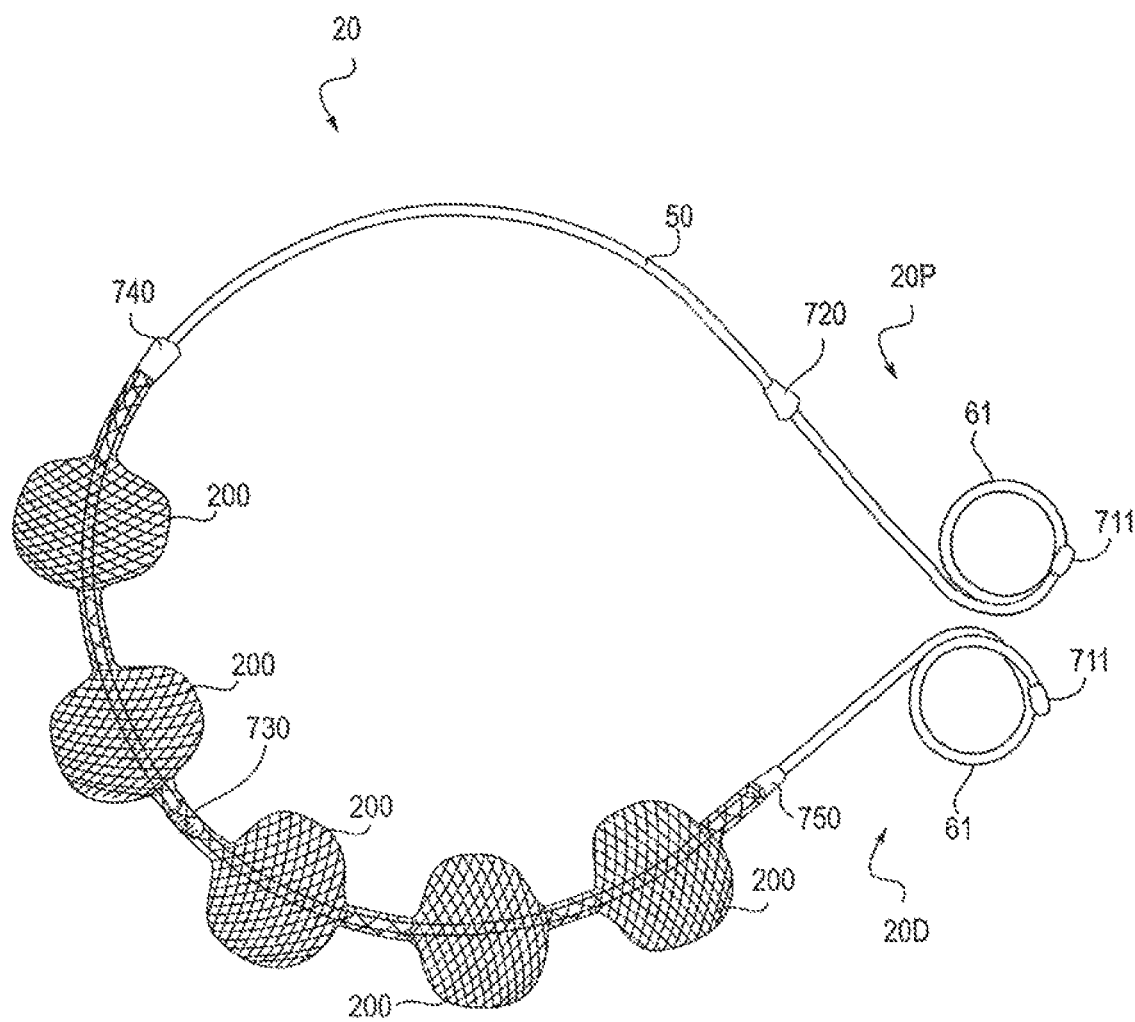
FIG. 15 shows an embodiment of a device that has flow reduction elements formed from a sleeve and that has proximal portion that terminates in the gastric antrum; and the distal portion terminates near the duodenojejunal junction.

FIG. 15 shows an embodiment of a device 20 including flow reducing elements 200 along a spine 50 having a proximal portion 20P that terminates in the gastric antrum; and the distal portion 20D that terminates near the duodenojejunal junction. The spine 50 of central curved portion forms a loop, with the proximal 20P and distal 20D ends coming to be in near apposition with each, and in some cases crossing each other near their termini. The device in FIG. 15 is depicted into its preferred configuration, i.e., the configuration it assumes at rest. As described above, the devise can be forced into a linear configuration for inclusion in the working channel of an endoscope in preparation for deployment. Once implanted in the residence site in the gastrointestinal tract, the overall configuration of the device approaches the preferred configuration, but is generally slightly constrained. For example, the overall curvature may be made slightly more obtuse, by the counterforce exerted by the gastrointestinal tract on the device.

Also depicted in FIG. 15 is a flow reducing element 200 comprising braided filaments that form a plurality of radially-expanded segments; the braided element is arranged in a coaxial manner around the Nitinol body of the device. The figure depicts five segments, but the number may vary, as described above. The braided flow reduction element 200 is fixed to the device at its distal end, but freely slidable on its proximal end within limits. A proximal sliding movement limit is represented simply by the length the braided element. The slack for sliding comes from the trade-off between radial expansion of the expandable segments and the absolute linear length of the braid as the expandable segments are drawn in. The distal limit on the slidable range of the braided element is provided by slide stopper feature 730. This feature is fused to the Nitinol body and has a radial profile over which the braided element 200, itself, can freely slide, but sufficiently high that it blocks distal movement of an end ring 740 at the proximal terminus of the braided element 200. The purpose of this stop feature 730 is to prevent an extreme distal movement or collapse of the braided element as whole, which could defeat its function (i.e., to reduce chyme flow, not to block it).

Also depicted in FIG. 15 is a pushable shoulder 720 on the proximal portion of the device, the purpose of which is to provide a surface against which a pushing element can eject the device (in its linearized configuration) from the working channel of an endoscope.

Figure 17:
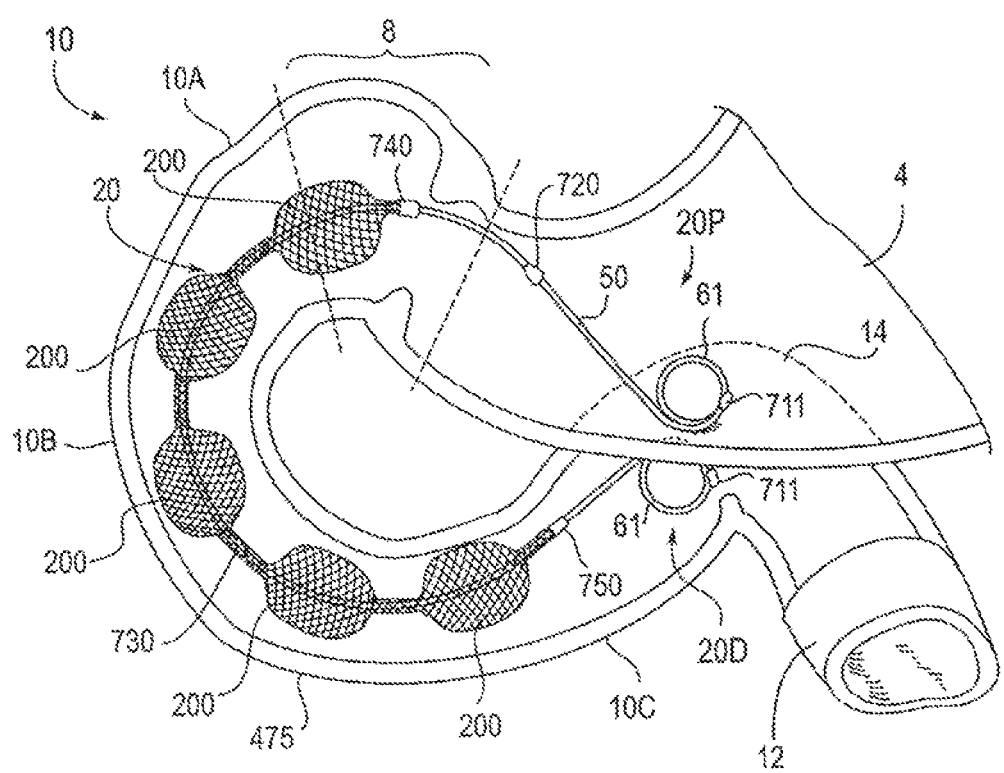
FIG. 17 shows the device depicted in FIG. 15 in a gastrointestinal residence site, with the proximal portion terminating in the gastric antrum, and the distal portion terminating near the duodenojejunal junction.

FIG. 17 shows the device 20 depicted in FIG. 15 in a gastrointestinal residence site, with the proximal portion 20P of the device terminating in the gastric antrum, and the distal portion 20D terminating near the duodenojejunal junction or the duodenojejunal flexure 14. It can be seen that the portion of device 20 that transits through the pylorus 8 is a bare portion of the device, without the flow reduction element 20. The dimension of the spine 50 alone is sufficiently small that the pylorus does not feel its presence, an advantageous feature as described above.

Figure 18:
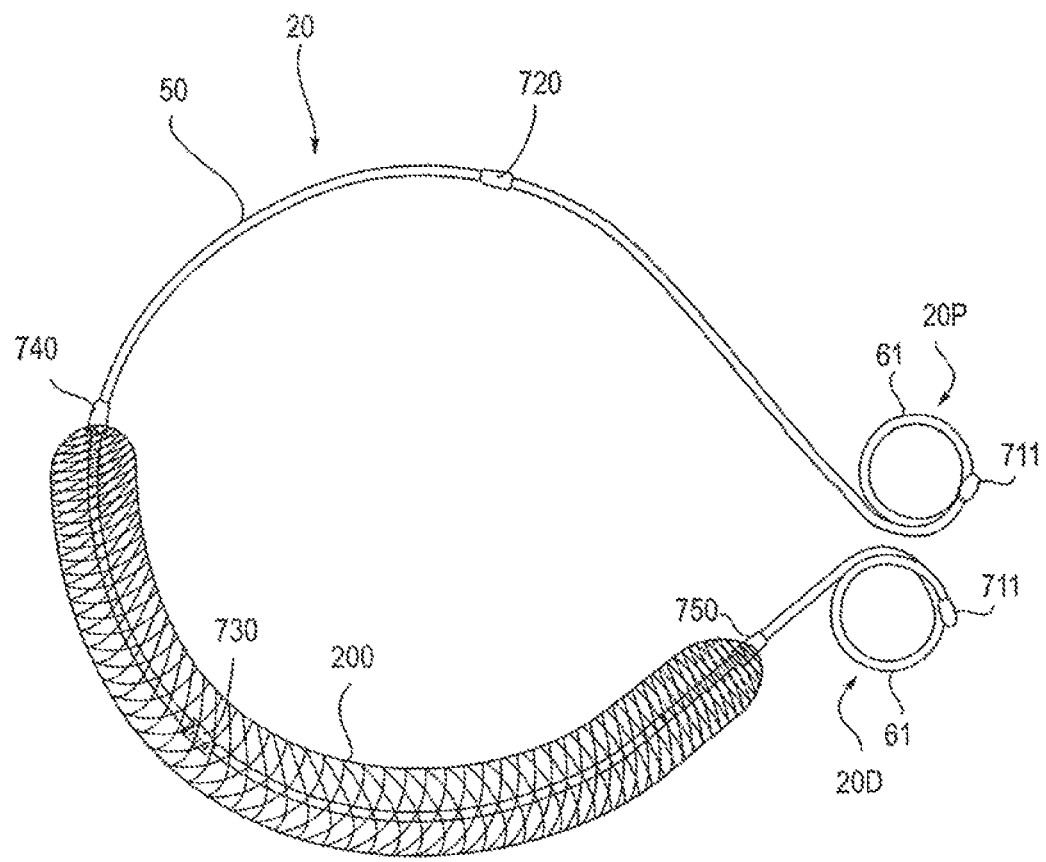
FIG. 18 shows an alternative embodiment of a device similar to that shown in FIG. 15, with a large single flow reduction element.

FIG. 18 shows an alternative embodiment of a device 20 similar to that shown in FIG. 15, with a large single flow reduction element. Other features of the device are substantially the same as those described above with reference to FIG. 15. This embodiment may have therapeutic advantages for some particular applications of the device.

In some embodiments of the inventive device, one or more flow reduction elements may be positioned on the device so that when implanted the flow reduction element is within a specific portion of the anatomy or within a position where the flow element with produce a desired result. Possible locations for one or more flow reduction elements include: (a) within the duodenal bulb; (b) within the proximal duodenum; (c) distal to the duodenal bulb; (d) distal to the duodenal bulb and within the vertical duodenum; (e) within 5 cm of the pylorus; (f) one or more positions within the duodenum selected to increase the probability of rector activation in the duodenum (for specific location examples see Ritter article mentioned above and specifically incorporated by reference).

In one aspect of the present invention, the proximal and distal ends of the device are in close proximity once the device is implanted into a residence site. In one aspect, the proximal end is within 1 cm to 7 cm the distal end. In another aspect, the proximal end is within 1 cm to 3 cm of the distal end. In still another aspect, the proximal end is within 1 cm to 5 cm of the distal end. In still another aspect, the proximal and distal ends be separated by 1 cm or less or may even urge the adjacent tissue into contact. However, in these embodiments, the contact will urge tissue movement and may produce contact between the stomach and the duodenum but without providing sufficient pressure against the involved tissue to form a pressure necrosis or cause erosion or damage to the involved tissue.

Embodiments Having an Extended Proximal or Distal End

FIGS. 19-23 illustrate embodiments of the inventions described herein in relation to the esophagus 2, the stomach 4, the duodenum 10, and the jejunum 12. The duodenum 10 includes the duodenal bulb 10A, the vertical or descending duodenum 10B, the horizontal duodenum 10C, and ascending duodenum 10D as described herein in. Other anatomic features shown in the various figures include the esophagus 2, the esophageal sphincter 6, the stomach 4, jejunum 12 and duodenojejunal flexure 14 region of the duodenum 10. These embodiments also illustrate the various portions of the stomach 4 including the greater curvature 4A, lesser curvature 4B and fundus 4C.

Figure 19:
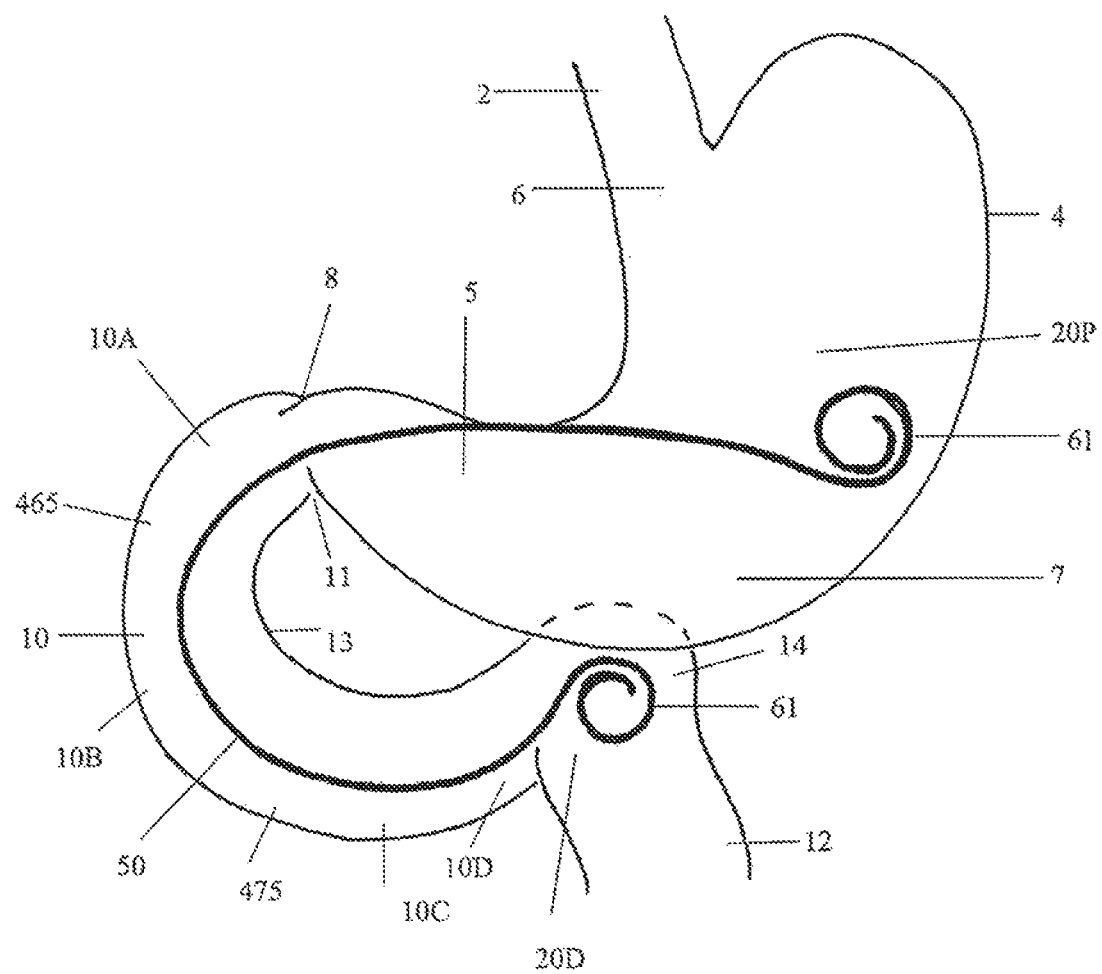
FIG. 19 shows a section view of the stomach with a device implanted into the duodenum having an proximal portion extended beyond the active portion of the stomach.
Figure 20:
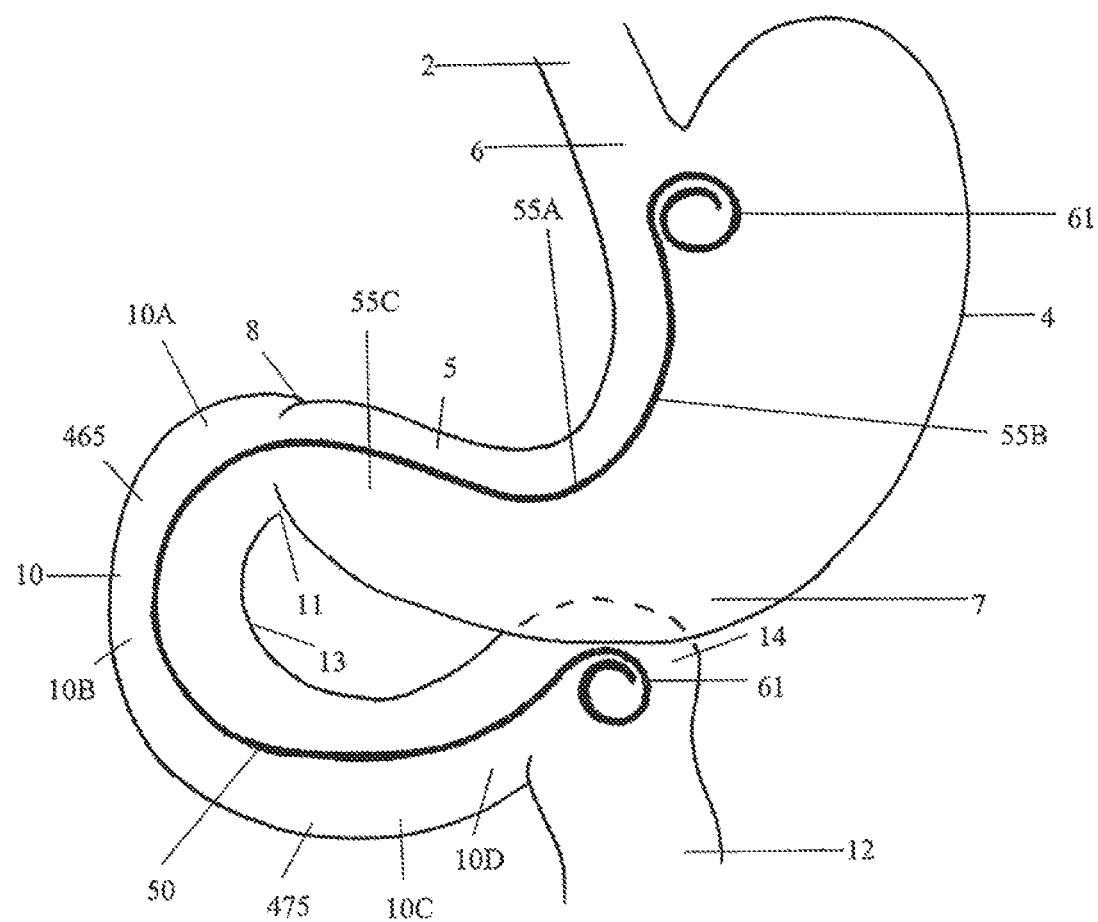
FIG. 20 shows a section view of the stomach with another device implanted into the duodenum having an alternative proximal portion extended beyond the active portion of the stomach.
Figure 21:
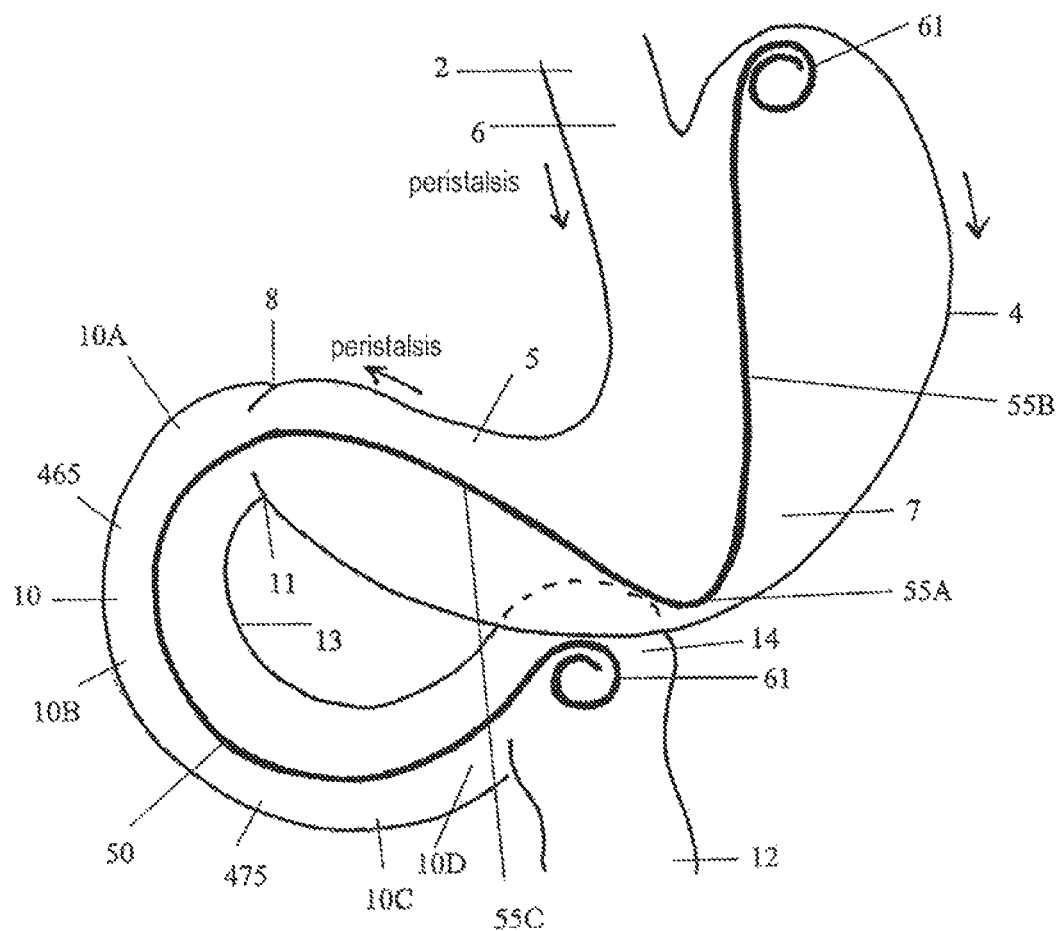
FIG. 21 shows a section view of the stomach with another device implanted into the duodenum having an proximal portion extended beyond the active portion of the stomach.

In one aspect, the embodiments of FIGS. 19-21 provide variations to the proximal end of a device. The proximal device end is extended such that the terminal end is within the stomach proximal to the pylorus. Still further, the proximal end, proximal terminal end or a feature of the proximal end of the device is positioned beyond (i.e., proximal to) the active region of the stomach. In this embodiment, the active region of the stomach refers to that portion of the distal stomach near or about the pyloric valve 11, pylorus 8 and antrum 7. In the examples that follow, the length, curvature or shape of the spine 50 is adjusted to place the proximal portion of the device into stomach regions beyond the active regions. Other details of the device spine, functional features and distal end may vary according to the other alternative aspects described herein. It is appreciated that the lengthening aspects that follow may be applied to other embodiments in order to vary the length of the device or to alter the relative positions of the proximal and distal ends of an implanted device from those positions shown and described above.

FIG. 19 provides a section view distal esophagus, stomach, duodenum and proximal jujunem with an implanted device extending from a proximal portion within the stomach and a distal portion beyond the horizontal duodenum at or near the near the duodenojejunal junction. In this embodiment, there is a spine 50 and ends 61 similar in the form to that of FIG. 15. The spine 50 of the embodiment of FIG. 19 differs in that the its length produces a residence site placement of the device with a proximal portion 20P that terminates beyond the gastric antrum 7 and the distal portion 20D that terminates near the duodenojejunal junction. The length may vary from that illustrated. For example, the length of the spine 50 may be altered so as to place all or a portion of the proximal portion 20P or the end feature 61 into contact with the stomach wall opposite or adjacent to the pyloric region. The length may be adjust to have the proximal portion 20P just in contact or in varying degrees of firm apposition with the inner wall of the stomach. As with the prior embodiments, the spine 50 of central curved portion forms a loop at the terminal ends of the proximal 20P and distal 20D ends. Alternatively, the device may have end portions or other atraumatic terminal ends. The device depicted in FIG. 19 is within the anatomy in its preferred configuration, i.e., the configuration it assumes at rest and after deployment. As described above, the device can be forced into a linear configuration for inclusion in the working channel of an endoscope in preparation for deployment. Once implanted in the residence site in the gastrointestinal tract, the overall configuration of the device approaches the preferred configuration, but is generally slightly constrained. For example, the overall curvature may be made slightly more obtuse, by the counterforce exerted by the gastrointestinal tract on the device.

FIG. 20 provides a section view distal esophagus, stomach, duodenum and proximal jujunem with an implanted device extending from a proximal portion beyond the active portion of the stomach and a distal portion beyond the horizontal duodenum at or near the near the duodenojejunal junction. The spine 50 of the embodiment of FIG. 20 differs from the embodiment of FIG. 19 in that the its length produces a residence site placement of the device with a proximal portion 20P that terminates beyond the gastric antrum 7 but along the lesser curvature 4C. Additionally, the curvature of the spine 50 alters at an inflection point 55A. The inflection point 55A represents the change in the overall curvature of the spine 50 producing a proximal region 55C and a distal region 55B. The curvature of the spine 50 may also vary in the region proximal to the inflection point (region 55C) or distal to the inflection point (region 55B). In the illustrated embodiment, the curvature of the inflection point 55A along with the curvature of the proximal region 55B cooperate that portion of the spine where the proximal portion or end shifts in order to place all or a portion of the proximal end along the lesser curvature. The inflection point 55A may be viewed as a transitional radius of curvature between the proximal portion shaped and configured to conform to the lesser curvature and the central spine portion shaped and configured generally to the curvature of the lower stomach and duodenum.

The length of the device may vary from that illustrated in FIG. 20. For example, the length of the spine 50 may be altered so as to place all or a portion of the proximal portion 20P or the end feature 61 into contact with the stomach wall along the lesser curvature 4 near the pylorus, near the lower esophageal sphincter 6 or at any place along the lesser curvature 4. The characteristics of the proximal portion may be adjusted to have the proximal portion 20P just in contact or in varying degrees of firm apposition with the stomach wall of the lesser curvature. Characteristics of the proximal portion such to modifications include, for example, one or more of the angle of the spine at the inflection point 50A, the cross section shape of the spine or the size or shape of the terminal end.

As with the prior embodiments, the spine 50 of central curved portion in FIG. 20 forms a loop 61 at the terminal ends of the proximal 20P and distal 20D portions. Alternatively, the device may have end portions or other atraumatic terminal ends. The device depicted in FIG. 20 is within the anatomy in its preferred configuration, i.e., the configuration it assumes at rest and after deployment. As described above, the device can be forced into a linear configuration for inclusion in the working channel of an endoscope in preparation for deployment. Once implanted in the residence site in the gastrointestinal tract, the overall configuration of the device approaches the preferred configuration, but is generally slightly constrained. For example, the overall curvature may be made slightly more obtuse, by the counterforce exerted by the gastrointestinal tract on the device.

FIG. 21 provides a section view distal esophagus, stomach, duodenum and proximal jujunem with an implanted device extending from a proximal portion beyond the active portion of the stomach and a distal portion beyond the horizontal duodenum at or near the near the duodenojejunal junction. The embodiment of FIG. 21 replaces vertical proximal anchor having a proximal end curved so as to extend up into the upper stomach. Moreover, this type of anchor may include one or more undulations in the central member to aid in maintaining position and resisting peristaltic action. The spine 50 of the embodiment of FIG. 21 differs from the embodiments of FIGS. 19 and 20 in that the length produces a residence site placement of the device with a proximal portion 20P that terminates beyond the gastric antrum 7 but towards the upper stomach. In the illustrative embodiment, the terminal end 61 is within the fundus 4C. As with the embodiment of FIG. 20, the curvature of the spine 50 alters at an inflection point 55A. The inflection point 55A represents the change in the overall curvature of the spine 50 producing a proximal region 55C and a distal region 55B. The curvature of the spine 50 may also vary in the region proximal to the inflection point (region 55C) or distal to the inflection point (region 55B). In the illustrated embodiment, the curvature of the inflection point 55A along with the curvature of the proximal and distal regions 55B, 55C cooperate so that the proximal portion or end shifts in order to place all or a portion of the proximal end along or within the upper stomach or fundus 4C. The inflection point 55A may be viewed as a transitional radius of curvature between the proximal portion shaped and configured to conform to the lesser curvature and the central spine portion shaped and configured generally to the curvature of the duodenum. Peristalsis (indicated generally by arrows) produces a downward motion on the proximal portion 20P thereby pressing the inflection point 55A into the stomach wall rather than towards the pyloric region or towards the pylorus.

The length of the device may vary from that illustrated in FIG. 21. For example, the length of the spine 50 may be altered so as to place all or a portion of the inflection point 55A near the pylorus or antrum while the proximal portion 20P or the end feature 61 is placed into contact with the stomach wall along the fundus 4C or upper portion of the stomach or greater curvature 4A or at any place along the greater curvature 4A. The characteristics of the proximal portion may be adjusted to have the proximal portion 20P just in contact or in varying degrees of firm apposition with the stomach wall. Characteristics of the proximal portion such to modifications include, for example, one or more of the angle of the spine at the inflection point 55A, the curvature and/or length of the proximal region 55C, the curvature and/or length of the distal region 55B, the cross section shape of the spine or the size or shape of the terminal end.

As with the prior embodiments, the spine 50 of central curved portion in FIG. 21 forms a loop 61 at the terminal ends of the proximal 20P and distal 20D portions. Alternatively, the device may have end portions or other atraumatic terminal ends. The device depicted in FIG. 21 is within the anatomy in its preferred configuration, i.e., the configuration it assumes at rest and after deployment. As described above, the device can be forced into a linear configuration for inclusion in the working channel of an endoscope in preparation for deployment. Once implanted in the residence site in the gastrointestinal tract, the overall configuration of the device approaches the preferred configuration, but is generally slightly constrained. For example, the overall curvature may be made slightly more obtuse, by the counterforce exerted by the gastrointestinal tract on the device.

Figure 22:
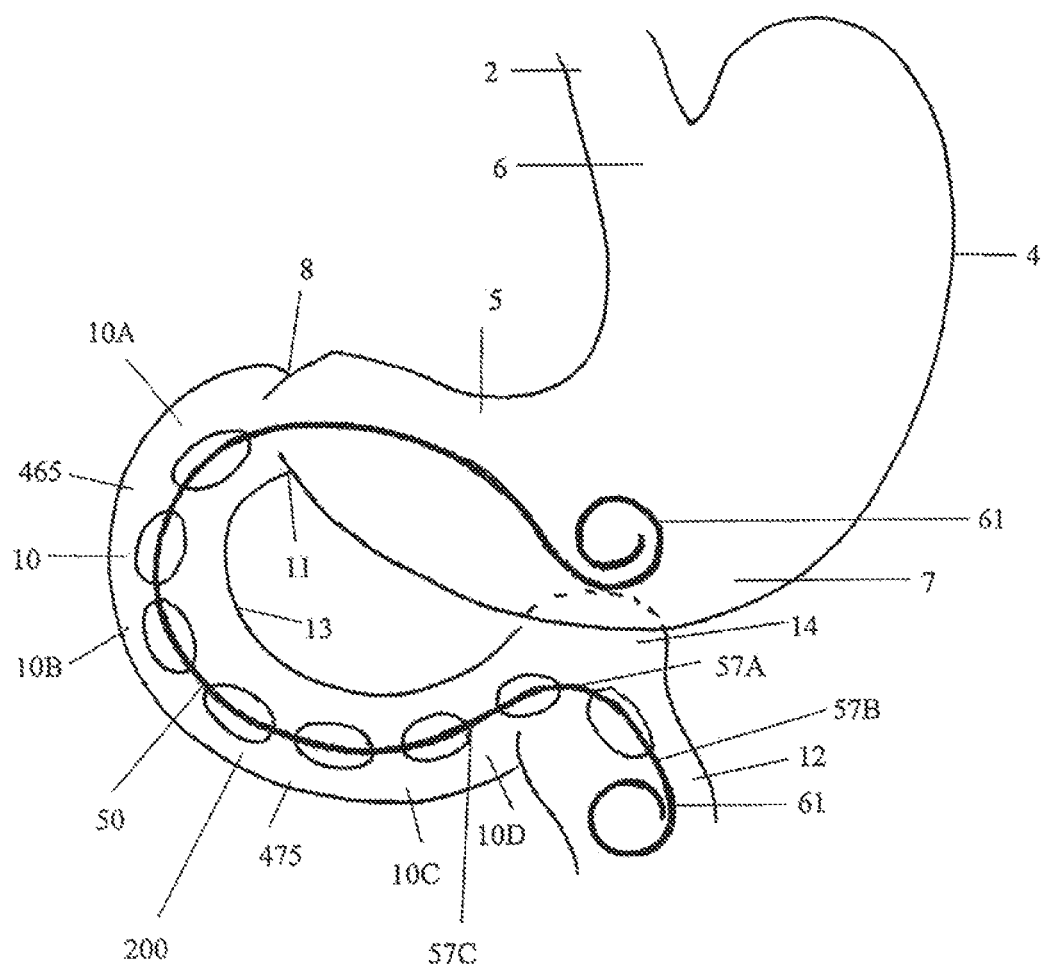
FIG. 22 shows a section view of the stomach with a device implanted into the duodenum having an distal portion extending into the jejunum.

FIG. 22 provides a section view distal esophagus, stomach, duodenum and proximal jujunem having a device with a distal portion in residence at the site of the duodenojejunal flexure 14. The device is curvilinear with an angle that conforms at least partially to the flexure 14 and a distal end that extends beyond the flexure 14 to an atraumatic distal end 61 disposed within the jejunum 12. FIG. 22 illustrates a device having a proximal end within the stomach and beyond the pylorus as in FIG. 76. The illustrated embodiment has proximal and distal terminal ends each having a coiled feature 61 as described above. The distal portion of the device includes an inflection point 57A representing the change in curvature of the spine 50 from the proximal region 57B to the distal region 57C. In the illustrated embodiment, the inflection point 57A and regions 57B, 57B form a radius of curvature conforming to or approximating the curvature of the gastrointestinal tract in the transition from the ascending duodenum 10D to the jejunum 12 along the duodenojejunal flexure 14. A plurality of flow reduction elements 200 are illustrated along the spine 50. The flow reduction elements are shown along the length of the device from portion within the duodenal bulb 10A to the distal portion 20D within the jejunum 12. The flow reduction elements 200 may vary from the illustrated embodiment. The flow reduction elements 200 may take the shape, size, construction, orientation or any attribute of the flow reduction elements described herein.

Figure 23:
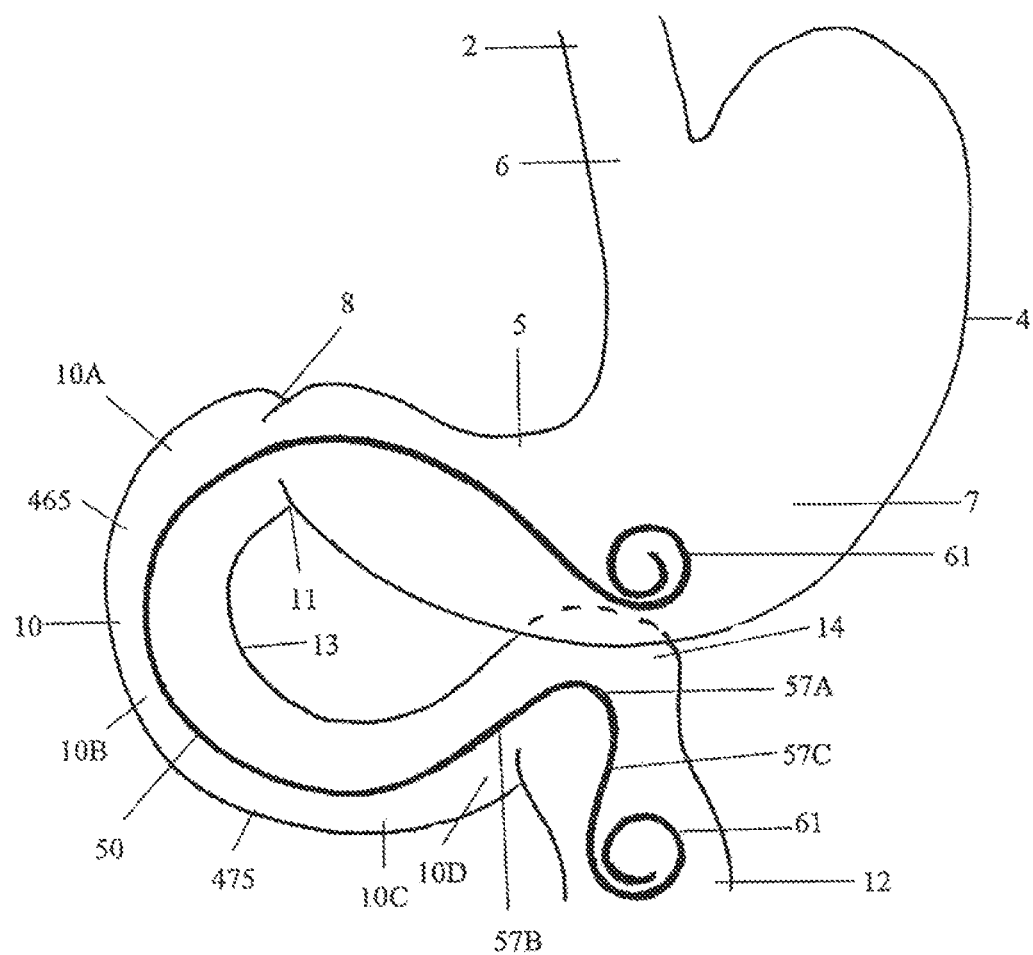
FIG. 23 shows a section view of the stomach with a device implanted into the duodenum having an distal portion extending into the jejunum.

FIG. 23 provides a section view distal esophagus, stomach, duodenum and proximal jujunem having a device with an inflection point mimicking the duodenojejunal flexure 14. The distal portion of the device may conform in length or shape to the anatomy of the duodenum at the D-J flexure 14. In another aspect, the device is curvilinear with an angle that conforms at least partially to the flexure 14 and a distal end that extends beyond the flexure 14 to an atraumatic distal end 61 disposed within the jejunum 12. FIG. 23 illustrates a device having a proximal end within the stomach and beyond the pylorus as in FIG. 76. The illustrated embodiment has proximal and distal terminal ends each having a coiled feature 61 as described above. The distal portion of the device includes an inflection point 57A representing the change in curvature of the spine 50 from the proximal region 57B to the distal region 57C. In the illustrated embodiment, the inflection point 57A and regions 57B, 57B form a radius of curvature conforming to or approximating the curvature of the gastrointestinal tract in the transition from the ascending duodenum 10D to the jejunum 12 along the duodenojejunal flexure 14. The inflection point 57A in FIG. 23 represents a tighter radius than in FIG. 22. The inflection point 57A in FIG. 23 may vary from the illustrated embodiment to more closely conform to the angle of the duodenojejunal flexure 14, be smaller (i.e., tighter radius) or larger (i.e., larger radius) than that of the natural duodenojejunal flexure 14.

Devices with Anchoring Member in Stomach

Anchoring members that reside in the stomach and are too large to be swept through the pylorus can be used with any of the devices described herein and/or with any device having a portion that extends distal to the pylorus.

Basic Anchor Designs

Figure 7:
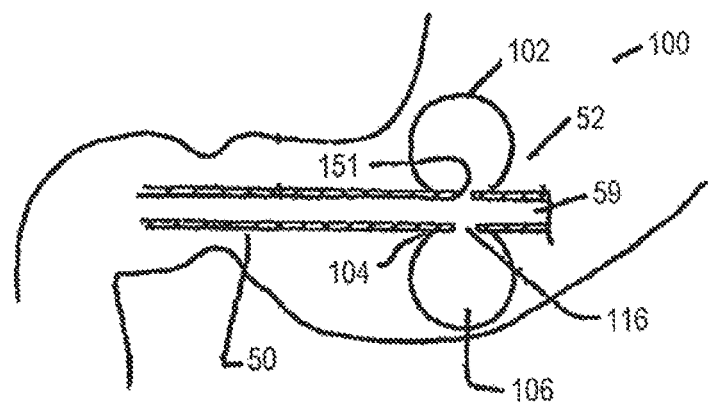
FIG. 7 is a perspective section view of a central tube and an anchoring member.

FIG. 7 depicts one such anchoring mechanism. In FIG. 7, the central tube 50 has an anchoring member 100 near its proximal end 52. The anchoring member 100 may be established by one or more inflatable balloons 102 positioned in the proximal end 52 of the device. These balloons 102 may be eccentrically attached to the central tube at point 104 near the proximal end 52 of the central tube 50. These balloons may be formed in many shapes and are not limited to the spherical shape shown. The central tube may be formed with an opening 116 for each respective balloon 102 so that a pathway for fluid communication is established between the inner lumen 59 of the central tube 50 and the inner space of each balloon 106. The inner lumen 59 is used to introduce fluid into the inner space of the balloon 106 and inflate the balloon 102 from a first volume in a collapsed state to a second volume or inflated state. When the one or more balloons 102 of the anchoring member 100 are fully inflated, they secure the proximal end of the central tube 52 such that it cannot pass through an adjacent orifice, such as the pylorus 8. The one or more inflatable balloons 102 have a combined cross sectional diameter greater than the diameter of the pyloric valve to prevent migration across the pylorus. The inflatable balloons 102 may be inflated and deflated by adding or removing fluid from the central tube inner lumen 59. The inflatable balloons 102 may be connected to the same central tube inner lumen 59 as the one or more flow reduction elements attached to the central tube and may be inflated simultaneously with the flow reduction elements. The central tube 50 may also have more than one inner lumen so that the inflatable balloons 102 and individual one or more flow reduction elements may be inflated and deflated independently as well.

Figure 8:
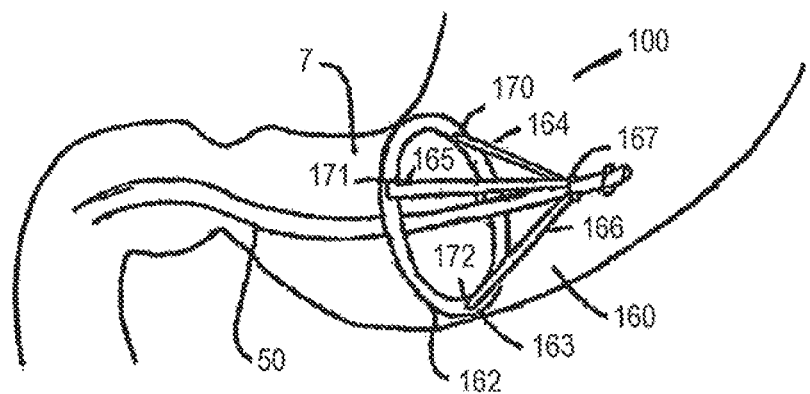
FIG. 8 is a perspective view of an alternative embodiment of a central tube and an anchoring member.

FIG. 8 illustrates another embodiment of the invention, wherein an anchoring member 100 of the present invention is deployed in the antrum 7. In this embodiment, a central tube 50 is attached to an inverted umbrella skeleton 160. This skeleton 160 has a ring 162 that surrounds the central tube 50 and is supported by struts. In the depicted embodiment the ring 162 is supported by three struts 164, 165, and 166, however more or fewer struts may be successfully employed. In the embodiment depicted in FIG. 8, the struts are joined together at the central tube 50 at point 167 and attached to the ring 162 at points 170, 171 and 172. The ring 162 of this anchor configuration may be made from, by way of example, flexible plastic material or flexible wire and has a diameter significantly larger than the diameter of the pyloric valve. This umbrella skeleton 160 may be collapsed around the central tube 50 for insertion into the stomach with the aid of an endoscope. As the device is released from the endoscope, the umbrella skeleton 160 may spring out and assume a configuration similar to that shown in FIG. 8. The struts 164, 165 and 166 may be made from, by way of example, plastic, metal or from plastic covered metal. The edge of the ring which is in contact with the antrum walls 163, may be constructed to assist in securing the umbrella ring 162 to the walls of the antrum.

Figure 24:
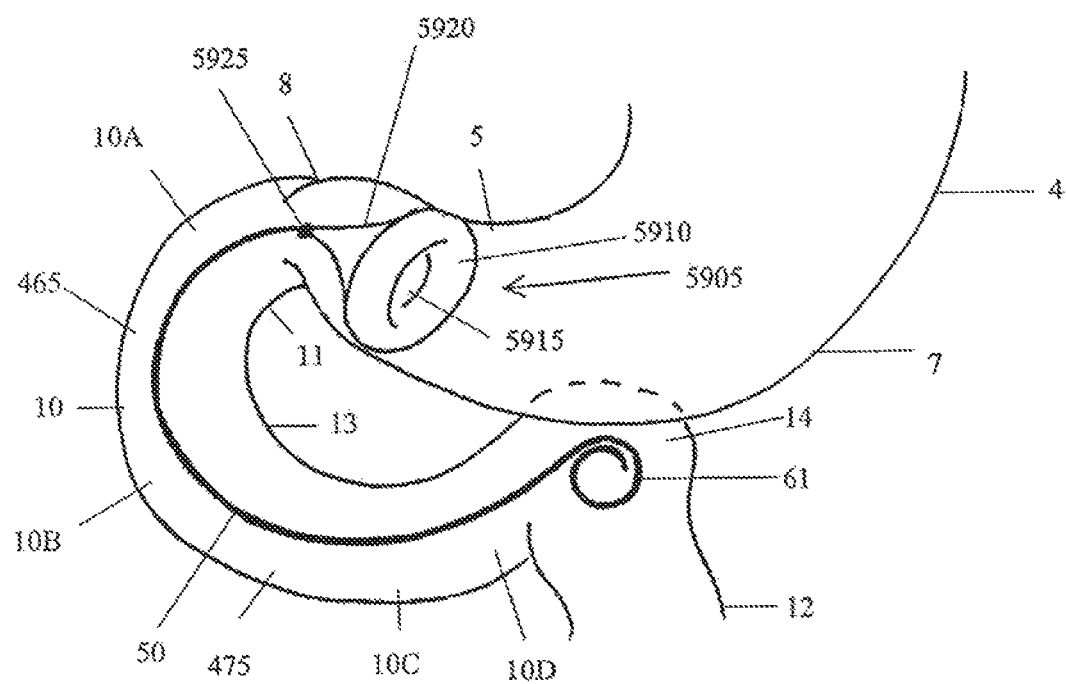
FIG. 24 shows a section view of the stomach with a device implanted into the duodenum having an proximal ring shaped anchor.

FIG. 24 provides a section view of the distal esophagus, stomach, duodenum & proximal jujunem having a device that illustrates another embodiment of the invention, wherein an anchoring member 5905 of the present invention is deployed in the antrum 7. The anchoring member 5905 includes a base 5910 with an opening 5915 and one or more lines 5920. The one or more lines 5920 are used to attach the base 5910 to the spine 50 at or near its proximal end via attachment point 5925. In one alternative, instead of lines 5920, a cone or funnel is used to attach a base 5910 to the spine 50. The cone or funnel could be made of a solid sheet of material or a mesh. The remainder of the spine 50 and distal end may take any of the different configurations described herein. The base 5910 has a perimeter sized so as to remain within the antrum and/or not pass through the pylorus with an open middle portion 5915 to allow food to pass. The base 5910 may be of any open shape such as circular, oval, oblong, rectangular and the like. In the illustrated embodiment, the base 5910 is a ring. In an additional aspect, the anchoring member 5905 may include a valve to further meter the flow of food therethrough. The anchoring member 5905 may be made of a biocompatible polymer. The anchoring member 5905 may be completely or at least partially hollow. The hollow portions of the anchoring member 5905 may be filled with air or a fluid. A hollow anchoring member 5905 may be advanced to the implant site in a stowed or uninflated configuration and then filled into a deployed configuration once placed in the implant site.

In an alternative configuration of FIG. 24, anchoring member 5905 may be formed of a ring made of a stiff material, such as metal, to prevent collapse from peristalsis. In another aspect, the anchoring member 5905 could be a frame or scaffold structure that collapses for delivery and then springs into shape upon delivery. In one aspect, the anchoring member 5905 may be shaped like an inverted umbrella skeleton with a ring supported by struts as shown and described above in FIG. 8. The components of the anchor member 5905 may be made from, by way of example, flexible plastic material or flexible wire and has a diameter significantly larger than the diameter of the pyloric valve. The anchoring member 5905 may be collapsed around the spine 50 for insertion into the stomach and duodenum with the aid of an endoscope. As the device is released from the endoscope, the anchoring member 5905 may spring out and assume a configuration similar to that shown in FIG. 24 or achieve such configurations after suitable inflation. The one or more lines or struts 5920 may be made from, by way of example, plastic, metal or from plastic covered metal. In another aspect, the edge of the ring 5910 which is in contact with the stomach walls, may be constructed to assist in securing the anchoring member 5905 to the stomach walls such as thorough the use of hooks, barbs, coils or other piercing or penetrating devices.

Expandable Proximal Anchors

FIGS. 30-34 illustrate various alternative expandable proximal anchor embodiments. These anchor embodiments are adapted and configured to—once deployed into the stomach—provide a large enough structure that will prevent passage of the anchor through the pylorus. The spine and distal anchor in each of these embodiments is illustrated in a minimal way so as to not distract from the additional details being provided for the proximal anchor. As such, it is to be appreciated that any of the above described flow reduction elements, sleeves, features, characteristics, qualities or capabilities of the duodenal based treatment devices described herein may be used in conjunction with the proximal anchors described herein. Additionally or alternatively, FIGS. 30-34 may be used with any of the above described duodenal devices.

Figure 30A:
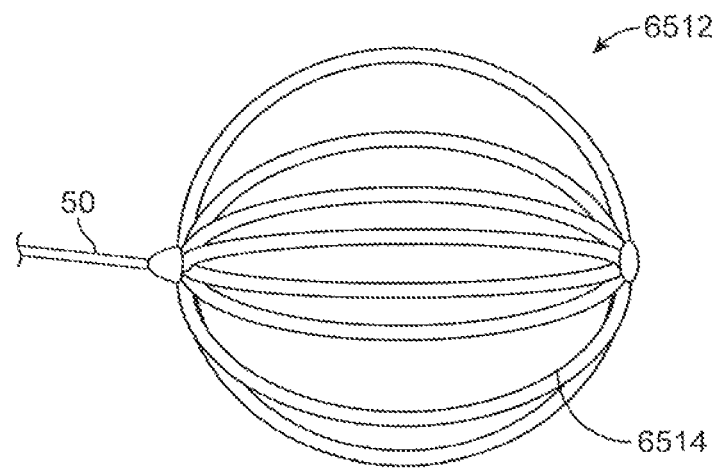
FIGS. 30A-30B illustrate a device with a proximal anchor formed from a multiple strand ball in a deployed and stowed configuration, respectively.
Figure 30B:
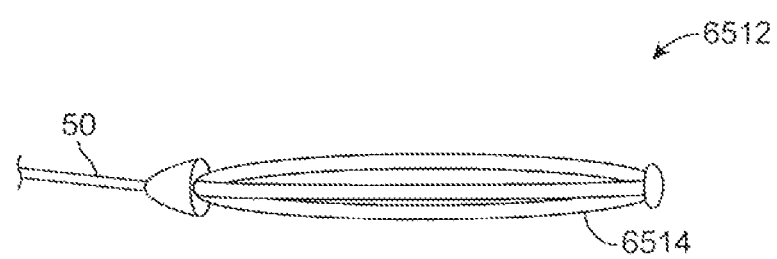

FIGS. 30A-30B show an embodiment of one proximal anchor mechanism. The proximal anchor mechanism can include a ball 6512. The ball 6512 can include a plurality of struts 6514 configured to expand. For example, the struts 6514 can extend longitudinally from the spine and approximately parallel to one another. The struts 6514 can then be configured to expand outwards to form the ball 6512, as shown in FIG. 30A. For example, the struts 6514 can be formed of a shape-memory alloy, such as Nitinol, so that the struts can expand into a preformed shape after delivery. The struts 6514 can thus be thin and/or flexible to allow collapse and expansion without requiring too much force and/or without causing damage to the struts 6614. Further, while the ball 6512 is shown as substantially spherical, it could also take other shapes, such as an oblong shape.

Referring still to FIGS. 30A and 3013, the struts 6514 can be unfinished, polished or, alternatively covered by a thin membrane, such as a thin fabric or polymer, e.g., ePTFE, silicone, or polyurethane. The thin membrane can be sewed or otherwise secured onto the struts themselves or dip-coated directly onto the struts such that a ball 6512 is formed in its expanded state. As such, it is to be appreciated that the covering can be applied so that each individual strut may behave as described herein or that the ball formed by a plurality of struts has the characteristics described herein. By covering the struts 6514 with a thin membrane, the struts alone or together forming the ball 6512 can provide an enclosed hollow space, providing a reservoir for gases, such as air or $CO_2$, a fluid, such as water or saline, hydrogels, or bio-absorbable drug compounds that could be advantageous upon delivery. The thin membrane can be impenetrable, disallowing escape of gases or liquids, or penetrable, allowing materials therein to escape over time.

In one aspect, the inflatable structure (i.e., the strut, a ball or a combination thereof) may be filled with a selected material to bulk up the strut and/or ball in order to enhance the anchoring characteristics of the device. Additionally or alternatively, the filling material and membrane may be selected to maintain a fill amount but also to leak out the filling material over time. This time release aspect of the membrane and filler material permits the anchor to act as a drug delivery device by selecting therapeutically active ingredients as the filler material. Moreover, the particular membrane may be selected to permit passage of the filler material at a set rate of osmosis or permissive leaking.

In one embodiment, the thin membrane is a self-sealing substance that seals in situ over time. In one exemplary embodiment, the self-sealing compound is a layer of silicone. The silicone layer may general be thinner over the strut or ball but then a thicker area is used for insertion of a needle or other suitable filling device that pierces the silicone membrane and permits refilling. The thickness of the silicone layer in this area is selected so that upon withdrawal of the filling device tip, the silicone layer closes up to maintain a suitable pressure tight seal. If a self-sealing substance is used, periodic injections could be used to fill or refill the ball with a material throughout the in situ dwell period. In another aspect, the struts or ball may have a valve or sealing area to permit periodic refilling. Various hollow lumens and internal ports and other filling techniques described above in FIGS. 3, 4 and 5 may also be applied to the struts and/or ball.

Figure 31A:
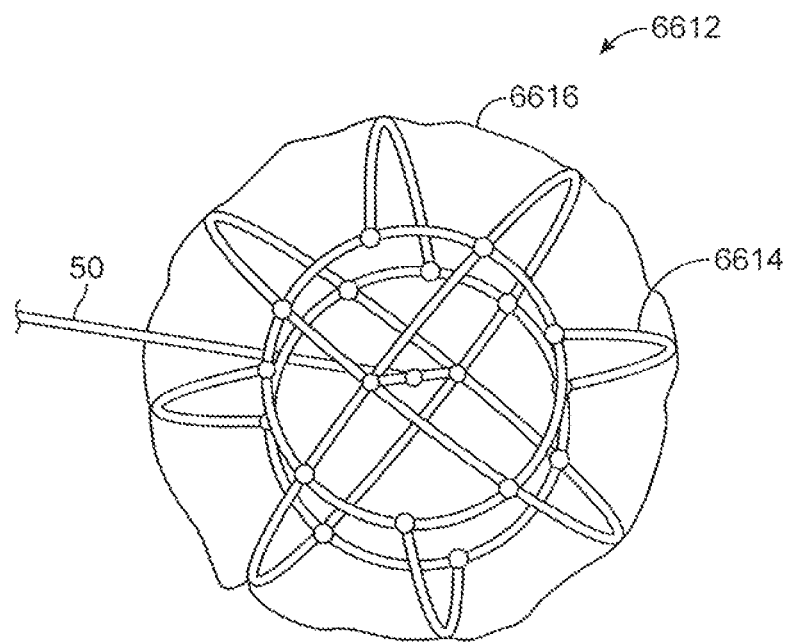
FIGS. 31A-31B illustrate a device with a proximal anchor formed from a multiple strand ball with a membrane coating in a deployed and stowed configuration, respectively.
Figure 31B:
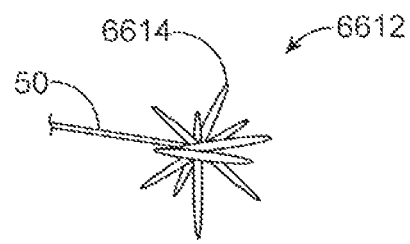

FIGS. 31A-31B show a proximal anchor, similar to the embodiment of FIGS. 30A-30B, having a ball 6612 formed of struts 6614 that expand from a collapsed configuration (FIG. 31B) to an expanded configuration (FIG. 31A). The struts 6614 can be combined in such a way that the ball 6612 expands both laterally and radially upon deployment. Similar to the embodiment of FIGS. 30A-3013, the ball 6612 can include a membrane 6616 thereon to provide an enclosure within the ball 6612.

Looped Wire Anchors

FIGS. 25, 32-35, and 45-50 show devices having proximal anchors formed from looped wires. The looped wires of the devices shown in FIGS. 25, 32-35, and 45-50 can straighten for delivery through a standard delivery tube and can be configured to resume or be forced into the looped shape once deployed in the stomach. The devices of FIGS. 25, 32-35, and 45-50 can further be collapsed or straightened once deployed for removal from the stomach through a standard tube.

Figure 25:
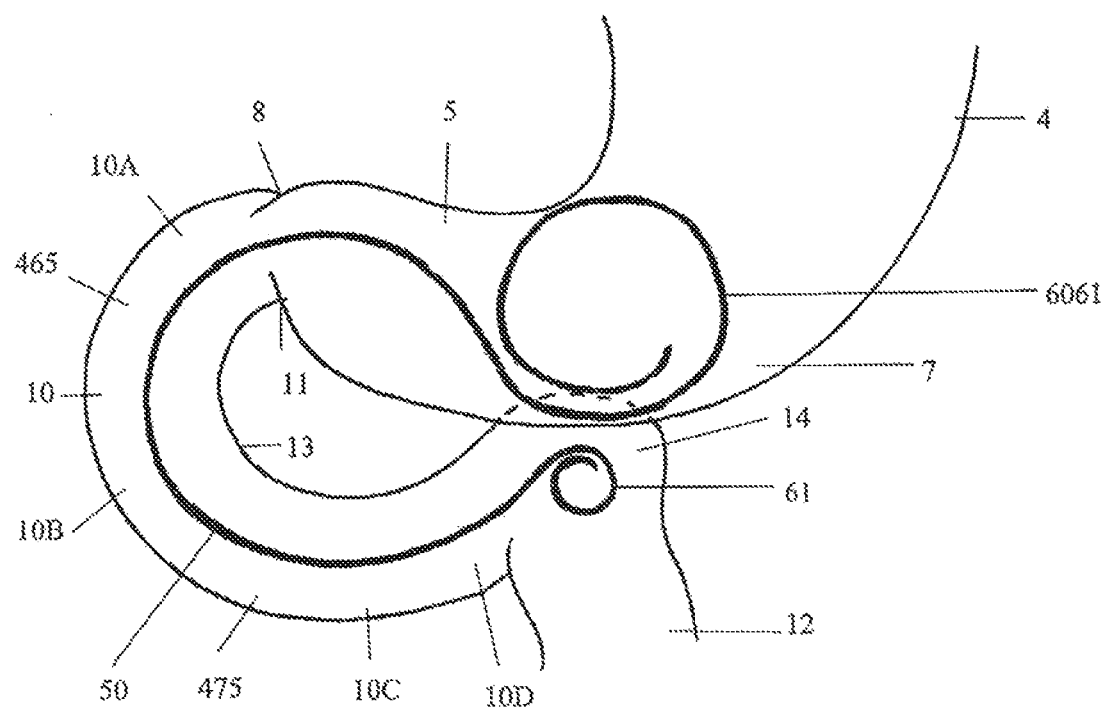
FIG. 25 shows a section view of the stomach with a device implanted into the duodenum having an enlarged proximal coil.

FIG. 25 provides a section view of a device having a looped proximal anchor 6061 on the proximal end that is different than the diameter and/or radius of curvature of the coil 61 (or other terminus) on the distal end. As shown in FIG. 25, the coil can extend in-plane with the spine 50. The coil can have a diameter that is larger than the diameter of the pylorus 5. The large diameter of the coil 6061 can advantageously help prevent the coil from being pulled into the pylorus and can thus help anchor the device in the GI tract. As shown in FIG. 25, the coil 6061 can be formed as a spiral that extends from the spine 50 and curves inwards. In some embodiments, the coil can be a continuous extension of the spine 50.

The coil 6061 may be formed by a nearly complete coil (i.e., less than one complete loop), a complete loop or more than one loop—having an overlapping portion of all or part of additional turns of a coil. In some embodiments, the diameter of the proximal coil 6061 may be sized to cover a span determined by the interior dimensions of the stomach. In one embodiment, the diameter of the coil is large enough to extend across a portion of the stomach on the lesser curvature to a portion on the greater curvature. In still another aspect, the coil is from different radius of curvature or from turns with different diameters.

In other embodiments, the coil 6061 may form into spiral or helical shapes or shapes that are out of plane with other turns of the coil or with the device. Still further embodiments have the proximal coil oriented in a vertical orientation within the stomach, a horizontal orientation in the stomach or in combinations thereof.

The characteristics, qualities and dimensions including the cross section shape of the spine of FIG. 25 may be modified in order to adapt the spine to the particular properties desired based on the residence site for the coil 6061.

Figure 45:
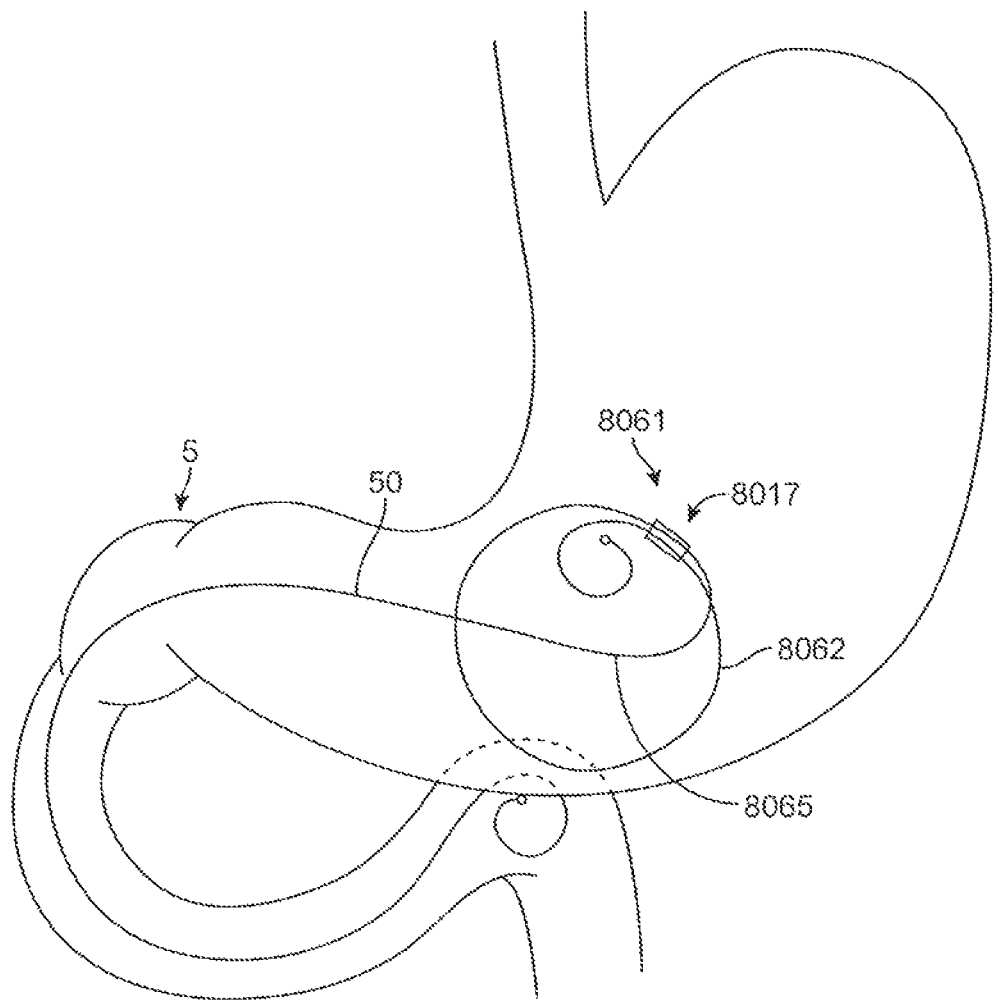
FIG. 45 shows an exemplary looped proximal anchor in place in the gastrointestinal tract.

In one embodiment, referring to FIG. 45, a looped proximal anchor 8061 includes a coil 8062. Similar to the anchor of the embodiment of FIG. 25, the coil 8062 can extend in-plane with the spine 50 and can have a diameter that is larger than the diameter of the pylorus 5, which can advantageously help prevent the anchor 8061 from being pulled into the pylorus and can thus help anchor the device in the gastrointestinal tract. In contrast to the embodiment of FIG. 25, however, the anchor 8061 can include a stem 8065 that extends from the spine 50 and then curves around to form the coil 8062. The coil 8062 can extend around the stem 8065 such that the stem 8065 runs through, i.e., substantially in the center of, the coil 8062. Having the stem 8065 advantageously provides a centering and stabilizing mechanism for the anchor 8061 when pulled distally by the pylorus. That is, as the spine 50 and thus the stem 8065 are pulled proximally, the coil 8062 will press up against the stem 8065, making it difficult for the coil 8062 to unwind and pull through the pylorus 5. Further, in some embodiments, a locking mechanism 8017, similar to any of the locking mechanisms described above, can be used to hold the shape of the coil 8062.

The coil 8062 can be formed by less than a complete loop, a complete loop, or more than one loop with an overlapping portion. In some embodiments, the coil 8062 is oriented in a vertical orientation within the stomach, a horizontal orientation within the stomach, or a combination thereof. Further, the spine 50 can be modified to include any of the properties described above, such as a sleeve, flow reduction elements, etc.

Figure 32A:
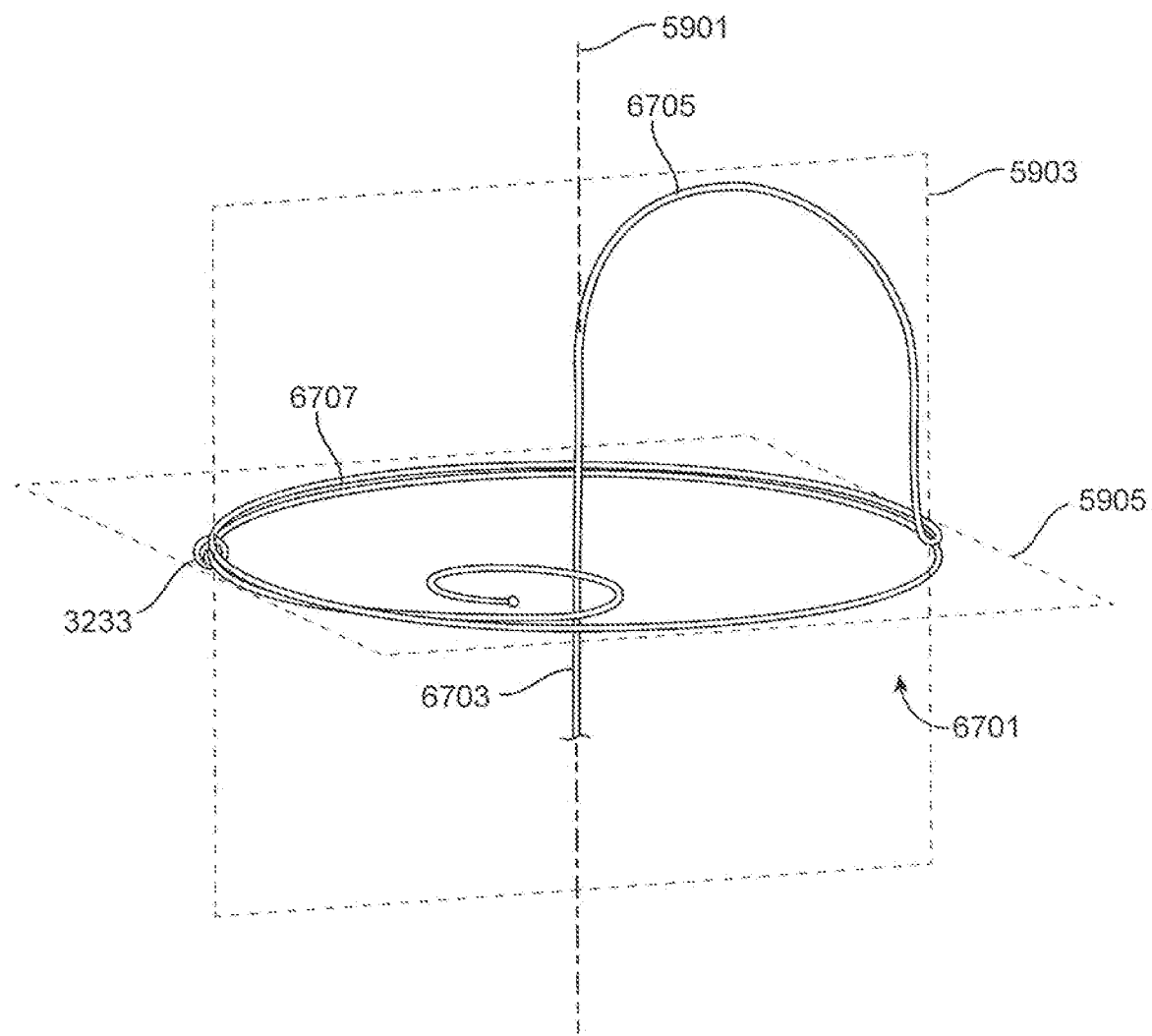
FIGS. 32A, 32B and 32C are various views of a proximal anchor embodiment having a stem, a single arch, a coil and terminating in a curved or coiled section.
Figure 32B:
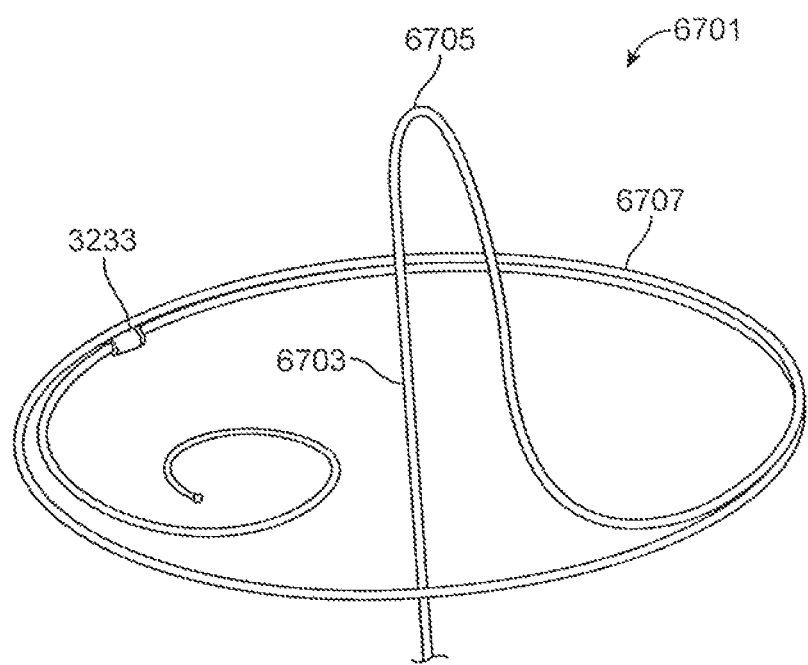
Figure 32C:
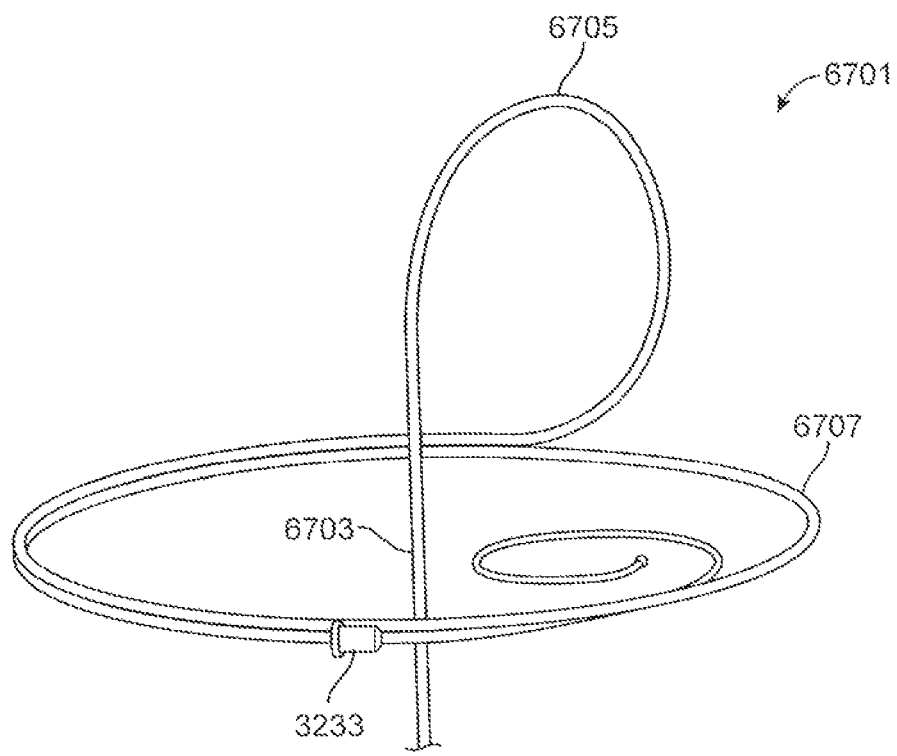
Figure 33:
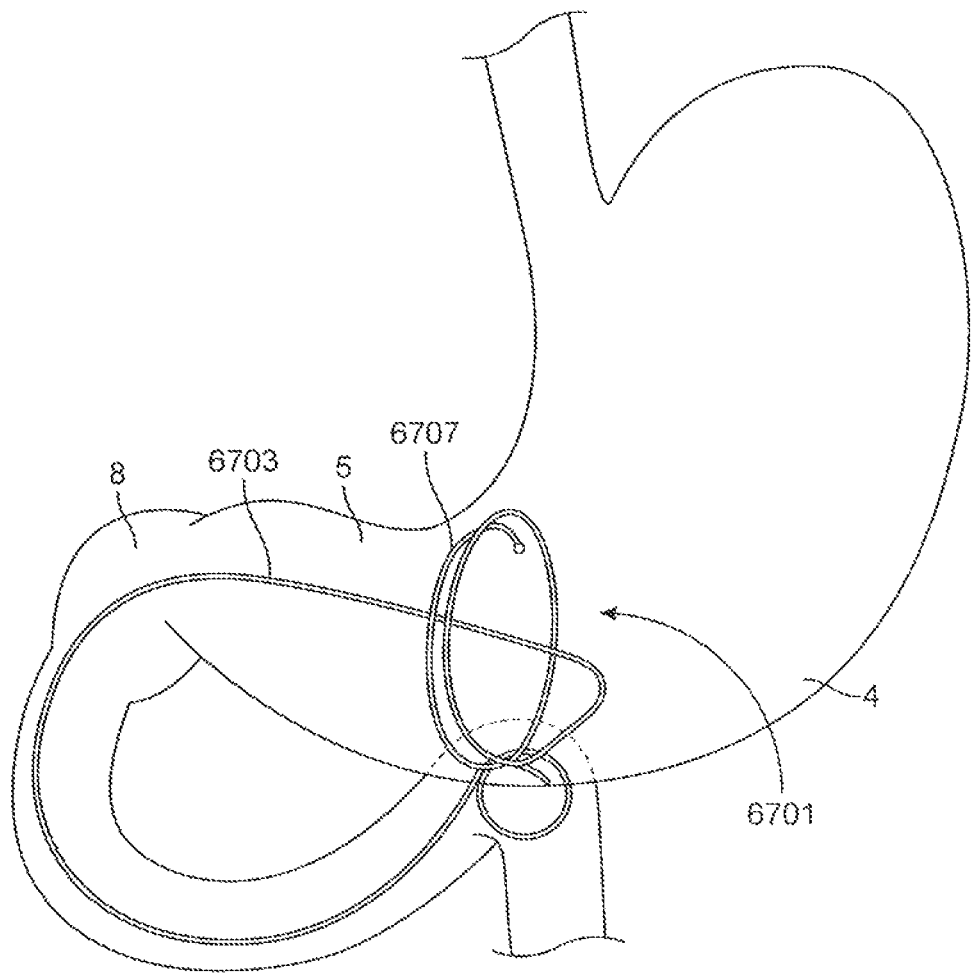
FIG. 33 is a cross section view of the stomach with a device having a stem, arch and coils similar to FIGS. 32A-32C with the substitution of a bulbous terminal end instead of or in addition to the small coiled end of FIGS. 32A-32C.

FIGS. 32A-33 shows an embodiment of a proximal anchoring member 6701. The anchoring member 6701 can include a stem 6703 extending axially with the spine, an arch 6705 extending radially away from the stem 6703, and a coil 6707 extending annularly or at least partially around the stem 6703, i.e., perpendicular to the stein 6703. As shown in FIGS. 32A-32B, the arch 6705 can connect the coil 6707 with the stem 6703. The stem 6703, arch 6705, and coil 6705, can be formed of a single unitary elongate body, such as a piece of wire.

The stein 6703 can have a diameter of less than 0.0050 inches, such as between 0.025 inches to 0.050 inches, such as between 0.035 inches to 0.043 inches. Further, as shown in FIGS. 32A-32C, in some embodiments, the stem 6703 can have a diameter that is the same as the diameter of the spine. In some embodiments, the spine and stem 6703 along with the intervening coil and arch can be formed of a continuous piece of wire. In some embodiments, the diameter of the wire used for the stem, the arch, the coil or coils and the spine is about the same. In an alternative embodiment, the coils and the spine have the same wire diameter that is smaller than the wire diameter of the arch and the stem. In still another embodiment, the wire diameter of the stem is larger than the wire diameter of the arch as well as the coils and the spine. In still another aspect, the diameter of the wire formed into the coils is different in each of the coils. In addition to the representative wire diameters for the stem above, representative wire diameters for the other portions of the device include for example, the arch ranging from about 0.025 inches to about 0.035 inches; the coil or coils ranging from about 0.035 to about 0.040 inches and the spine ranging from about 0.035 to about 0.045 inches.

As shown in FIGS. 32A-33, the arch can extend both longitudinally and radially away from the stem 6703. This arching form can advantageously provide additional hoop strength in helping to center the coil when it is pushed or compressed from the side. The transition of the arch to the coil can further provide an "interlock" if the coil 6707 moves proximally with respect to the stem 6703 when in situ. This interlock would engage if the arch transition is flared outside the coil diameter or if the coil diameter is smaller than the arch transition. Further, having an arched configuration can provide a smooth and seamless transition when straightening the anchor 6701 for delivery. To defeat the interlock feature, the arch needs to be slightly squeezed together as the coil is pulled proximally over it in a straightening manner. Finally, the arch 6705 form a simple retraction loop should the device need to be removed from a patient after delivery. In an alternative embodiment, the arch 6705 can be replaced with a connecting portion that extends substantially perpendicularly from the stem 6703 to the coil 6707. In this embodiment instead of an arc pathway from the stem to the perimeter coil the wire extends from the stem in a direct path to the coils while remaining generally in a plane containing the coils.

The coil 6707 can be formed by nearly a complete loop, a complete loop, or more than one loop, i.e., having an overlapping portion of all or part of additional turns of a loop. Thus, the coil 6707 can be formed of approximately 1 loop to 4 loops, such as 1 loop to 2 loops. For example, as shown in FIGS. 32A-32B, the coil 6707 can include approximately 1.5 loops. Having more than one loop can advantageously provide increased cumulative hoop strength of the coil 6707 without increasing the stiffness of the wire making up the coil 6707. Keeping a low stiffness of the wire can advantageously help with ease of straightening of the wire when inserting the device into the endoscope handle, decreased force during delivery and decrease damage to the tissue (tissue damage may occur if a wire is too stiff).

The coil 6707 can have a diameter such that, when placed in the stomach 4 perpendicular to the pylorus 5 (see FIG. 33), it is not able to pass through the pylorus 5. Thus, for example, the diameter of the coil 6707 can be between 3 cm and 20 cm, such as between 5 cm and 15 cm. The coil 6707 can end in an atraumatic end, such as a smaller coil as shown in FIGS. 32A-32C. Additionally or alternatively, the terminal end may have a slightly enlarged bulbous end as shown in FIGS. 32A and 33, for example. A bulbous end as shown may be formed by directing a high-power laser on the end of the wire.

FIG. 32A also illustrates a shoulder or feature on one of the coils. This feature is positioned on the wire to provide a connection point for an insertion or device delivery. While shown on the lower coil at about the 9 o'clock position, this location is for purposes of example. The shoulder feature may be placed in a wide variety of locations depending upon a number of factors such as the insertion device used or the specific design parameters of the anchor. The feature may be a short cylinder attached to the wire at a suitable location.

The proximal anchor 6701 can be preshaped to take the expanded configuration shown in FIGS. 32A-32C. For example, the proximal anchor 6701 can be made of a shape-memory material such as Nitinol. Accordingly, the proximal anchor 6701 can be straightened for delivery, such as through an endoscope. The device can return to its preformed shape as it is released from the endoscope and then, as shown in FIG. 33, be fully released in the stomach 5. As shown in FIG. 33, the coil 6707 can be placed substantially perpendicular to the pylorus 8. The perpendicular placement of the coil 6707 ensures that, even if the pylorus 8 stretches out to form an oblong shape, it cannot stretch enough to allow passage of the coil 6707. Further, the thin diameter of the stem 6703 advantageously ensures that the pylorus 8 is able to grab ahold of as little of the device as possible. Finally, the sudden transition from the thin stem 6703 to the large diameter coil 6707 can provide a solid stop or shoulder that helps to further prevent the anchor 6701 from migrating through the pylorus 8, i.e., because the entire diameter of the coil 6707 can work to spread out the forces from the pylorus 8. Further, the coil 6707 of the anchor 6701 can be configured to sit proximally away from the pylorus 8, such as inside the antrum 5 or proximal to the antrum 5, to avoid undesirable and constant contact with the pylorus 8, such as to avoid irritation. In one aspect, the combination of stem length, arch bending radius and overall diameter of the coils are such that irritation of the pylorus may be reduced or minimized during use. Variations in the relationship of these elements may be used to alter the orientation of the device within the stomach as well as in relation to the pylorus. The placement of the anchor 2701 can also advantageously place the spine in the desired location for effective treatment based upon the specific configuration of the flow reduction element or devices arranged along the spine for positioning within or along the duodenum as described herein.

FIGS. 31A-34C illustrate proximal anchor 6901 similar to the proximal anchor 6701 of FIGS. 32A-32C. The proximal anchor 6901, however, includes two arches 6905a, 6905b extending from the stem 6903. Each arch 6905a, 6905b includes a corresponding coil 6907a, 6907b. The resulting two coils 6907a, 6907b are substantially aligned with one another to form a multi loop hoop structure 6917.

The arches 6905a, 6905b are configured to extend in substantially opposite radial directions. Having the arches 6905a, 6905b extend in substantially opposite radial directions advantageously provides a balancing force when stress is placed on the coils from a sideways direction 1907a, 1907b. That is, if there is only one arch, a lateral force may cause the arch to collapse radially inward. However, if there are two arches 6905a, 6905b extending in substantially opposite directions, then the two arches 6905a, 6905b can provide opposing inward forces on each other, thereby helping to keep the arches 6905a, 6905b in an upright position with the stem 6903 centered between the arches 6905a, 6905b.

The proximal anchor 6901 can include two portions 6912a, 6912b of wire extending parallel to one another into a single stein 6903. Each stem portion 6912a, 6912b can have a diameter of less than 0.0050 inches such that the diameter of the stem 6903 is less than 0.010 inches. The portions 6912a, 6912b can remain unattached along a substantial portion or all of the length of the stem 6903 except a portion used for joining by welding, brazing, crimping or other suitable process. A suitable length of weld may range from about 2.5 to about 10.0 mm. Alternatively, a spot weld or a plurality of spot welds may be used to join multiple wires (e.g., two or three wires) to form the central stem portion of the device. Keeping the majority of the portions of the anchor 6912a, 6912b unattached can advantageously provide flexibility for the anchor 6901 as various stresses are applied to the device during delivery and use in situ. An attachment point 6914 can mark where the spine transitions into the stem 6903, which can be distal of the coils 6907a, 6907b. By having the attachment point 6914 distal of the coils 6907a, 6907b, the area of higher stress around the coils 6907a, 6907b can be avoided, thereby avoiding potential snapping at the attachment point 6914.

Figure 34A:
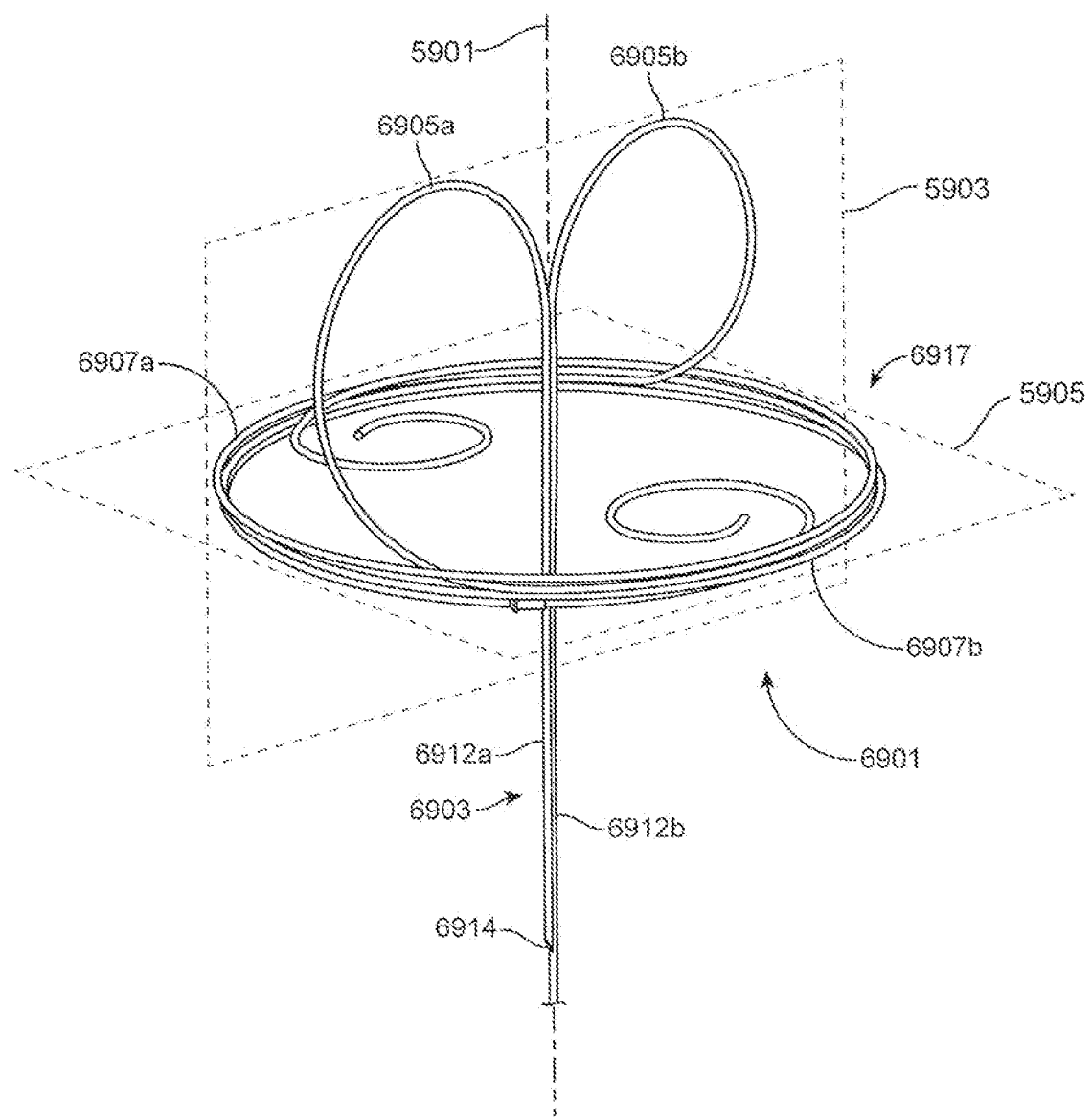
FIGS. 34A, 34B and 34C are various views of a proximal anchor embodiment having a dual shaft stein and a pair of arches leading to counter wound coils.
Figure 34B:
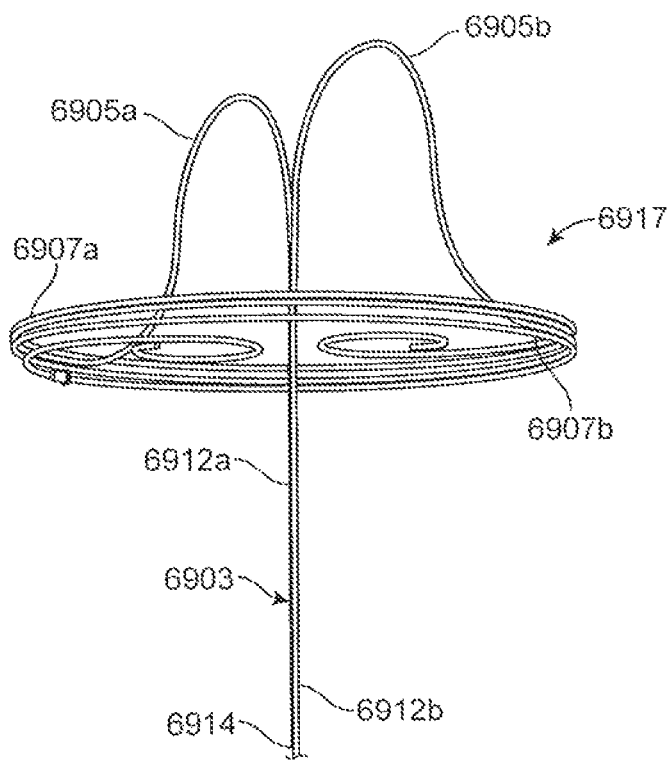
Figure 34C:
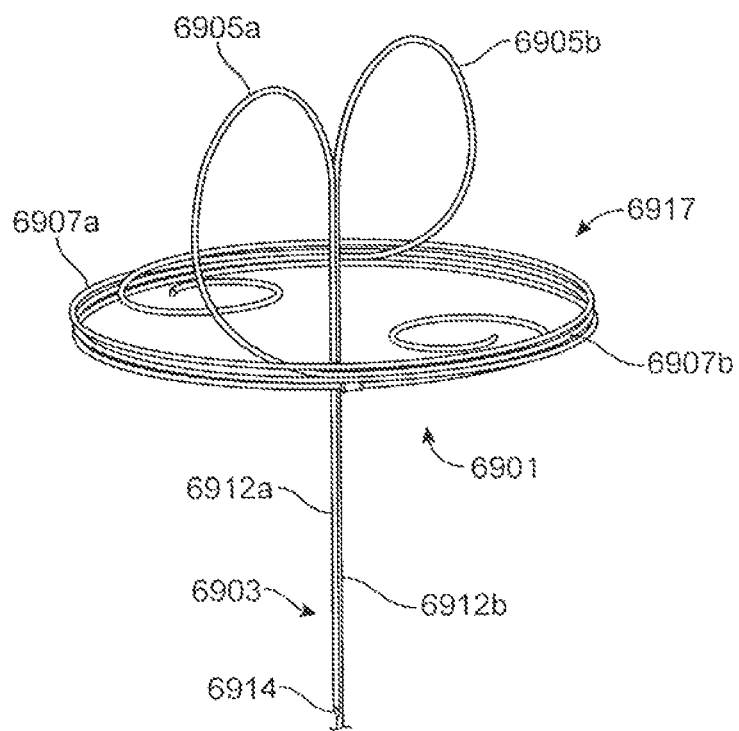

As shown in FIGS. 34A-34C, the coils 6907a, 6907b of the proximal anchor 6901 can both extend in the same direction, such as counterclockwise. In another embodiment, the coils 6907a, 6907b could extend in opposite directions. Each coil 6907a, 6907b can be formed by nearly a complete loop, a complete loop, or more than one loop, i.e., having an overlapping portion of all or part of additional turns of a loop. Thus, each coil 6907a, 6907b can be formed of approximately 1 loop to 4 loops, such as 1 loop to 2 loops. For example, as shown in FIGS. 32A-32B, each coil 6907a, 6907b can include approximately 1.5 loops. Further, the coils 6907a, 6907b can be configured to start and end such that a thickness of the entire hoop structure 6917 is substantially equivalent all the way around the diameter, e.g., there are approximately 3 loops at each point along the diameter of the hoops structure 6917.

In a still further alternative, there may be three separate wires joined into a common, central stem with three arches spaces equidistantly about 120 degrees part then into coils of suitable number as described elsewhere. The winding of the three separate coils may be all the same direction or alternating directions. For example, the top and bottom coils may be wound in counter clockwise fashion and the middle coil wound in clockwise fashion. Other alternative winding orientations are possible. In other embodiments, a proximal anchor can include more than three arches and corresponding coils are possible, such as 4 or 5 arches, each with its own corresponding coil.

The elongate body can be preshaped to take the expanded configuration shown in FIGS. 34A-34C. For example, the elongate body can be made of a shape-memory material such as Nitinol. Accordingly, the proximal anchor 6901 can be configured to be straightened for delivery, such as through an endoscope. In order to effectively straighten the device, the two arches 6905a, 6905b can be brought together, e.g., one of the arches 6905a, 6905b can be pulled 180° or both arches can be pulled approximately 90° to meet in the middle. By aligning the arches 6905a, 6905b with one another, the coils 6907a, 6907b can be pulled around and over the arches 6905a, 6905b, thereby unraveling the coils 6907a, 6907b and straightening the entire anchor 6901.

It is to be appreciated that there a plurality of recovery modes for the anchors described herein. Any one or a combination of these recovery modes or techniques can be used to collapse the stem-arch-coil anchor structure to permit removal from the implant location in the stomach. In one aspect, withdrawal of a component of the device refers generally to a movement away from the pylorus. One recovery mode is to grasp the arch and withdraw it away from the coil. Additionally or alternatively, the withdrawal action may be in a line generally parallel to the stem or, optionally, at a non-zero angle relative to the stem. This movement will then withdraw the coil and spine along with the stem. Another recovery mode involves first grasping one of the coils and withdrawing it. In a similar way, this action will unwind the remaining coils, collapse the arch or arches and permit the now unwound anchor to be withdrawn in unwound form along with the stem and spine. In still another form of recovery, the terminal end of the coil (i.e., the small ball tip or curved terminal end) is grasped and withdrawn generally away from the pylorus. This action will result in the coil being unwound and then the arch or arches following behind the stem and the spine. The proximal anchor 6901 can thus be configured to sit in or just proximal of the antrum similar to the proximal anchor 1701 shown in FIG. 33. Selection of the length of stem and arch allow for a wide variety of anchor placements. In addition, the selection of the overall diameter of the anchor (i.e., the diameter across the circumference formed by one or more of the coils) may also be chosen to assist in anchoring the device while also reducing or minimizing pyloric irritation by limiting contact with the pylorus to the stem.

FIGS. 35A-35D show another embodiment of a proximal anchoring member 7001. The anchoring member 7001 can include a stem 7003 extending axially from the spine, two arches 7005a,b extending radially away from the stem 7003, coils 7007a,b extending annularly or at least partially around and perpendicularly to the stem 7003, and a pull loop 7077 connected through the two arches 7005a,b and merging into the coils 7007a,b.

Each arch 7005a,b extends proximally from the stem 7003, curves through a proximal peak, and extends distally to merge into a respective coil 7007a,b. The arches 7005a,b can thus extend both longitudinally and radially away from the stem 7003. This arching form can advantageously provide hoop strength by helping to center the coils 7007a,b when the anchor 7001 is pushed or compressed from the side. In some embodiments, the arches 7005a,b extend further radially then the coils 7007a,b. The transition of the arches 7005a,b to the coils 7007a,b can provide an "interlock" when the stem 7003 moves distally in the pylorus relative to the coils 7007a,b, as the arches 7007a,b will be prevented from pulling through the coils 7007a,b.

The arches 7005a,b can both extend counterclockwise (from the proximal point of view) as they merge into the coils 7007a,b. Further, the arches 7005a,b are configured to extend in substantially opposite radial directions. Having the arches 7005a,b extend in substantially opposite radial directions advantageously enables the arches 7005a,b to behave as moment arms and assume approximately half of the imparted load in a balanced manner. This forces the load path to originate at the end of the virtual moment arm at the coils 7007a,b and travel through the arches 7005a,b to the central stem 7003 where they join. This equal and opposite load path balances the imparted load. As a result, the coils 7007a,b maintain an orthogonal orientation with respect to the stem 7003, resulting in a large span from one coil 7007a,b to the opposite, thereby creating a larger proximal anchor 7001. That is, the two arches 7005a,b can support each other, thereby helping to keep the arches 7005a,b in an upright (proximally-extending) position, the coils 7007a,b orthogonal to the stem 7003, and the stem 7003 centered between the arches. Having a centered stem 7003 advantageously reduces the likelihood of damage to the pylorus caused by the anchor 7001 being pushed off-center by muscular contractions.

The pull loop 7077 can include a loop portion 7076 that extends in between the arches 7005a,b as they meet at the stem 7003. Counterarch portions 7079a,b can extend from the loop portion 7076. A counterarch can extend substantially opposite to, or counter to, an arch, and can have a radius of curvature that is smaller than the radius of curvature formed by the coils and/or formed by a circle extending perpendicular to the stem and around the outermost portion of the arches. In this embodiment, each counterarch portion 7079a,b can extend from the loop portion 7076 to a respective coil 7007a,b. The peak of the counterarch portions 7079a,b can extend distally until it is approximately within the plane of the coils 7007a,b. The counterarch portions 7079a,b can extend in substantially opposite radial directions from one another. Further, the counterarch portions 7079a,b can have a peak that is approximately 90 degrees away from the peak of each arch 7005a,b (using the stem as a central axis). This placement at 90 degrees provides for approximately four supports—at every 90 degrees around the circumference of the anchor 7001—to stabilize the anchor 7001 and discourage proximal movement of the anchor 7001. The counterarch portions 7079a,b can both loop in a counterclockwise direction to connect to the coils 7007a,b. Thus, the counterarch portions 7079a,b can extend counterclockwise while the arches 7005a,b extend clockwise. In other embodiments, the arches 7005a,b can extend counterclockwise while the counterarches 7079 extend clockwise.

The arches 7005a,b can extend underneath (or distal to) the counterarches 7079a,b as they transition to the coils 7007a,b. This relative axial position of the arches 7005a,b and the counterarches 7079a,b provides additional interlocking and stability for the anchor 7001. This placement also facilitates collapse of the anchor 7071 when the pull loop is pulled in a proximal direction, as discussed further below.

In some embodiments, the stem 7003, arches 7005a,b, coils 7007a,b, spine and pull loop 7077 can be formed of a continuous piece of wire that is joined at the stem. Alternatively, the stem 7003, arches 7005a,b, coils 7007a,b, and/or spine can each be joined together using, for example, welding, crimping, gluing, soldering, sleeving or a combination of these.

The wire used for the stem 7003, arches 7005a,b, coils 7007a,b and spine, and pull loop 7077 can have the same or different diameters. The diameter of each can be between 0.01 to 0.06 inches, such as 0.016 to 0.050 inches, such as between about 0.018 to 0.044. In some embodiments, the diameters of the stem 7003, arches 7005a,b, coils 7007a,b and spine can be chosen to "tune" the wire to hold its shape with relatively greater or less force (by increasing or decreasing the wire's bending moment of inertia). For instance, the wire for the stem 7003 can be of a larger diameter than the coils 7007a,b and arches 7005a,b to resist deflection while the wire for the coils 7007a,b can be of a smaller diameter than the stem 7003 and arches 7005a,b to allow for flexing of the coils 7007a,b (minimizing stomach irritation). Likewise, the wire of the arches 7007a,b can have an even larger diameter than the wire of the stem 7003 and coils 7007a,b to increase stiffness and resist deformation and possible subsequent movement through the pylorus. The pull loop 7077 can have a relatively small diameter (see FIG. 35D), particularly near the loop portion 7076, to allow the anchor 7071 to be pulled into an endoscope, e.g., to allow the loop portion 7076 to collapse.

The interlock feature described above can be "unlocked" to remove the anchor 7001. To do so, the pull loop 7077 can act as a "handle" that can be pulled axially in a proximal direction with a retraction tool, such as a grasper, directly into the esophagus, into an endoscope working channel, into an overtube or into another device configured for removal. As the pull loop 7077 is pulled in a direction opposite the proximal anchor, anchoring member 7001 collapses radially inwards: the coils 7007a,b lift up and around the arches 7005a,b, until the arches straighten and collapse as well. The pull loop 7077 can be retracted into the endoscope working channel to initiate device removal. The coils 7007a,b and arches 7005a,b will then twist and collapse together in parallel fashion as they enter into the distal endoscope working channel. Collapse of the arches 7005a,b and coils 7007a,b is facilitated by exerting an opposing tension on the stem 7003 of the anchoring member 7001 as the pull loop 7077 is retracted into the endoscope.

For delivery, the interlock feature can likewise be "unlocked" by squeezing the arches 7005a,b together such that they are side-by-side to facilitate collapse of the proximal anchor for device collapse in the distal direction. This allows the coils 7007a,b to collapse and twist over the arches 7005a,b for entry into the endoscope working channel. The coils 7007a,b and arches 7005a,b can then self-expand or pop back into position after delivery.

The coils 7007a,b can take the form of a partial loop or more than one loop, i.e., having an overlapping portion of all or part of additional turns of a loop. Thus, each coil 7007a,b can be formed of approximately ½ loop to 4 or more loops. Having more than one loop can advantageously provide increased cumulative hoop strength of the coils 7007a,b without needing to increasing the diameter and therefore the stiffness of the wire making up the coils 7007a,b. Keeping a low stiffness of the wire has several advantages, including making it easier to straighten the wire for insertion into the endoscope working channel, decreased force during delivery, and decreased potential of damaging tissue (tissue damage may occur if a wire is too stiff). The coils 7007a,b can have a diameter such that, when placed in the stomach perpendicular to the pylorus, the anchor 7001 is not able to pass through the pylorus. Thus, for example, the diameter of the coils 7007a,b can be between 3 cm and 20 cm, preferentially between 5 cm and 15 cm.

In one embodiment, the shape of the wire is symmetrically mirrored in its path as followed up the stem 7003, through the arch 7005a,b, around the coil 7007a,b, up to the pull loop 7077, and then back down in a symmetric and opposite fashion to the other end of the wire at the junction with the stem 7003. By altering the symmetry of the path as it returns to the stem 7003 from the pull loop 7077, the wire can be made to take a more independent shape which can be advantageous to minimize the potential for tangling of equal and parallel features. For example, if the distal-most end of the wire has a 1.25 in diameter coil, and the medial section of wire has a 1.5 in diameter coil, the two coils will be less likely to nest into one another and tangle during insertion, delivery and removal with the pull loop. The amount of asymmetry can be low enough as to avoid unbalancing or substantially interfering with the performance of the anchor 7001.

The proximal anchoring member 7001 is adapted and configured to—once delivered through an endoscope and deployed into the stomach—expand to provide a large enough structure that will prevent passage of the anchor through the pylorus. The spine and distal anchor in FIGS. 35A-35D illustrated in a minimal way so as to not distract from the additional details being provided for the proximal anchor. As such, it is to be appreciated that any of the above described flow reduction elements, sleeves, features, characteristics, qualities or capabilities of the duodenal-based treatment device described herein may be used in conjunction with the proximal anchors described herein. Additionally or alternatively, the anchoring member 7001 may be used with any of the above described duodenal devices.

Figure 46A:
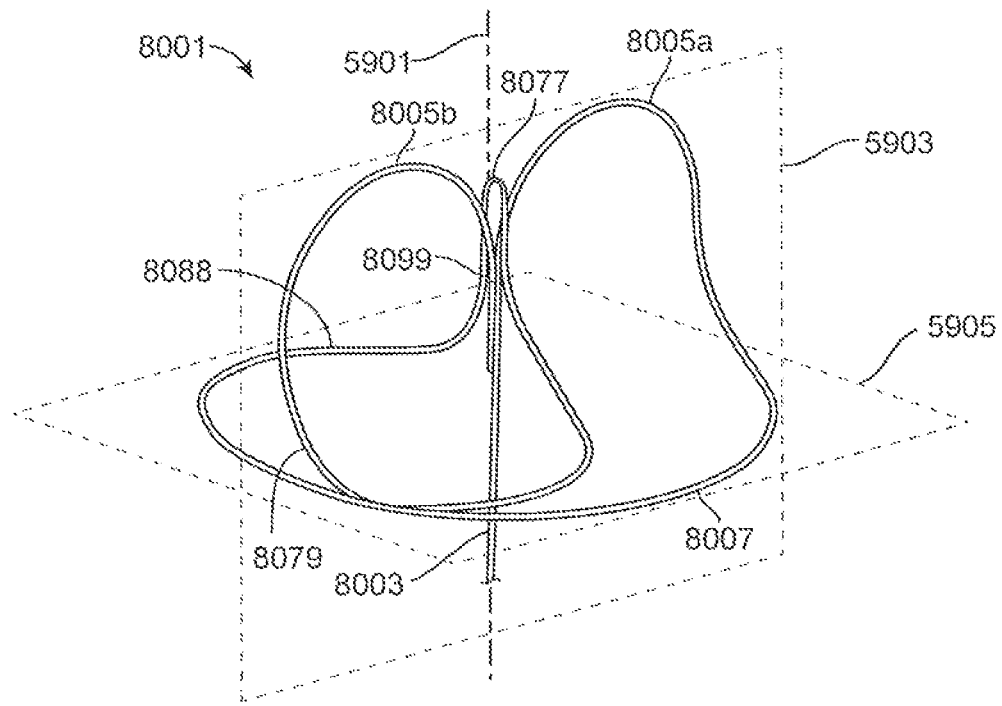
FIGS. 46A and 46B show an exemplary asymmetric looped proximal anchor.
Figure 46B:
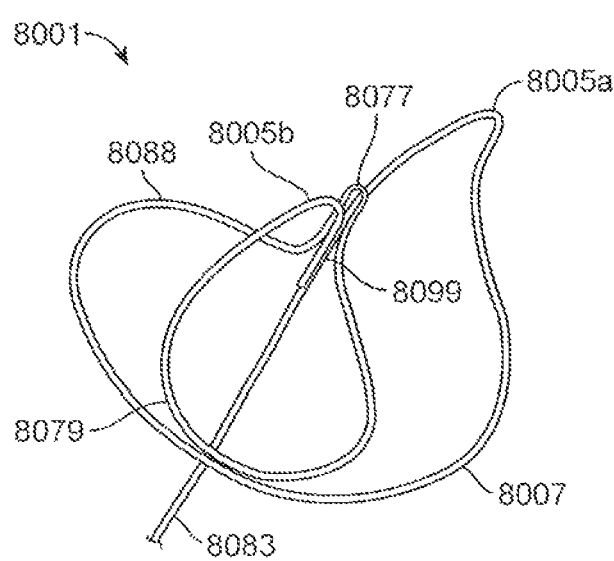
Figure 47A:
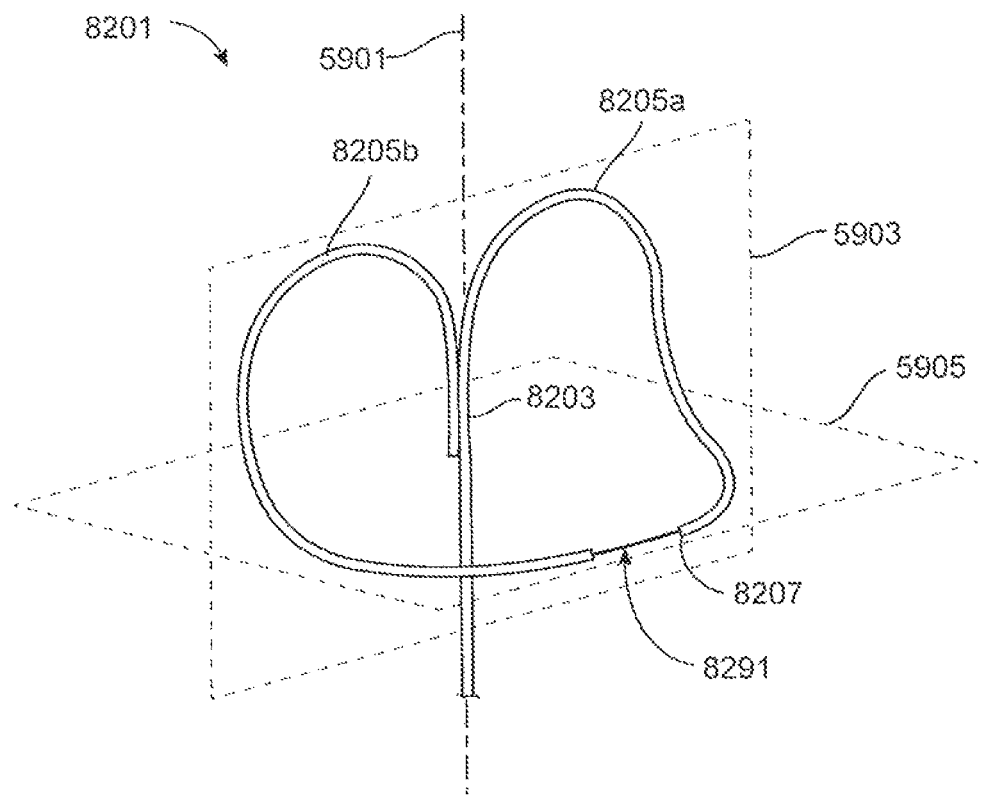
FIGS. 47A, 47B, 47C and 47D show another exemplary asymmetric looped proximal anchor.
Figure 47B:
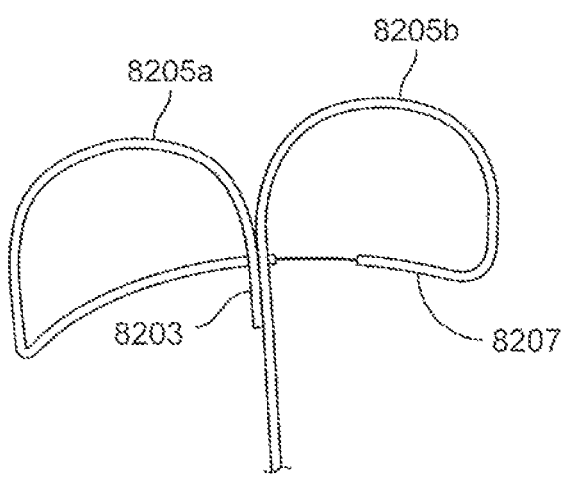
Figure 47C:
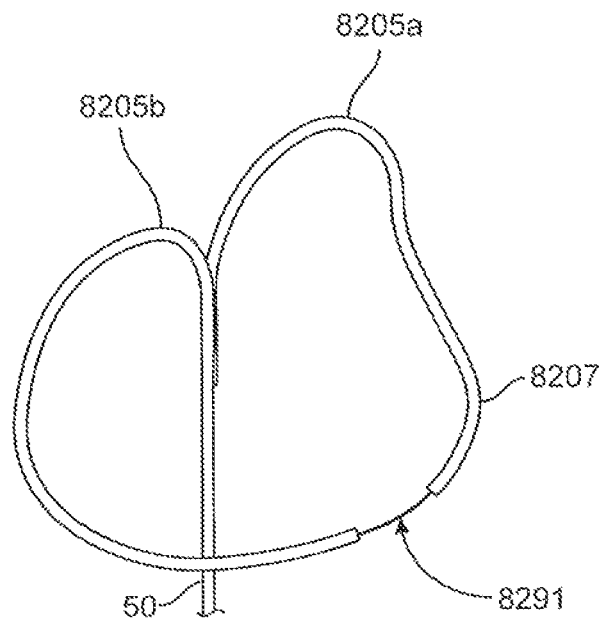
Figure 47D:
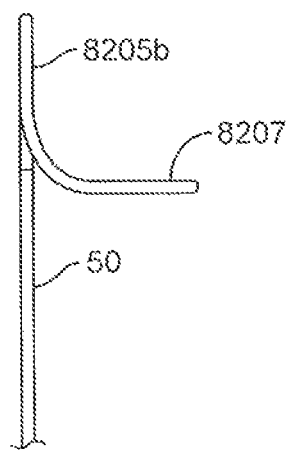
Figure 48A:
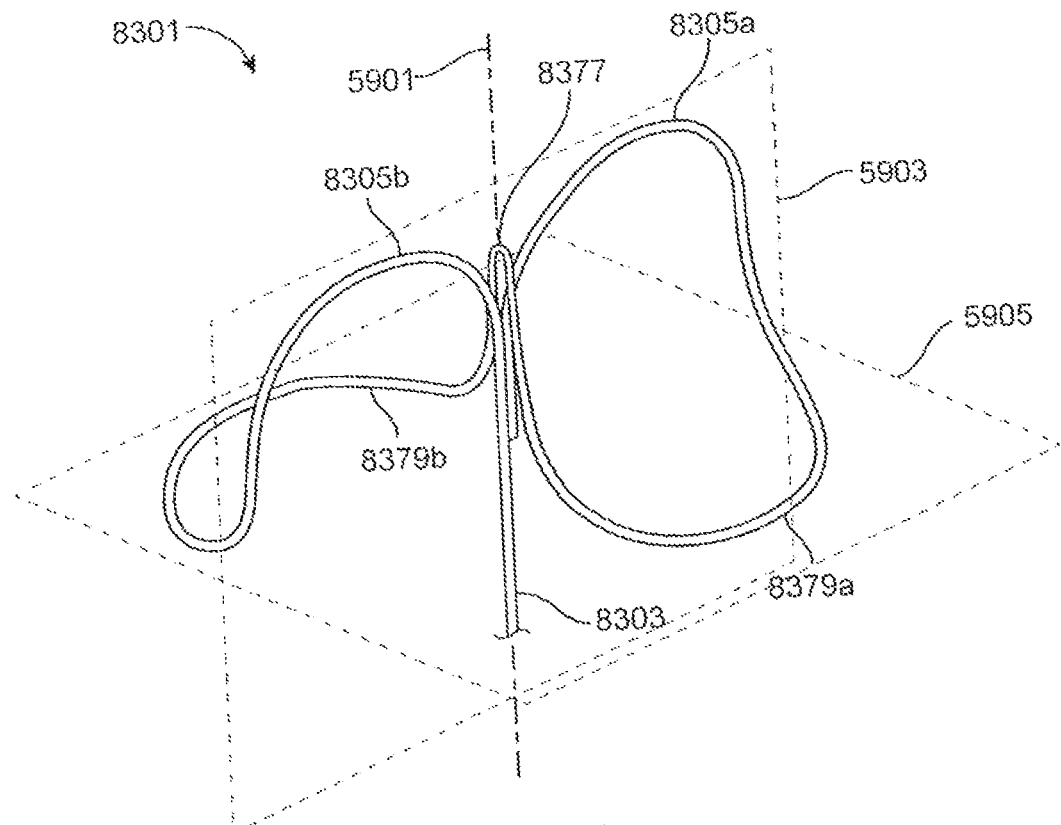
FIGS. 48A, 48B, 48C, 48D and 48E show an exemplary "figure 8" looped proximal anchor.
Figure 48B:
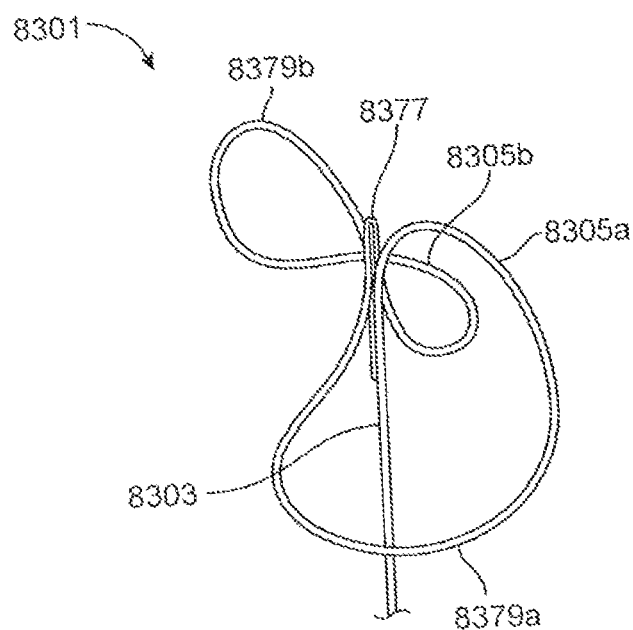
Figure 48C:
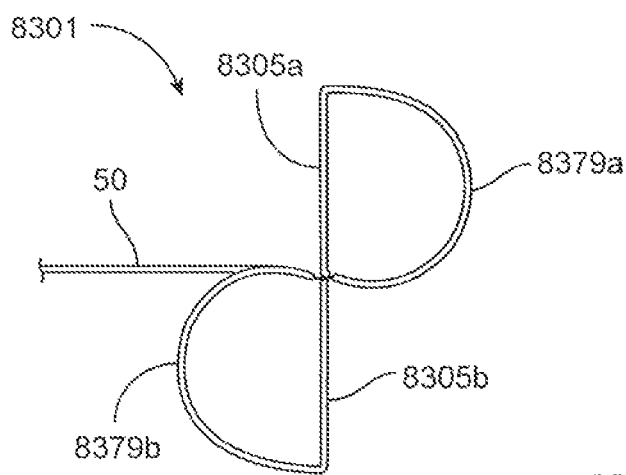
Figure 48D:
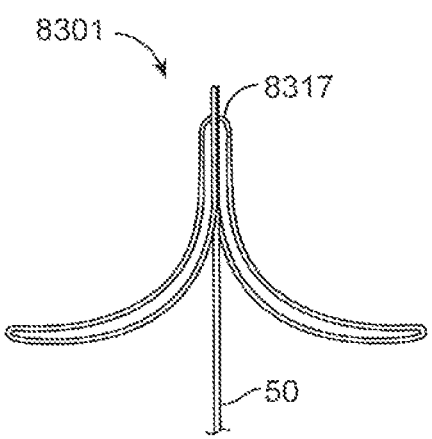
Figure 48E:
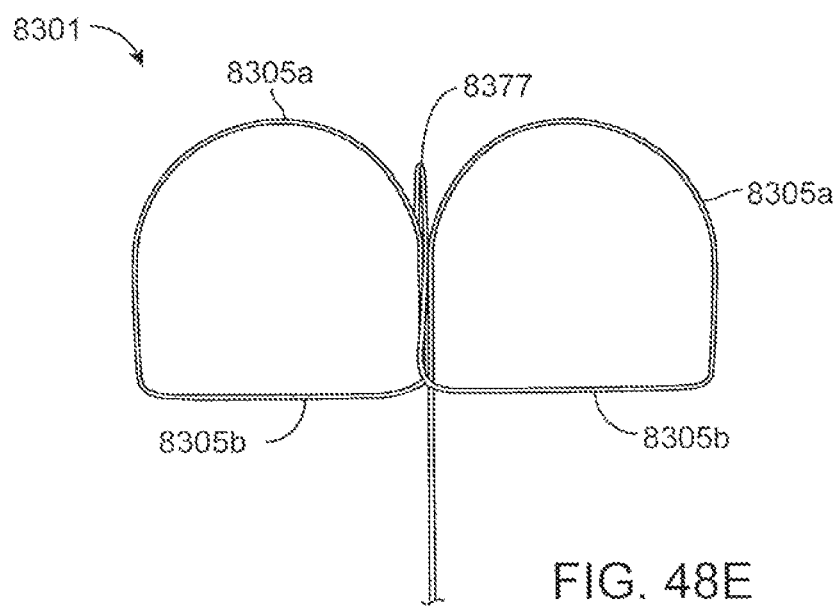
Figure 49A:
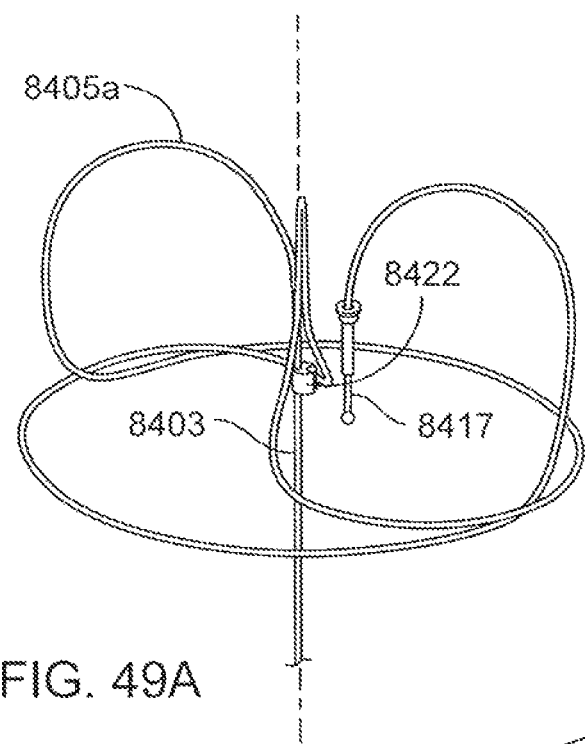
FIGS. 49A, 49B and 49C show an exemplary proximal anchor having a break therein and fastener configured to close the break.
Figure 49B:
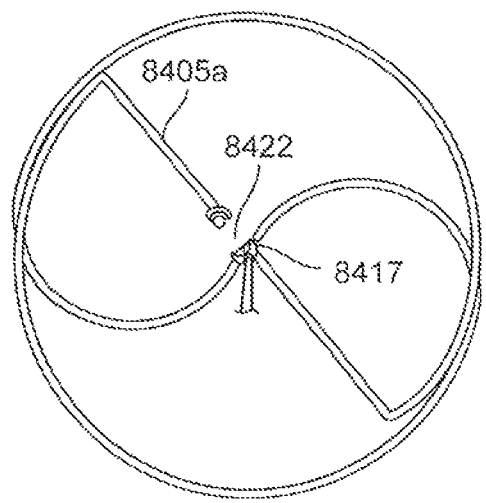
Figure 49C:
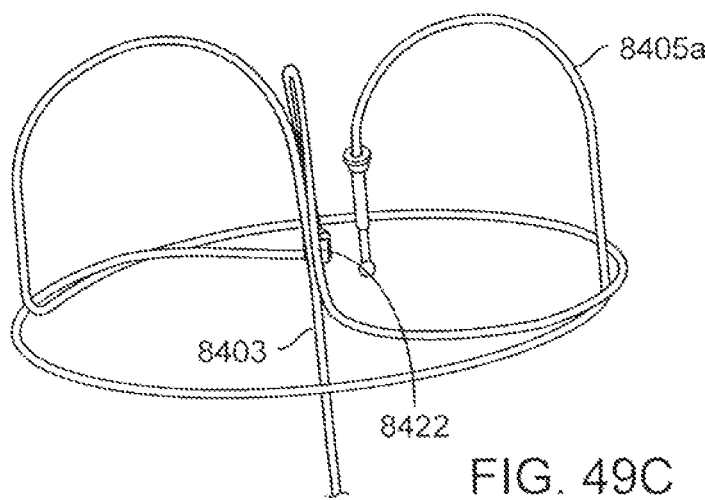

FIGS. 46A-46B show another embodiment of a proximal anchoring member 8001. The anchoring member 8001 can include a stem 8003 extending axially away from the spine (not shown), two arches 8005a,b extending radially away from the stem 8003, a coil 8007 extending annularly or at least partially around and perpendicularly to the stem 8003, a counterarch 8079, and a pull loop 8077 connected between the two arches 8005a,b.

The proximal anchoring member 8001 is asymmetric about the stem 8003 in that one arch 8005a extends proximally away from the stem 8003, curves through a proximal peak, and extends distally to merge into a single coil 8007. The coil 8007 then curves proximally into the pull loop 8077, which extends over the center connection point 8099 of the two arches 8005a,b. The pull loop 8077 then merges into the counterarch 8079, which merges into the second coil 8005b, which then joins the stem 8083 at connection point 8099. Thus, the two arches 8005a,b do not mirror one another as they merge into the rest of the anchor 8001. Further, the coil 8007 does not extend all the way around the circumference of the anchor 8001 (though in some cases, it can), and there is only one counterarch 8079. By having an asymmetric anchor, the various portions of the anchor can take independent shapes during delivery and removal, which can advantageously minimize the potential for tangling of equal and parallel features. The asymmetric anchor also includes less wire than, for example, a symmetric design where the coil extends all the way around the stem, which reduces the bulk and potential for tangling. In some cases, the asymmetric design can also be used to preferentially augment anchoring depending on orientation to the main curve distal to the proximal anchor.

The arches 8005a,b can thus extend both longitudinally and radially away from the stem 8003. This arching form can advantageously provide hoop strength to the anchor. Further, the arches 8005a,b can extend in substantially opposite radial directions. Having the arches 8005a,b extend in substantially opposite radial directions advantageously enables the arches 8005a,b to behave as moment arms and assume approximately half of the imparted load in an almost balanced manner. Likewise, having two arms that extend in substantially opposite radial directions can help keep the stem in the center of the pylorus, helping to stabilize the anchor.

The counterarch 8079 can be located approximately 90 degrees away from both arches 8005a,b. The counterarch 8079 can advantageously transfer the load from the arches 8005a,b to the coil 8007 through the pull loop 8077.

In some embodiments, the stem 8003, arches 8005a,b, coil 8007, spine, and pull loop 8077 can be formed of a continuous piece of wire that is joined at the stem. Alternatively, at least some of the stem 8003, arches 8005a,b, coil 8007, and/or spine can be individually joined together using, for example, welding, crimping, gluing, soldering, sleeving or a combination of these.

The pull loop 8077, which is connected one side to the counterarch 8079 and on the other side to the coil 8077, can be used to straighten the anchor 8001, such as for removal or delivery. To do so, the pull loop 8077 can act as a "handle" that can be pulled axially in a proximal direction with a retraction tool, such as a grasper, directly into the esophagus, into an endoscope working channel, into an overtube or into another device configured for removal. As the pull loop 8077 is pulled in a direction opposite the proximal anchor, anchoring member 8001 collapses radially inwards: the coil 8007 and the counterarch 7079 lift up and around the arches 8005a,b until the arches straighten and collapse as well. The pull loop 7077 can be retracted into the endoscope working channel to initiate device removal. The anchor 8001 will thus follow. Alternatively, the anchoring member 8001 can include a reduced diameter portion at approximately the mid-point of the anchor, such as at approximately point 8088. For delivery or removal, the anchor can thus be unwound by pulling on the reduced-diameter section to stretch and elongate the shape.

The coils 8007 can have a diameter such that, when placed in the stomach perpendicular to the pylorus, the anchor 8001 is not able to pass through the pylorus. Thus, for example, the diameter of the coil 8007 can be between 3 cm and 20 cm, preferentially between 5 cm and 15 cm. The proximal anchoring member 8001 is adapted and configured to—once delivered through an endoscope and deployed into the stomach—expand to provide a large enough structure that will prevent passage of the anchor through the pylorus. It is to be appreciated that any of the above described flow reduction elements, sleeves, features, characteristics, qualities or capabilities of the duodenal-based treatment device described herein may be used in conjunction with the proximal anchor 8001. Additionally or alternatively, the anchoring member 8001 may be used with any of the above described duodenal devices.

FIGS. 47A-47D show another embodiment of a proximal anchoring member 8201. The anchoring member 8201 can include a stem 8203 extending axially away from the spine, two arches 8205a,b extending radially away from the stem 8203, and a coil 8207 extending annularly or at least partially around and perpendicularly to the stem 8203.

The proximal anchoring member 8201 is asymmetric about the stem 8203 in that the two arches 8205a,b extend in opposite directions (one counterclockwise and the other clockwise) to both merge into the same coil 8207. The coil 8207 thus extends only part way around the circumference of the anchor 8201 (though it can extend more than one time around the circumference of the anchor 8201). By having an asymmetric anchor, the various portions of the anchor will be less likely to twist on themselves during delivery and removal, which can advantageously minimize the potential for tangling of equal and parallel features. Likewise, the simple design (having only arches and a single short coil) can help avoid tangling during delivery or removal. This simple design also requires a shorter wire, thereby reducing the length of wire that separates the two arch forms, ultimately creating a stiffer form. In some embodiments, this asymmetric design can preferentially augment anchorage. Further, in some embodiments, the coils of the anchoring member 8201 (or of any anchoring member described herein having coils) can have the coil extended at an angle greater than 90 degrees relative to axis of the stem. For example, the coil could be angled at 120 degrees relative to the top stem (could extend below the plane perpendicular to the stem shown in FIG. 47A). Such an increased angle could advantageously help prevent the coil from flipping over the arches during use.

The arches 8205a,b can extend both longitudinally and radially away from the stem 8003. This arching form can advantageously provide hoop strength for the anchor. Further, the arches 8205a,b can extend in substantially opposite radial directions. Having the arches 8205a,b extend in substantially opposite radial directions advantageously enables the arches 8205a,b to behave as moment arms and assume approximately half of the imparted load in a balanced manner. Further, having the arches 8205a,b extend in substantially opposite directions can help keep the stem in the center of the anchor, thereby enhancing stability of the anchor.

In some embodiments, the stem 8203, arches 8205a,b, coil 8207, and spine (not shown) can be formed of a continuous piece of wire that is joined at the stem. Alternatively, at least some of the stem 8203, arches 8205a,b, coil 8207, and/or spine can be joined together using, for example, welding, crimping, gluing, soldering, sleeving or a combination of these.

In some embodiments, the anchor 8201 can include a reduced-diameter section 8291 along the wire at approximately the mid-point of the wire forming the anchor. The reduced-diameter section can allow the anchor to bend easier at that section than in other areas of the wire, acting as a hinge for delivery and removal. Thus, to collapse the anchor 8201, the user can pull on the reduced-diameter section 8291 to cause the anchor to collapse.

The coil 8207 can have a diameter such that, when placed in the stomach perpendicular to the pylorus, the anchor 8201 is not able to pass through the pylorus. Thus, for example, the diameter of the coil 8207 can be between 3 cm and 20 cm, preferentially between 5 cm and 15 cm. The proximal anchoring member 8201 is adapted and configured to—once delivered through an endoscope and deployed into the stomach—expand to provide a large enough structure that will prevent passage of the anchor through the pylorus. It is to be appreciated that any of the above described flow reduction elements, sleeves, features, characteristics, qualities or capabilities of the duodenal-based treatment device described herein may be used in conjunction with the proximal anchor 8201. Additionally or alternatively, the anchoring member 8001 may be used with any of the above described duodenal devices.

FIGS. 48A-48E show another embodiment of a proximal anchoring member 8301. The anchoring member 8301 can include a stem 8303 extending axially away from the spine, two arches 8305a,b extending radially away from the stem 8303, two counterarches 8379a,b, and a pull loop 8377.

The proximal anchor 8301 can take approximately the shape of a "figure 8". Each arch 8305a,b extends proximally from the stem 8303, curves through a proximal peak, and extends distally to merge into a respective counterarch 8379a,b. The arches 8305a,b can extend both longitudinally and radially away from the stem 8303. This arching form can advantageously provide hoop strength by helping to center the anchor 8301 when the anchor 8301 is pushed or compressed from the side. The "figure 8" shape of the anchor 8301 can advantageously prevent tangling during delivery and removal because the features and free length of the wire are minimized and because there are no overlapping coils or other portions to get tangled.

The counterarches in FIG. 48 are shown as peaking or lying in a plane that is substantially perpendicular (90 degree angle) to the axis of the stem. In some embodiments, the counterarches of the anchor 8301 (or the counterarches of any anchor described herein) can be angled at more than a 90 degree angle relative to the top of the stem, such as 120 degrees (i.e. could extend below the plane perpendicular to the stem shown in FIG. 48A). Such an increased angle could advantageously help prevent the counterarches from flipping up and over the arches in use.

The arches 8305a,b can both extend counterclockwise (from the proximal point of view) as they merge into the counterarches 8379a,b. Further, the arches 8305a,b are configured to extend in substantially opposite radial directions. Having the arches 8305a,b extend in substantially opposite radial directions advantageously enables the arches 8305a,b to behave as moment arms and assume approximately half of the imparted load in a balanced manner.

The pull loop 8377 can extend in between the arches 8305a,b as they meet at the stem 8303. Further, the pull loop 8377 can merge on both sides into counterarch portions 8379a,b, which then curve upwards into the arches 8305a,b. The peak of the counterarch portions 8379a,b can extend distally and in substantially opposite radial directions from one another. Further, the counterarch portions 8379a,b can be located approximately 90 degrees away from each arch 8305a,b. This placement at 90 degrees provides for approximately four supports—at every 90 degrees around the circumference of the anchor 8301—to stabilize the anchor 8301 and discourage proximal movement of the anchor 8301. The counterarch portions 8379a,b can both loop in the same clockwise/counterclockwise direction from the pullwire 8377 (viewing the anchor from the proximal end) to connect to the arches 8005a,b).

In some embodiments, the stem 8303, arches 8305a,b, counterarches 8379a,b, spine and pull loop 7077 can be formed of a continuous piece of wire that is joined at the stem. The stem 8303, arches 8305a,b, counterarches 8379a,b, spine and pull loop 7077 can be joined together using, for example, welding, crimping, gluing, soldering, sleeving or a combination of these.

The interlock feature described above can be "unlocked" to remove the anchor 8301. To do so, the pull loop 8377 can act as a "handle" that can be pulled axially in a proximal direction with a retraction tool, such as a grasper, into an endoscope working channel. As the pull loop 8377 is pulled in a direction opposite the proximal anchor, anchoring member 8301 collapses radially inwards: counterarches 8379a,b lift up and around the arches 8305a,b, until the arches straighten and collapse as well. The pull loop 8377 can be retracted directly into the esophagus, into the endoscope working channel, into an overtube or into another device configured for removal to initiate device removal. In some embodiments, rather than having a separate pull loop, the "figure 8" can include a reduced diameter portion 8529 along the portions of the wire forming the "figure 8" (see FIGS. 50A-50B). The reduced-diameter portion 8529 can be at approximately the mid-point of the anchor. For delivery or removal, the anchor can thus be unwound by pulling on the reduced-diameter section 8520 to stretch and elongate the shape.

The anchor 8301 can have a diameter such that, when placed in the stomach perpendicular to the pylorus, the anchor 8301 is not able to pass through the pylorus. The proximal anchoring member 8301 is adapted and configured to—once delivered through an endoscope and deployed into the stomach—expand to provide a large enough structure that will prevent passage of the anchor through the pylorus. It is to be appreciated that any of the above described flow reduction elements, sleeves, features, characteristics, qualities or capabilities of the duodenal-based treatment device described herein may be used in conjunction with the proximal anchor 8301. Additionally or alternatively, the anchoring member 8301 may be used with any of the above described duodenal devices.

The anchoring members described herein, such as the anchoring members of FIGS. 7, 8, 24-26A, 30-35, 45-50, and 56 that reside in the stomach, that are not attached to the tissues, that are designed so as to not be swept through the pylorus, and that can be deployed through the working channel of an endoscope can be used with any of the devices described herein and/or with any device having a portion that extends distal to the pylorus and intended to stay in place.

Figure 35A:
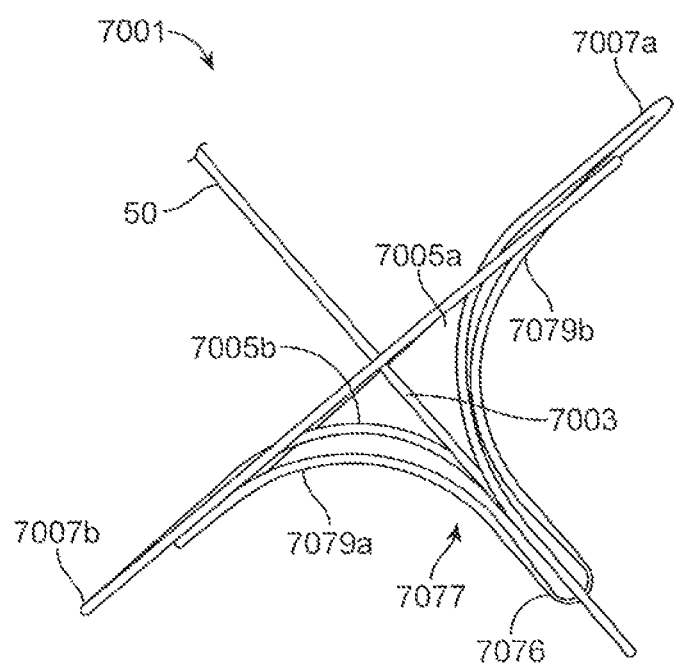
FIGS. 35A-35D are views of a proximal anchor embodiment having a pair of arches leading to counter wound coils and a pull loop extending between the arches for anchor removal.
Figure 35B:
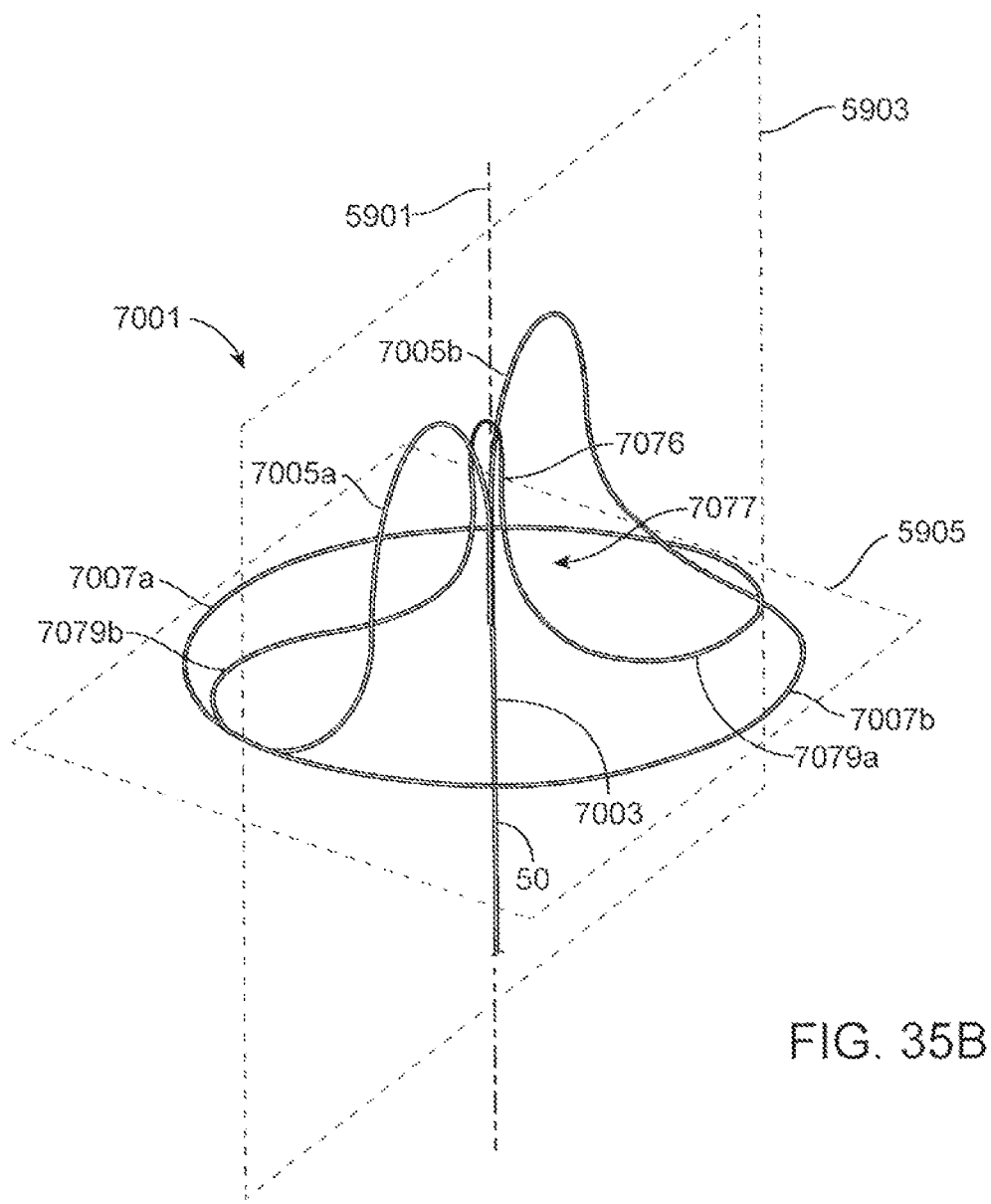
Figure 35C:
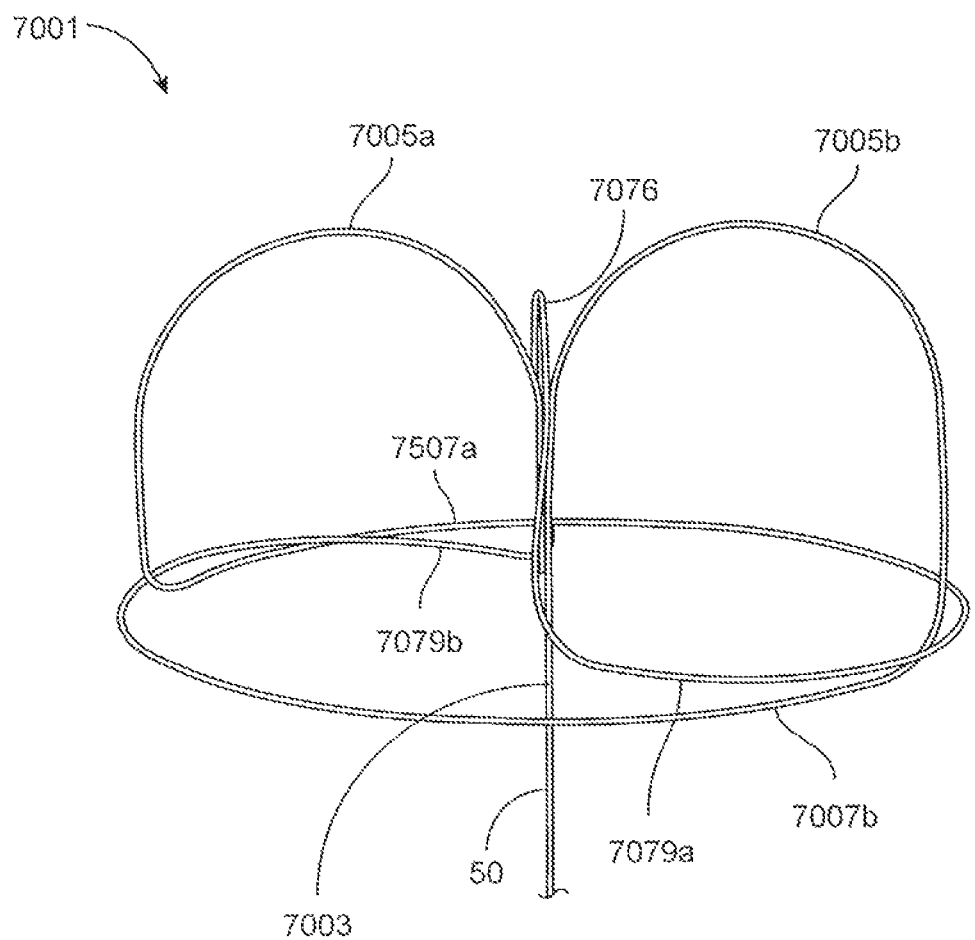
Figure 35D:
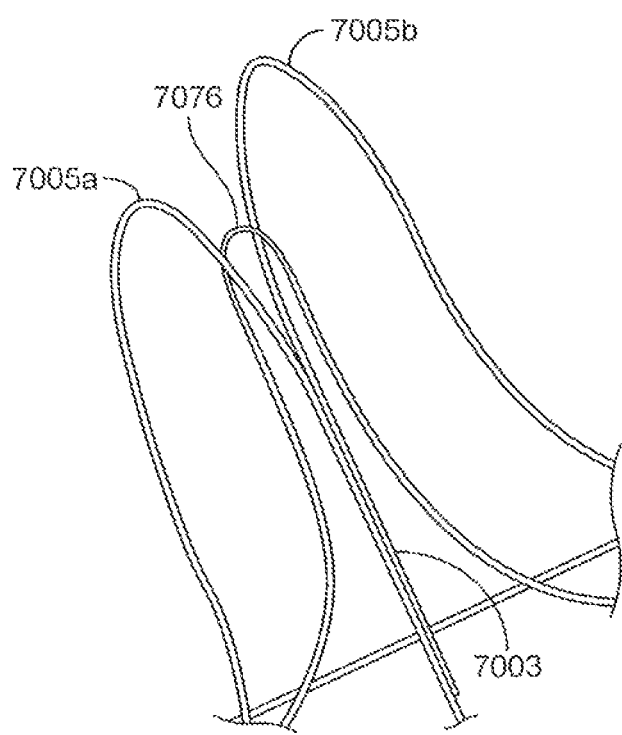

As an aid to clarify the relationship between and orientation of the various anchor components (e.g., stem, coil, arch, and counterarch) and configurations of those components, an exemplary central axis and reference planes have been shown in some embodiments. FIGS. 32A, 34A, 35B, 46A, 47A, and 48A have been illustrated with exemplary references planes 5903, 5905 (shown in dotted lines) and an exemplary central axis 5901 (also shown in dotted lines) extending through the stem. Each respective figure includes one plane 5903 that is parallel with the stem and includes one or more arch or a portion thereof. Plane 5905 is perpendicular to the stem/central axis 5901. In many embodiments, the plane 5905 includes either a coil or a distal portion of an arch or counter arch, or portion thereof. The references planes 5903, 5905 and axis 5901 have been included to provide a reference for the various angles of the exemplary configurations. It is to be understood that the stem, arches, coils, and/or counterarches may not extend exactly within these planes in some embodiments. Even if the component does not lie completely within a reference plane, the reference planes and axis also provide a way of interpreting the information in the figures. For example, an arch may be described as curving away from the stem at an angle relative to the stem or axis 5901 as shown in FIG. 32A or pair of arches in FIG. 34A. In another example, an arch may be described as curving away from or towards a reference plane 5903 at an angle. While many embodiment illustrated have one or both arches remaining generally within a reference plane 5903, the disclosure is not so limited. Portions of an arch or aches may be curved away from or towards the reference plane 5903. In another example, the angle formed by a counter arch may be described relative to the plane 5905 as shown in FIGS. 35B and 46A. In still another example, the arch-coil transition may be described as an angle in relation to the reference plane 5903. Similarly, the coil—arch transition or coil to counter arch transition may be viewed as the angle formed from the coil lying generally within the plane 5905 and then angling out of plane 5905 towards the arch or counter arch, depending upon embodiment. While specifically illustrated in FIGS. 32A, 34A, 35B, 46A, 47A and 48A, it is to be appreciated that the disclosure includes these reference planes and central axis in each of the figures illustrating an anchor embodiment.

Locks for Looped Anchors

Figure 50A:
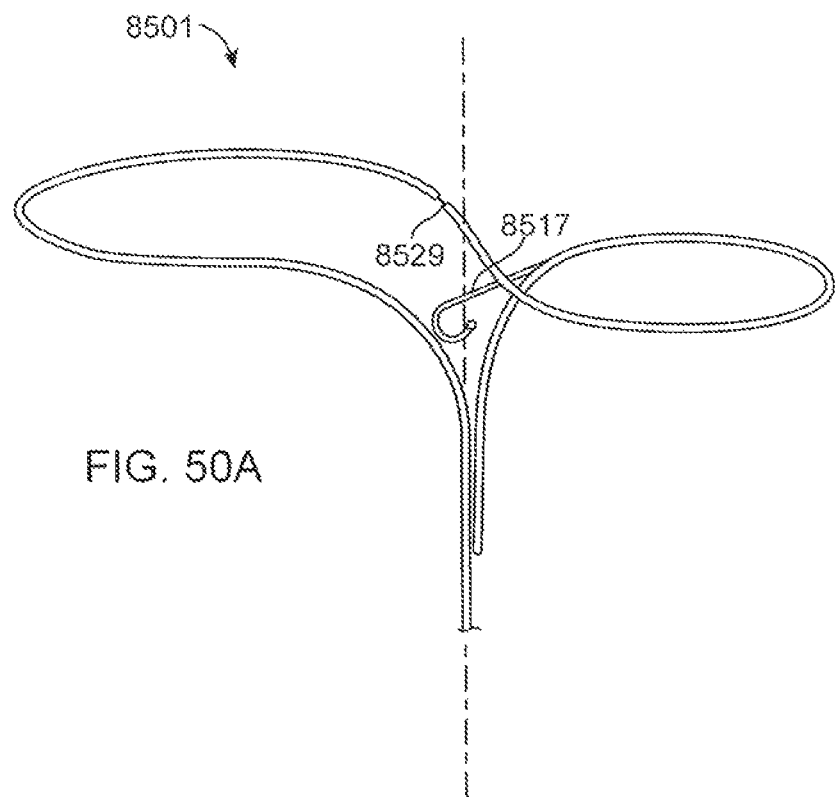
FIGS. 50A and 50B show an exemplary "figure 8" looped proximal anchor having a fastener to help hold the shape.
Figure 50B:
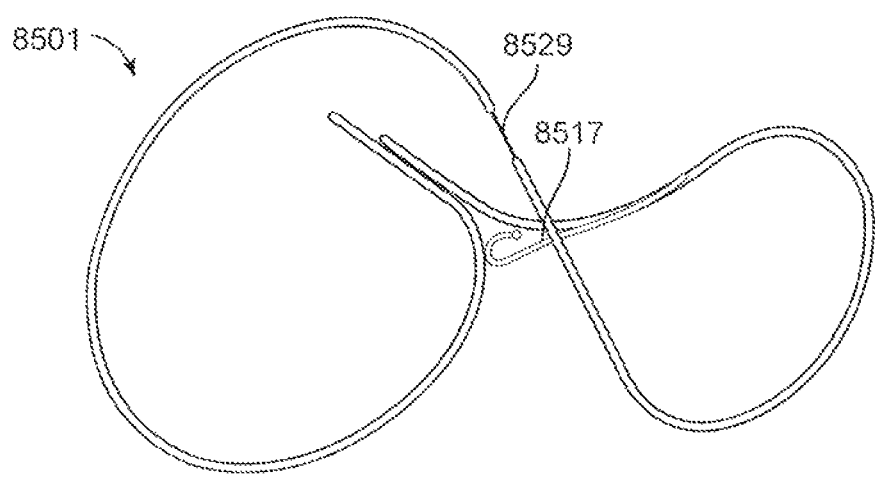

Any of the above anchor embodiments can further include a fastener to help hold the shape of the anchor (rather than to just close a break). For example, as shown in FIGS. 50A-50B, an anchor 8501 similar to the anchor 8301 of FIGS. 48A-48D can include a latching mechanism 8517 to hold the anchor in its shape. In this example, the latch 8517 can connect a first loop of the "figure 8" to a second loop of the "figure 8", thereby limiting the translation and collapse of the wire and helping to maintain the anchor shape.

Figures 26A, 26B:
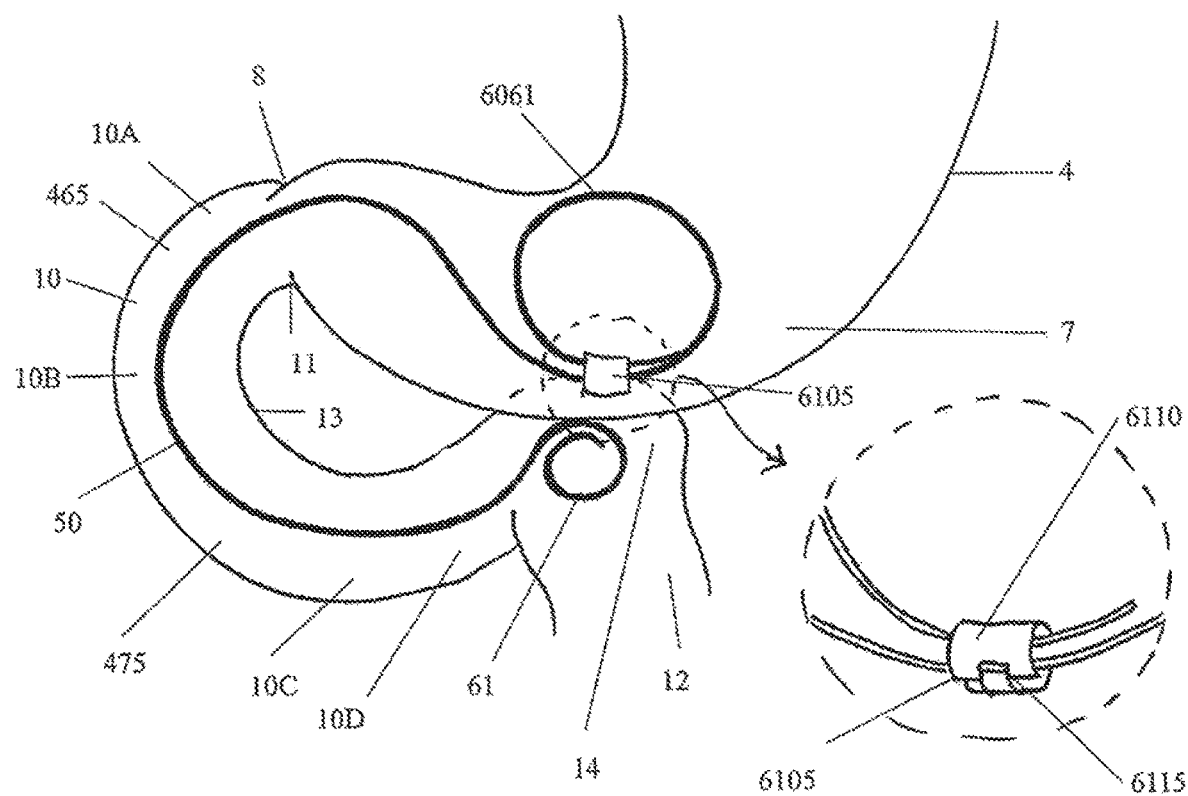
FIG. 26A shows a section view of the stomach with a device implanted into the duodenum having an enlarged proximal coil and a retaining ring on the coil (seen best in the enlarged view of FIG. 26B)

As another example, referring to FIGS. 26A and 26B, a retainer 6105 can be used to lock a portion of the coil of the anchor 6061 (of FIG. 25) together. The retainer 6105 is positioned to further prevent the coil 6061 from losing structure and able to be straightened out. The retainer 6105 is placed along the coil 6061 to fasten the coil to itself. The retainer 6105 may be installed on the coil 6061 after the device is implanted in the gastrointestinal tract and/or may be pre-installed and latched together once the coil is implanted in the gastrointestinal tract. The retainer 6105 may be adjustable or removable to facilitate device removal (i.e., to permit the coil 6061 to be straightened).

An illustrative retainer embodiment is shown in the enlarged view FIG. 26B. In this exemplary embodiment, the retainer 6105 has a body 6110 and a fastener 6115. The body 6110 is shaped and sized to accommodate the number of coils or wires used (or requiring attachment) in a particular configuration. The fastener 6115 is shown as a tab that attaches to the outer surface of the body 6110. The retainer 6105 is formed from any of a wide variety of durable biocompatible materials suited for use in the environment of the stomach and compatible with the materials and characteristics of the device and coil. Other configurations of the retainer 6105 are possible. The specific shape and dimensions of the retainer 6105 will vary depending upon the type of joining technique used such as threaded connections, hook and loop connections, spine joins or friction fits, as well as the delivery method.

Figure 26C:
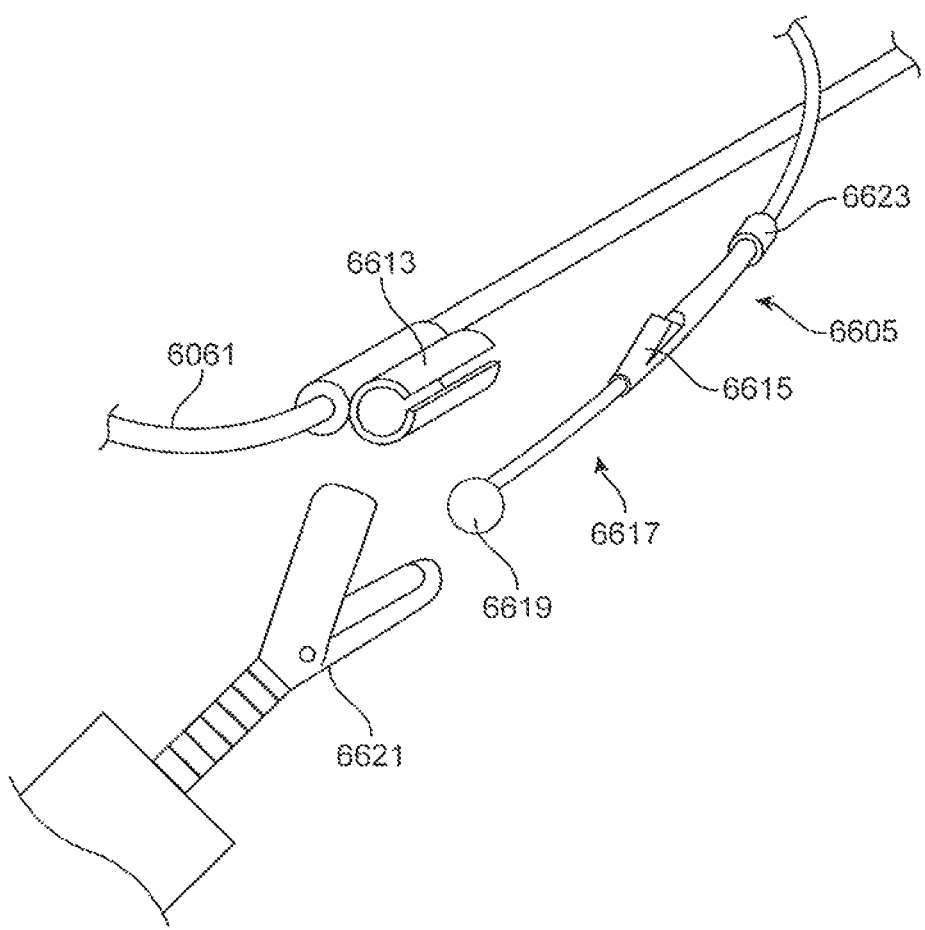
FIG. 26C is an alternative fastener and clip for retaining a coil.

An alternative embodiment of a fastener for use with a looped wire anchor is shown in FIG. 26C. The fastener 6617 can include a split tube 6613 connected to the body of the coil 6061 and a ball 6619 and latch 6605 on a proximal end of the coil 6061. The latch 6605 can include a distal-facing spring mechanism 6615 and a stopper 6623. To activate the fastener 6617, a grasper 6621 can be used to grab the ball 6619 and pull the distal end of the coil 6061 in through the side of the split tube 6613. The ball 6613 can then be pulled proximally, compressing the spring arm 6615 until it slides through and proximal of the split tube and springs back to an expanded state, catching the arm backside on the shoulder of the split tube 6613. The split tube 6613 can thus be caught between the spring mechanism 6615 and the stopper 6623, thereby securing the coil 6061 to itself.

Alternative fastener designs are shown in FIGS. 37A-44B.

Figure 37A:
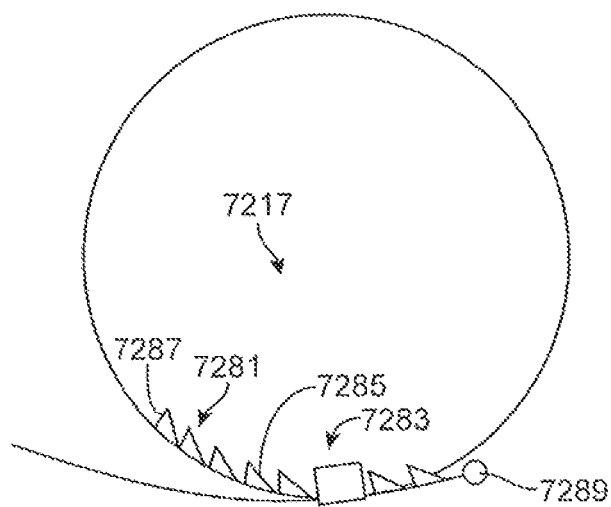
FIGS. 37A and 37B show an embodiment of a fastener for locking a proximal anchor.
Figure 37B:
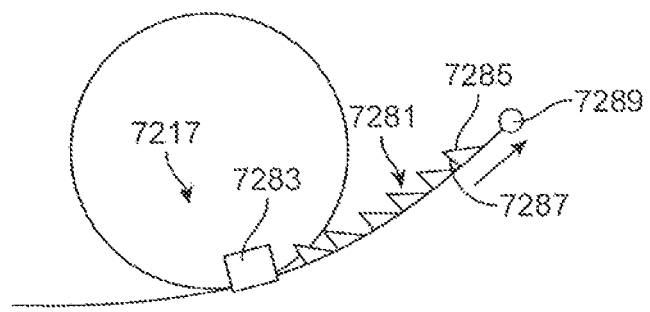

Referring to FIGS. 37A-37B, a fastener 7217 can include extensions or teeth 7281 along a portion of the wire forming the loop and a cinch mechanism 7283 configured to engage with the teeth 7281. The teeth 7281 can have proximally-facing sloped edges 7285 configured to allow the cinch mechanism 7283 to slide thereover and edges 7287 that are more perpendicular to the wire that are configured to hold the cinch mechanism 7283 in place. Accordingly, as the proximal end 7289 of the anchor is pulled proximally, the cinch mechanism 7283 will slide over the sloped edges 7283 to lock the anchor in the desired diameter or configuration (as shown in FIG. 37B, the further the proximal end is pulled, the smaller the diameter loop can result). Thus, for example, a larger diameter can be used to ensure that the loop is too large to pass through the pylorus. The smaller diameter can be used for removal, for example to make the loop small enough to be pulled through the esophagus. Because the distal edges 7287 are approximately perpendicular to the wire, distal pulling of the wire or anchor (such as by the pylorus) will cause the cinching mechanism 7283 to hit the edges 7287 without sliding over, thereby locking loop or anchor in the desired shaped. In some configurations, and as shown in FIGS. 37A-37B, the fastener 7217 can include a ball or other feature on the proximal end 7289 to aid in grasping for locking while in the stomach (for example, similar to the ball 6619 described with reference to FIG. 26C).

Figure 38A:
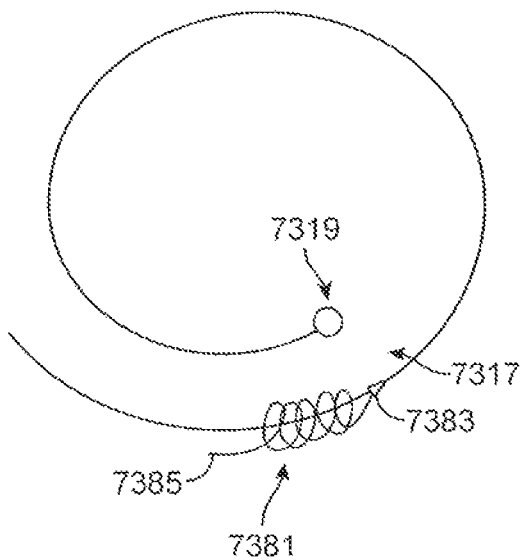
FIGS. 38A, 38B, and 38C show another embodiment of a fastener for locking a proximal anchor.
Figure 38B:
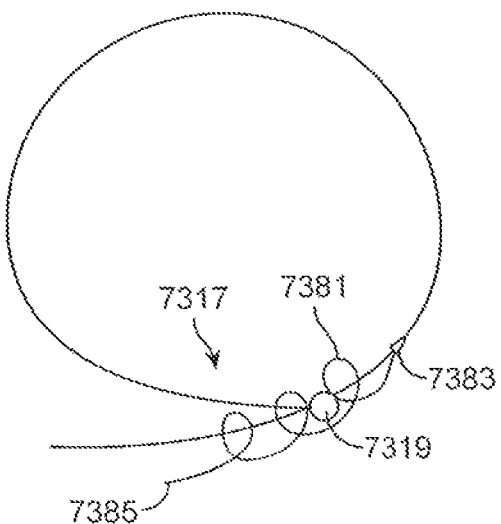
Figure 38C:
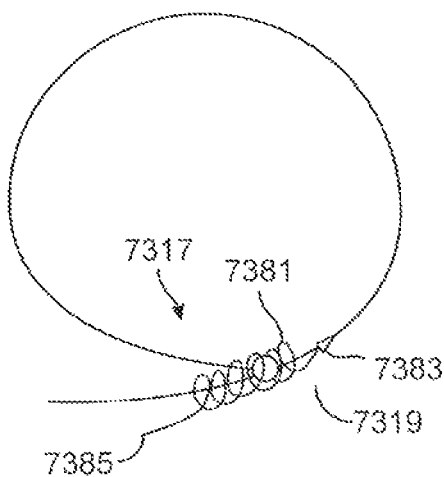

Referring to FIGS. 38A-38C, a fastener 7317 can include a spring 7381 attached at an attachment point 7383 along the loop such that one end 7385 is unattached to the loop. The fastener 7317 can further include a ball 7319 on the free end of the loop. As shown in FIG. 38B, as the loose end 7385 is pulled, the spring 7381 can open up or extend such that there is enough room between the coils of the spring to fit the ball 7319 between two coils of the spring. As pressure is released on the loosed end 7385 of the spring 7381, the spring 7381 will spring back into shape, thereby capturing the ball 7319 therein and locking the loop in place (as shown in FIG. 38C). The fastener 7317 can be easily unlocked by pulling on the loose end 7385 again, thereby opening the spring and allowing the ball 7319 to be released.

Referring to FIGS. 39A-39B, a fastener 7417 can include an eyelet 7481 on the loop and a barb 7483 on the free end of the loop. The barb 7483 can include two pointed ends 7485 that cross one another. After implantation in the gastrointestinal tract, the center of the barb can be pushed into the eyelet 7481, causing the pointed ends 7485 to splay apart and allow engagement with the eyelet 7481. As the pointed ends 7585 pull back to cross over one another, the barb 7483 will be caught in the eyelet 7481, thereby locking the looped anchor in the desired configuration. To unlock the fastener 7417, the free end can be pushed towards the eyelet 7481 such that the base of the hook slides up and over the top of the eyelet 7481, allowing the hooks to fold inward and release the lock.

Referring to FIGS. 40A-40B, another embodiment of a fastener 7517 includes a ball 7519 on the free end of the loop. The fastener 7517 further includes a locking mechanism 7583 on the loop. The locking mechanism 7583 includes an extension 7585 having a slot 7587 therein. The slot can include one end having a larger diameter than the ball 7519 and another end having a smaller diameter than the ball 7519. The locking mechanism 7583 can be oriented such that the smaller diameter portion is always closest to the ball (i.e. such that the ball will want to fall into the small diameter portion). The smaller diameter portion can be configured to snap the ball 7519 therein to keep it from moving back and forth once in place. To unlock the fastener 7517, the ball 7519 can be pulled or pushed towards the larger diameter portion.

Referring to FIGS. 41A-41B, another embodiment of a fastener 7617 includes a spiral or helical curved portion 7681 on the free end of the loop and a plurality of beads 7683 along a portion of the loop. The helical portion 7681 can include the same number of loops 7685 as the number of beads 7683. Further, the turn-to-turn distance of the helix can match the gap between the beads 7683. The loops 7685 can be configured to be captured between the beads 7683 to lock the looped anchor in place by twisting the free end with the helix 7685 over the portion of the loop with the beads 7683. The locking mechanism 7617 can be unlocked by twisting the free end in the opposite direction. The fastener 7617 can further include a ball 7619 configured to engage with a grasper to assist in locking and unlocking the fastener 7617.

Referring to FIGS. 42A-42B, another embodiment of a fastener 7717 can include an eyelet 7781 on the free end of the loop 7783 and a post 7785 and tab feature (similar to Velcro) on the loop. The eyelet 7781 can be extended over the tab 7783 (it will deflect to allow the eyelet 7781 to extend thereover). Once over the tab 7783, the engagement of the tab 7783 with the top of the post 7785 will prevent the fastener 7717 from unlocking. To unlock the fastener 7717, the eyelet 7781 can be pulled to deflect the post 7785, thereby releasing the eyelet 7781.

Referring to FIGS. 43A-43B, another embodiment of a fastener 7817 includes a hole 7883 extending through a free end of the loop. The fastener further includes a post 7885 on the loop configured to fit through the hole 7883. To lock the post 7885 into place inside the hole 7883, a sleeve 7887 can extend over the engaged post 7885 and hole 7883. To unlock the fastener 7817, the sleeve can be slid in the opposite direction.

Referring to FIGS. 44A-44B, another embodiment of a fastener 7917 includes an eyelet 7983 on a portion of the loop and a locking mechanism 7981 on the free end of the loop. The locking mechanism 7981 includes a first bump 7935 having a diameter that is smaller than the inner diameter of the eyelet 7983 (such that the first bump 7935 can fit through the eyelet 7983 and a second bump 7933 having a diameter larger than the inner diameter of the eyelet 7983 (i.e. so that the second bump 7933 cannot fit through the eyelet 7983). The first bump 7935 can include a groove 7937 therein configured to allow the free end of the wire to be directly adjacent to the main wire, thereby allowing the first bump 7935 to fit through the eyelet 7983. The first bump 7933 can have an outer shape configured to match the inner circumference of the eyelet 7983 only in a specific orientation such that, once locked, accidental unlocking of the fastener 7917 is unlikely. In some embodiments, the eyelet 7983 can be malleable such that it can be crushed after locking, thereby ensuring that the fastener will not come unlocked during use.

Any of the locking mechanisms described herein with respect to FIGS. 26A-26C and 37A-44B can be used in combination with any of the anchoring systems described herein, but particularly with respect to the anchors of FIGS. 25, 32-35, and 45-50.

Any of the above anchor embodiments can include one or more "breaks" therein (such as breaks in the wire) configured to be latched together once deployed in the gastrointestinal tract. Such breaks in the anchor design can advantageously help avoid twisting or tangling that can otherwise occur when the anchors are stretched out for delivery or when the anchors are being removed. Such twisting or tangling can due to: (1) portions of the anchor, such as arches, turning in the same clockwise or counterclockwise direction such that, when released, they want to preferentially turn as well; and (2) releasing of the anchors in the opposite direction of how they are loaded (device is pulled into a tube, thereby causing it to rotate in one direction, and pushed out of the tube, thereby rotating in the same direction again). Breaks in the wire can help avoid this twisting. For example, referring to FIGS. 49A-49C, an anchor 8401 can be designed similar to the anchor 7001 of FIG. 35. Rather than being a continuous anchor, however, the anchor 8401 can include a break 8422 between one of the arches 8405a and the stem 8403. A latch 8417 (shown here as similar to the fastener 6617 shown in FIG. 26C) can be used to close the break 8422 once the anchor 8401 is implanted. The latch 8417 can be any of the latches described with respect to FIGS. 26A-26C and 37A-44B. In some embodiments, twisting can also be avoided by releasing the device in a proximal-to-distal manner.

In many of the illustrative embodiments of the device described herein, the device is illustrated as having a latching mechanism, retainer or fastener for attaching, joining or releasably attaching one part of the device to another such as shown in FIGS. 26A to 26C or in the various alternatives shown and described in FIGS. 37-45 and 49A-49C, for example. It is to be appreciated that the latching, fastening or attachment devices and techniques may be modified for application to, for example, reversibly join similar portions of a device. In this aspect, each of the parts a particular fastening device embodiment is on the same element or type of element. In one embodiment, any one or a combination of the above described attachment devices or techniques used to join a first portion of a coil to another portion of the same coil or a different coil. In another embodiment, any one or a combination of the above described attachment devices or techniques used to join a first portion of an arch to another portion of the same arch or a different arch. In still another embodiment, any one or a combination of the above described attachment devices or techniques used to join a first portion of a stem to another portion of the same stem or a different stem. In still another embodiment, any one or a combination of the above described attachment devices or techniques used to join a first portion of a counter arch to another portion of the same counter arch or a different counter arch.

In still other embodiments, it is to be appreciated that the attachment devices and techniques described such as shown in FIGS. 26A to 26C or in the various alternatives shown and described in FIGS. 37-45 and 49A-49C, for example, may be modified for application to reversibly join different portions of a device. In this regard, it is to be appreciated that the latching, fastening or attachment devices and techniques may be modified for application to, for example, reversibly join different portions of a device. In this aspect, each of the parts of a particular fastening device embodiment are on a different element or type of element. In one aspect, a portion of a coil may be attached to a different coil, to a stem, to an arch, or to a counter arch. In another aspect, a portion of a stem may be attached to another stem, a coil, an arch or a counter arch. In still another aspect, a portion of an arch may be attached to another arch, a stem, a coil, or a counter arch. In still another alternative, a portion of a counter arch may be attached to another counter arch, an arch, a stem or a coil.

Single Wire Anchor Embodiments

Figure 52A:
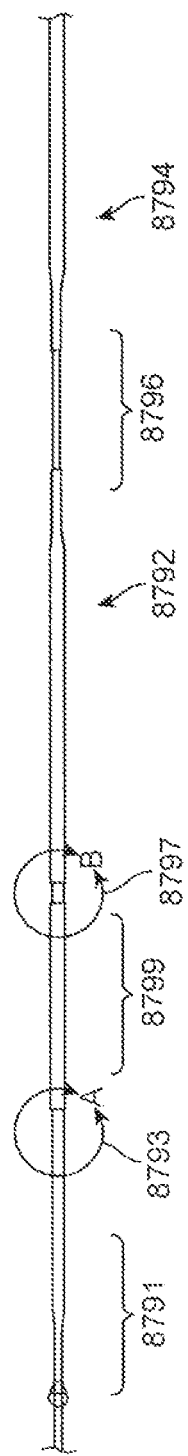
FIGS. 52A, 52B and 52C show an exemplary single wire for use in forming a proximal anchor, such as the proximal anchor of FIG. 35.
Figure 52C:
Figure 52B:

As described above, the looped anchors of FIGS. 25, 32-35, and 45-50 can be formed of a single continuous wire. Referring to FIGS. 52A-52C, a wire for use in forming the anchor 7001 of FIG. 35 can include a thin portion 8791 at the distal end configured to curl into a "pigtail"-like end, a stepped portion 8793 having a stepped section of lower diameter configured to provide room to fuse or bond the flow reduction sleeve thereto, a central portion 8799 configured to form the spine, and a stepped portion 8797 having a stepped section of lower diameter configured to provide a bonding spot for a stopper (i.e. to stop the sleeve from extending therepast). Further, the wire can include two sections 8792, 8794 that form the arches and coils as well as a necked down section 8796 that forms the pull wire of the anchor.

In some embodiments, such as FIGS. 32-35 and 46-50, the stem of the proximal anchor can include two adjacent portions of wire. As shown in FIG. 51, the stem 8703 can include a first section of wire 8755, which can be continuous with the spine, adjacent to a second section of wire 8757, which can be the end of the looped portion of the anchor. The second section 8757 can end with a sloped surface 8759 configured to create a smooth interface at the junction between the two sections.

In some embodiments, as shown in FIG. 51, a sleeve 8795 can be placed over a portion of the connection between the two sections 8755, 8757 to help bond the two sections together. In some embodiments, the two sections 8755, 8757 can be welded together while in other embodiments, the two sections 8755, 8757 can be welded to the sleeve 8795.

Figure 36A:
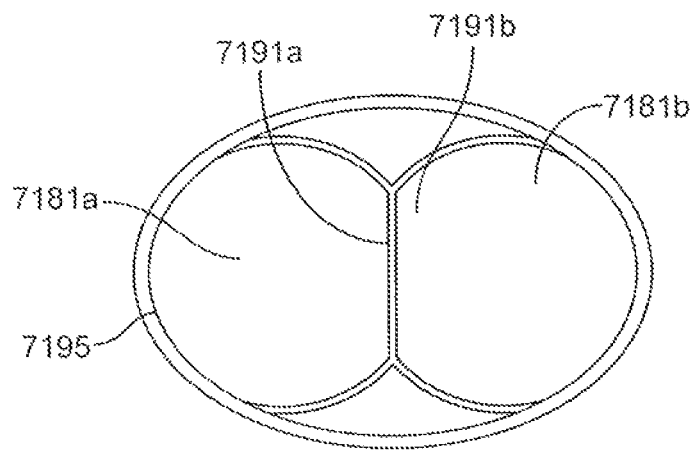
FIGS. 36A and 36B are views of a portion of a proximal anchor where distal ends of the arches of the proximal anchor have been flattened at the joint between the two arches.
Figure 36B:
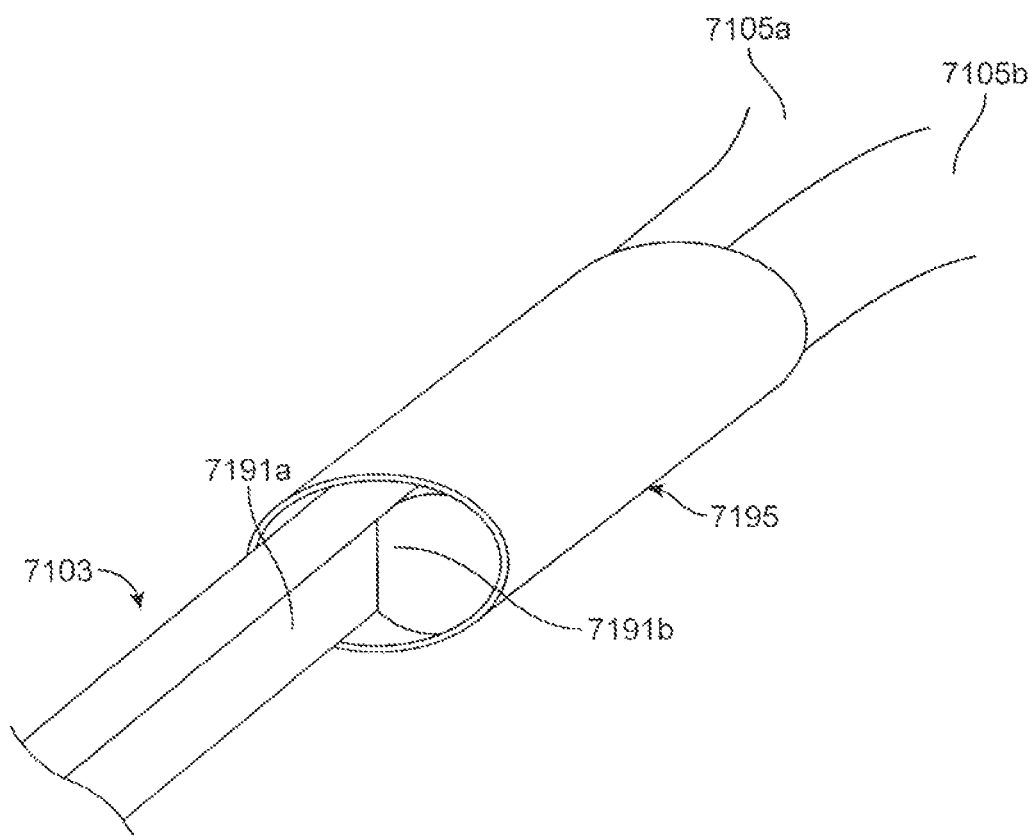

In some embodiments, two wire sections of the stem can be include flat surfaces that lay against one another to provide stability at the junction. Referring to FIGS. 36A-36B, the two sections 7181a,b of the stem 7103 each have a flat surface 7191a,b that extends axially from the distal ends of the sections 7181a,b to the start of the arches 7105a,b creating a 'D' shaped cross-section (see FIG. 36A). When the flat surfaces 7191a,b are placed against one another, flat-against-flat, the total circumference of the wires together can form approximately an oval, as shown in FIG. 36A. The two sections 7181a,b can be joined securely with a tube 7195 that can have a length similar to the length of the flat sections 7191a,b. The tube 7195 can assume an oval shape so as to approximately assume the oval profile of the flat sections 7191a,b. For example, the tube 7195 can be elastically deformed to the proper shape. When the deforming force is removed from the tube 7195, it will attempt to reassume its unstressed round shape, thereby clamping the sections 7181a,b together and preventing relative movement in both an axial and radial manner.

Figure 36C:
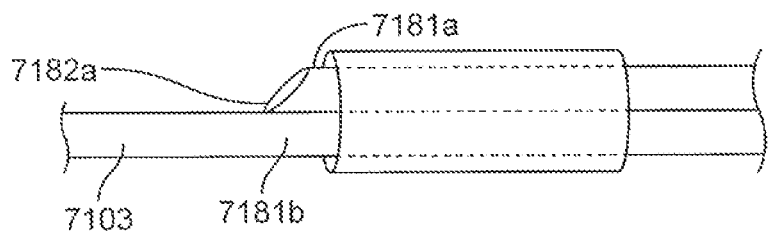
FIGS. 36C-36E are views of a portion of a proximal anchor where the distal end of an arch has been angled to smooth the transition between the stem and the arches.
Figure 36D:
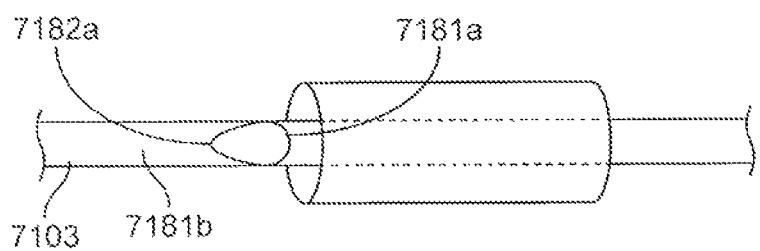
Figure 36E:
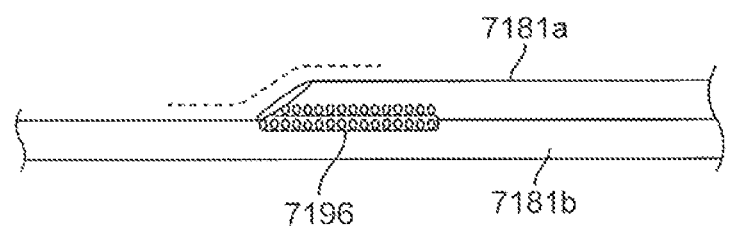

As noted above with respect to FIG. 51B, the two wire sections of the stem can be angled so that the transition from the spine to the two arches is gradual, thereby providing a smooth surface for the stomach tissue to reside against and a leading device profile that is easier and less traumatic for the endoscope working channel to deliver. Referring to FIGS. 36C-36D, the wire section 7181a of an arch can have an angled surface, such as be angled to a tip 7182a. The wire section 7181a can be positioned such that the longer edge, i.e. the edge with the tip 7182a, attaches to the adjoining distal end 7181b, thereby providing a smooth transition along the outer edge of the distal end 7181a. Further, the cut end can extend out fully out of the tube such that there is space between the angle and the sleeve 7195 to provide additional strength to the stem, i.e. to avoid having a weak point right at the transition from the sleeve to a single wire forming the stem 7103. Further, referring to FIG. 36E, the proximal ends 7181a,b can be attached together at an attachment point 7196 that extends substantially all the way to the tip of the angled portion. For example, the proximal ends (such as the free end and the main wire from the spine) can be welded together. This attachment point can be used with or without the tube 7195.

Referring to FIGS. 53A-53C, in some embodiments, the two wire sections 8181a,b of the stem 8803 can be welded to an outer sleeve rather than to one another. Each section can be welded to the sleeve 8895 at positions 8802, 8804 substantially opposite the junction of the two wires. This weld can help prevent the portions of wire from twisting with respect to one another. Further, the sleeve 8895 can be formed of a naturally cylindrical tube. As a result, one placed around the sections, the tube will tend to want to expand to its original shape, thereby placing an inward pressure on the two sections 8181a,b to cause them to remain joined.

It is to be understood that the wire sections of the stem can be joined in a variety of different ways. For example, the wire sections can be twisted together, latched with any of the latching mechanisms described herein, or bound together with a loose sleeve that allows a wire end to slide along the main wire axially, but remain in position radially.

Delivery of Looped Anchors

The looped anchors described herein, such as those described with respect to FIGS. 25-26A, 32-35, and 45-50, can be delivered or removed by straightening the anchor and pulling or pushing it with a tool, directly into the esophagus, into a working channel of an endoscope, or into an overtube or into another device configured for removal.

In some configurations, the wire can include a pusher against which a delivery tool can be pushed for delivery. For example, referring to FIG. 32, the coil 6707 can include a pusher 3233, which can be an enlarged feature on the wire, configured to provide support for pushing the collapsed anchor during delivery or removal.

Referring to FIGS. 57A-D, one embodiment of a pusher 5733 can have a proximal barrel 5716, a distal annular shoulder 5714, and a concentric lumen 5708 extending therethrough (such that the lumen 5708 can surround the wire of the anchor). In use, the delivery tool can be slid over the end of the wire forming the anchor and over the proximal barrel 5716 of the pusher 5733 until it bumps up against the shoulder 5714. The shoulder 5714 can thus form a solid and larger surfaces area with which the delivery tool can engage.

An alternate pusher embodiment is shown in FIGS. 58A-58E. The pusher 5833 can include a proximal barrel 5816 and a distal annular shoulder 5814. An off-center lumen 5808 extends therethrough, and a notch or v-groove 5810 extends axially along the side of the pusher 5833 opposite the lumen 5808. The pusher 5833 can be used, for example in double arch configurations where two extend side-by side (the v-groove 5810 can provide space for the additional wire). In use, the delivery tool can be slid over the end of the wire forming the anchor and over the proximal barrel 5816 of the pusher 5833 until it bumps up against the shoulder 5814. The shoulder 5714 can thus form a solid and larger surfaces area with which the delivery tool can engage.

Secondary Anchoring in the Bulb

Figure 54:
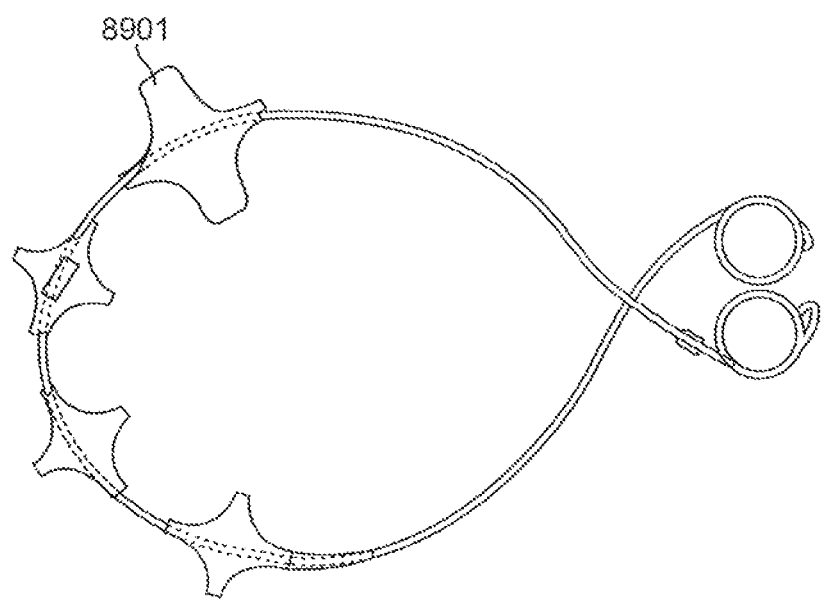
FIG. 54 shows a gastrointestinal device having an exemplary secondary bulb anchor.
Figure 55:
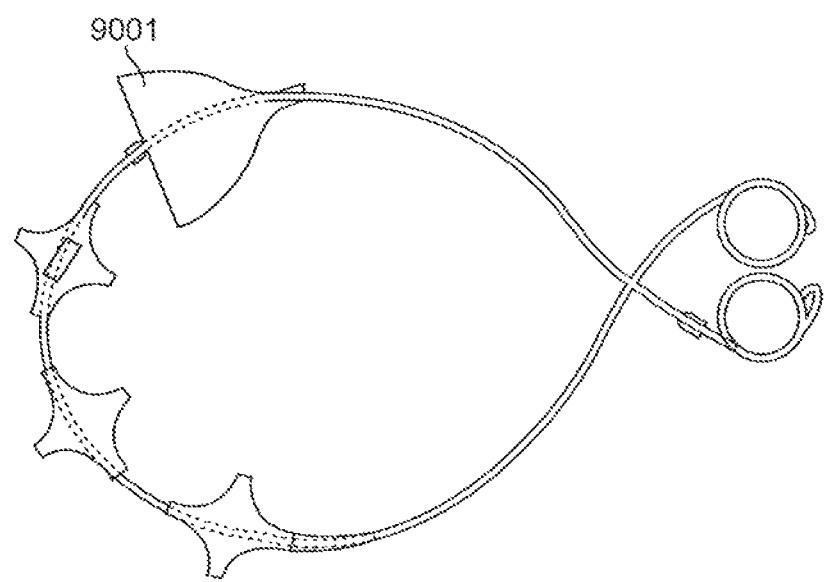
FIG. 55 shows a gastrointestinal device having another exemplary secondary bulb anchor.

In some embodiments, referring to FIGS. 54 and 55, a secondary anchor can be configured to be placed in the duodenal bulb. Referring to FIG. 54, the bulb anchor 8901 can have a diameter of between 1 and 2 inches, such as approximately 1.2 inches. Bulb anchors can have a variety of shapes. For example, as shown in FIG. 54, the anchor 8901 can have an extended diamond shape. Alternatively, as shown in FIG. 55, the bulb anchor 9001 can have an inverted umbrella shape. The inverted shape would preferentially oppose distal device travel by resisting collapse. The secondary anchor in the duodenal bulb can be used alone or in conjunction with any of the proximal anchors described herein.

Additional Exemplary Embodiments

FIGS. 27A-27D illustrate device alternatives having a shaped proximal portion and a floppy distal portion. The floppy distal portion can provide for less peristalsis to grab onto. The proximal device 20P remains similar in design and construction to those described above in FIG. 15. There is a spine 6250 and coiled end 61. The proximal portion 20P has at its distal end a joint, transition or attachment 6205, depending upon the particular configuration of the device. The proximal portion may take on any of the configurations described herein, such as FIGS. 19, 20, 21 or others. The device portion distal to the transition 6205 is floppy in that it will bend, curve and/or flex according to the bending, curvature or flexure of the surrounding anatomy. The floppy portion of the device includes a spine or central member 6255 extending from the transition point 6205 and ending with terminal end 6261. In some embodiments, the terminal end 6261 can be weighted to help prevent retrograde migration, i.e. to help keep the device from moving back into the stomach.

The device embodiments illustrated in FIGS. 27A-27D are shown with a plurality of flow reduction elements 200. Other configurations are possible including more or fewer flow reduction elements or no flow reduction elements as well as the inclusion of one or more of the capabilities described above for drug delivery, data collection or delivery of other therapies. The length of the floppy distal portion may vary.

Figure 27A:
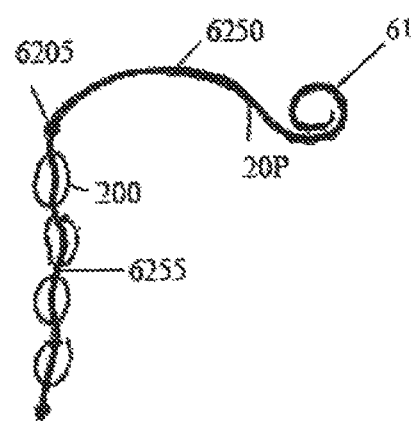
FIGS. 27A-27D show a device having a shaped proximal portion and a floppy distal portion including flow reduction elements along the distal portion (FIG. 27A) having various lengths to place a terminal end in different locations within the duodenum such as the duodenojejunal flexure (FIG. 27B), within the jejunum (FIG. 27C) or within the horizontal or vertical duodenum (FIG. 27D)
Figure 27B:
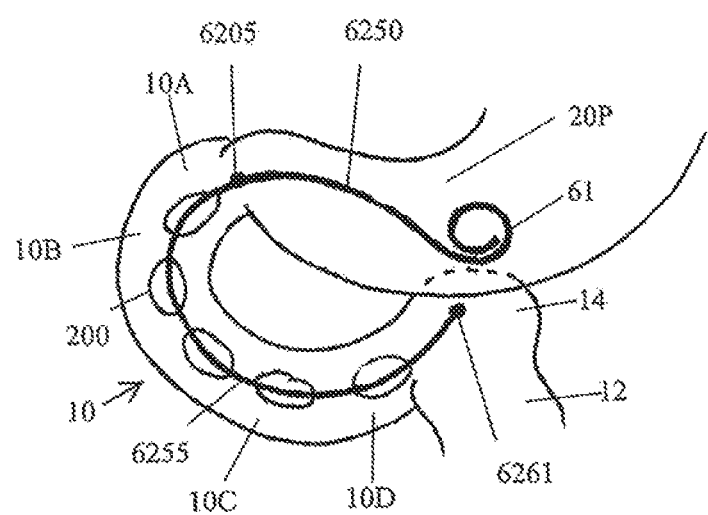

FIG. 27B illustrates the device in place within the anatomy where the length of the floppy distal position places the terminal end 6261 adjacent or nearly so to the proximal end as described and illustrated in FIG. 17. The terminal end 6161 is near the end of the horizontal duodenum 10C or within the junction 14.

Figure 27C:
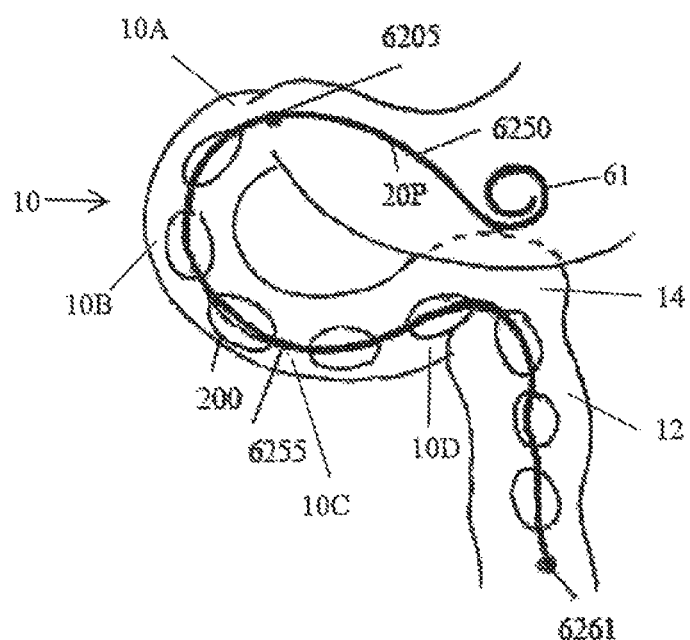

FIG. 27C is an alternative embodiment of the device having a longer distal portion similar to that illustrated and described in FIGS. 76, 22, and 23. In this embodiment, the terminal end 6261 is beyond the flexure 14 and within the jejunum 12 of FIG. 27B with a longer distal length.

Figure 27D:
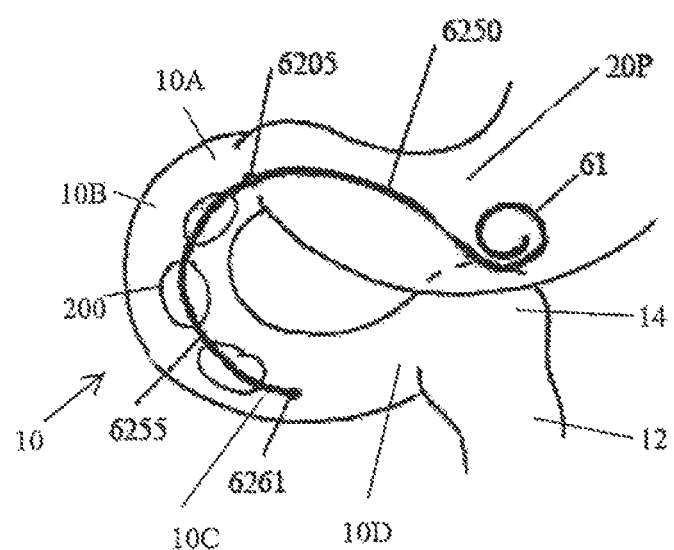

FIG. 27D is an alternative embodiment of the device having a shorted distal portion. In this embodiment, the length of the shaft 6255 places the terminal end 6261 within the descending duodenum 10B or horizontal duodenum 10C.

Figures 28A, 28B:
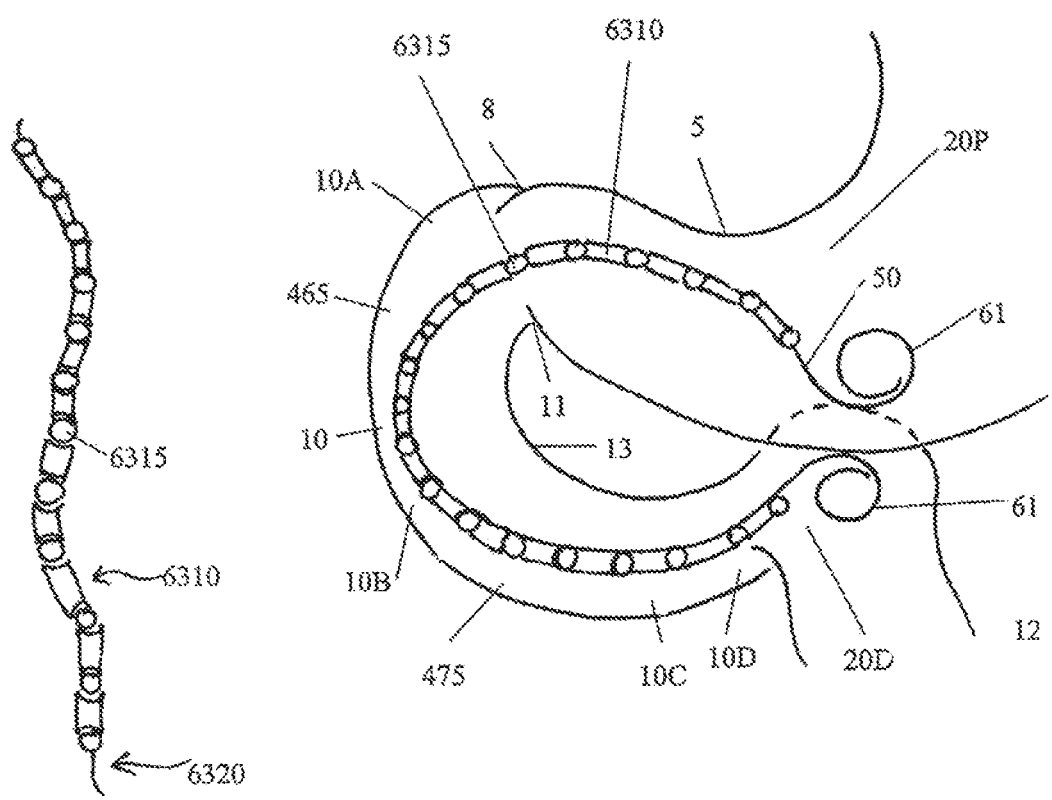
FIGS. 28A-28B show a portion of a device with shape lock features (FIG. 28A) and with engaged shape lock features confirming to the shape of the duodenum (FIG. 28B)
Figure 29:
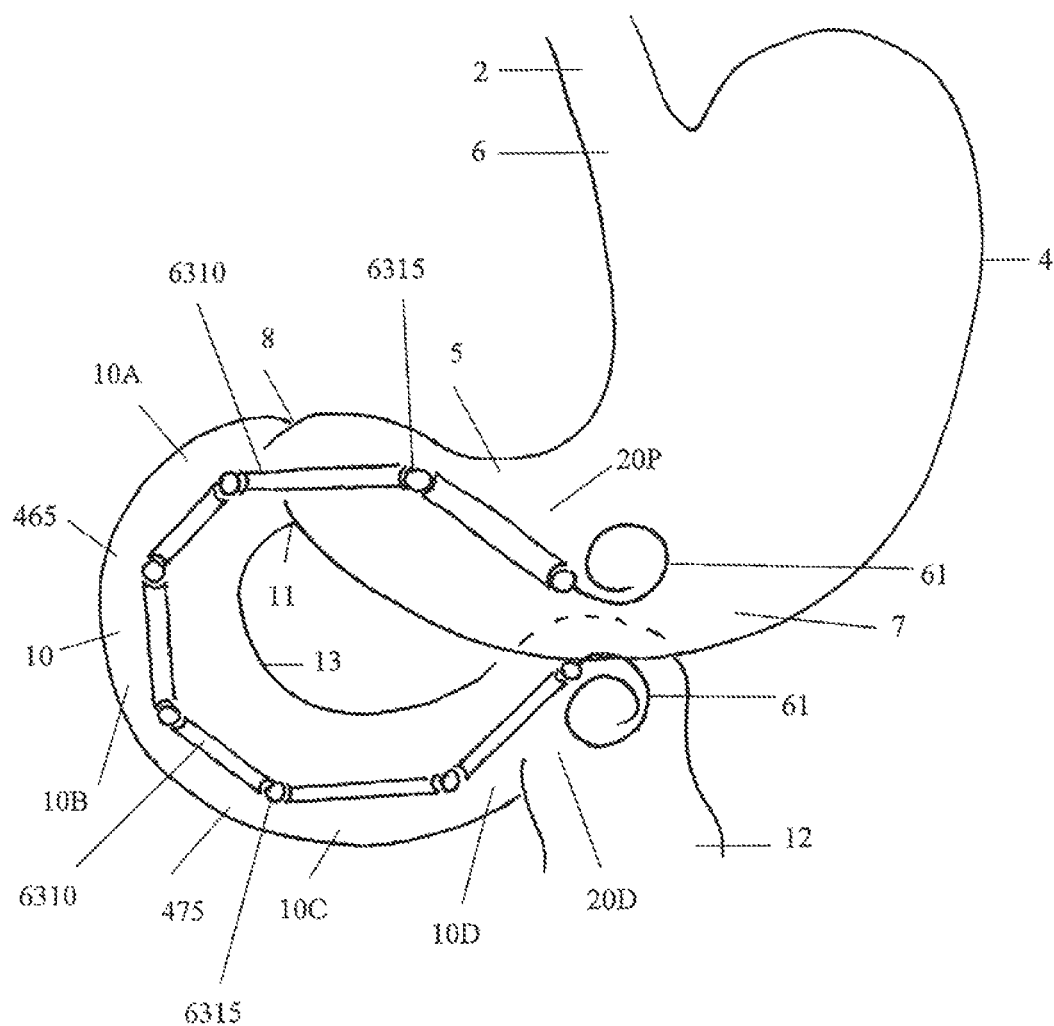
FIG. 29 shows a device within the duodenum having shape lock features with variable sized links and joints in the shape lock portions.

FIGS. 28A, 28B and 29 relate to alternative embodiments of lockable segmented devices or devices configured to be actuated in order to shift between flexible and fixed configurations. The locking segment aspects of FIGS. 28A, 28B and 29 may be modified according to the lockable element designs described in, for example, U.S. Pat. No. 3,546,961 entitled "Variable Flexibility Tether," incorporated herein by reference in its entirety.

FIG. 28A illustrates an unlocked segment of a device having a plurality of links 6310 on either side of joints 6315. The proximal and distal ends are removed for clarity in this view but are illustrated in the full device view of FIG. 28B. Returning to FIG. 28A, the opposing faces of an adjacent link 6310 and joint 6315 may be shafted for cooperative mating. A tensioning member or control cable 6320 extends through the links 6310 and joints 6315. When the cable 6320 is not under tension, adjacent links and joints move freely. Whenever the tensioning cable 6320 is shortened, adjacent links and joints are placed into compression and locked into their orientation. As a result of locking the adjacent links and joints, the overall shape of the device is fixed. In the illustrative embodiments of FIGS. 28A and 28B, the links 6310 are all of the same length and dimension. FIG. 28B illustrates a device having the links and joints of FIG. 28A with proximal and distal coils 61 attached to a spine or central portion 50. The central portion 50 may run through each of the joints and links along with the control cable or the spine 50 may be configured to function as the control cable. Upon delivery in a slack state (i.e., FIG. 28A), the device is permitted to enter into the desired portion of the anatomy until it conforms as desired to the surrounding anatomy. Thereafter, the control cable may be engaged to lock the links and joints into place to hold the device in the desired position. FIG. 28B provides a section view of the distal esophagus, stomach, duodenum & proximal jujunem that illustrates a device in the locked position that conforms to the shape of the stomach and duodenum.

FIG. 29 illustrates an embodiment of a shape locked device of the invention in relation to the esophagus 2, the stomach 4, the duodenum 10, and the jejunum 12. The relevant anatomy is described elsewhere in FIGS. 1, 9 and 13, for example, and similar reference numbers are used here. FIG. 29 is an alternative shape lock device to the one illustrated in FIGS. 28A and 28B. In contrast the shape lock device in FIG. 28A, 28B, the links 6310 in this embodiment may include links of the same or different sizes. In this embodiment, the size and shape of the locking elements need not be uniform. In contrast, the elements may have different shapes or sizes to accommodate the surrounding anatomy for implant. More of fewer links may be used to approximate the shape of the anatomy in the desired implant region. The length of the links 6310 may be selected based upon approximate lengths or fractions thereof of the various portions of the anatomy such as the duodenal bulb, the descending duodenum, the horizontal duodenum, ascending duodenum or the jejunum. In one aspect, the length, dimensions or characteristics of one or more links 6310 in the device may be adjusted or selected based upon the expected location of that link within the anatomy. One or more links may be selected based upon the desired property of the device in that area. In still another alternative embodiment, the locking interaction between the links and the joints may not be the same along the length of the device. In this way, even when locked, some links and joints will remain loose to permit accommodation of adjacent curved anatomy or to relieve pressure points that may develop is the device is too rigid.

One or more of the aspects of the features described in FIG. 28A, 28B or 29 such as a tensioning member 6320, link 6310 or joint 6315 may be added to or included into modified version of the segmented device embodiments described herein. In some embodiments, the spine is segmented into substantially straight segments, that may be adapted to form a basis of a link 6310 design. Some embodiments include a spine with three segments such as, for example, the embodiment illustrated in FIGS. 4 and 9. Still other embodiments include a spine with more than three segments such as, for example, FIG. 3. Still other embodiments include a segment or segments that assume a more curvilinear form such as, for example, the devices shown in FIGS. 44, 46, 47, 48, and 51.

Figure 56A:
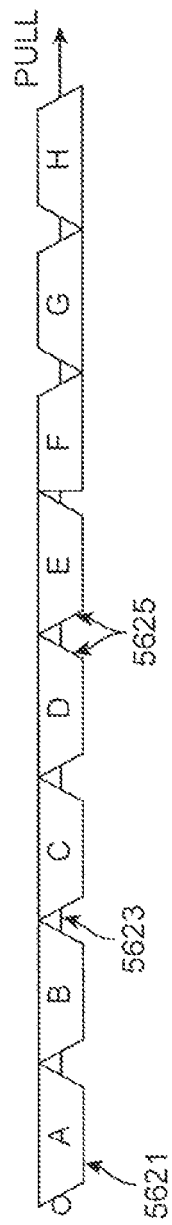
FIGS. 56A-56B show an exemplary shape-locked proximal anchor.
Figure 56B:
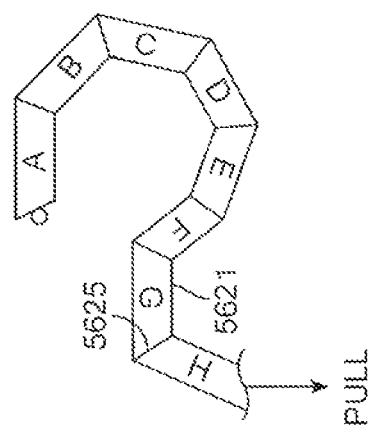
Figure 57A:
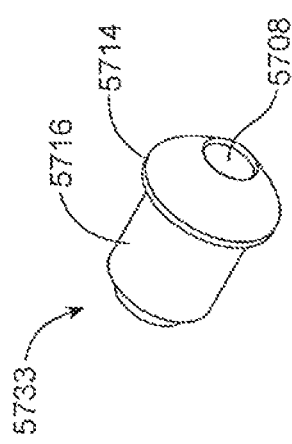
FIGS. 57A-D show an exemplary pusher for use in delivering a collapsible anchor.
Figure 57D:
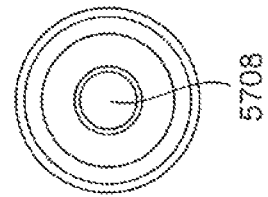
Figure 57C:
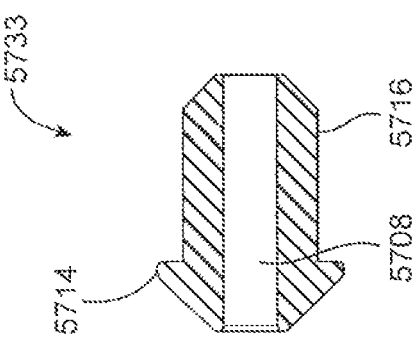
Figure 57B:
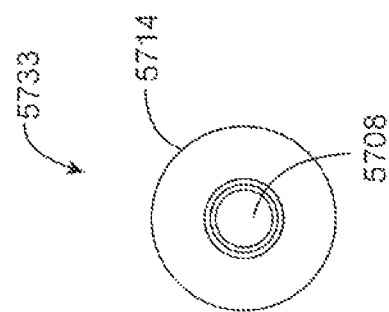
Figure 58A:
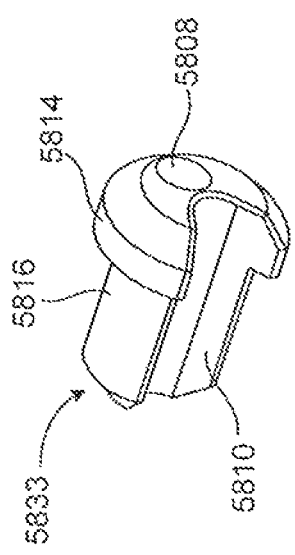
FIGS. 58A-E show another exemplary pusher for use in delivering a collapsible anchor.
Figure 58D:
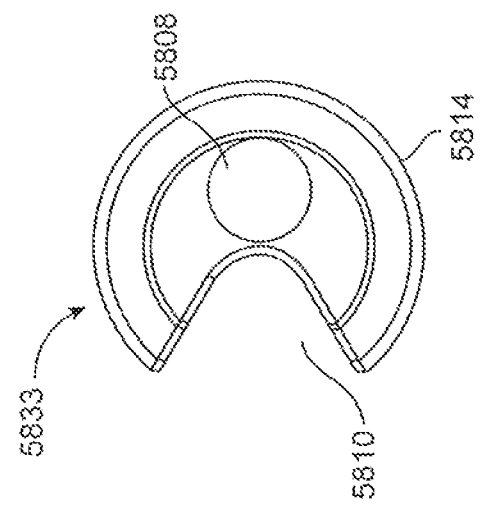
Figure 58C:
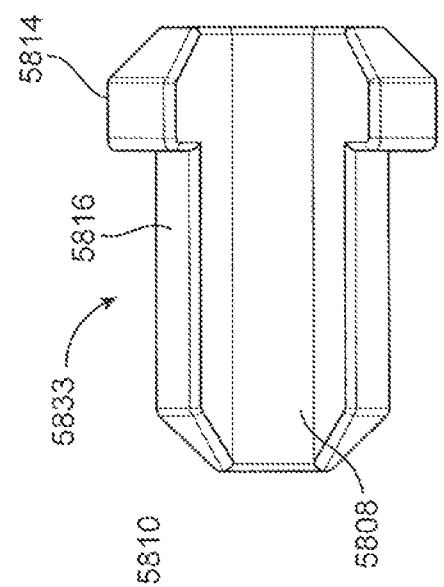
Figure 58B:
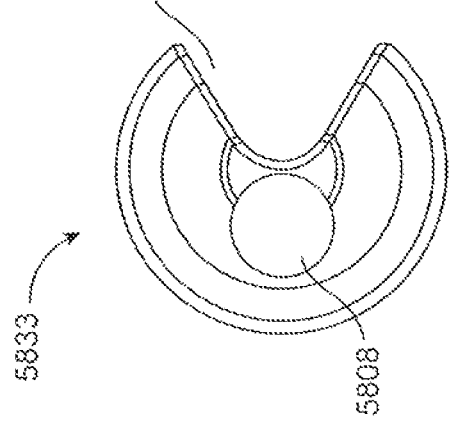
Figure 58E:
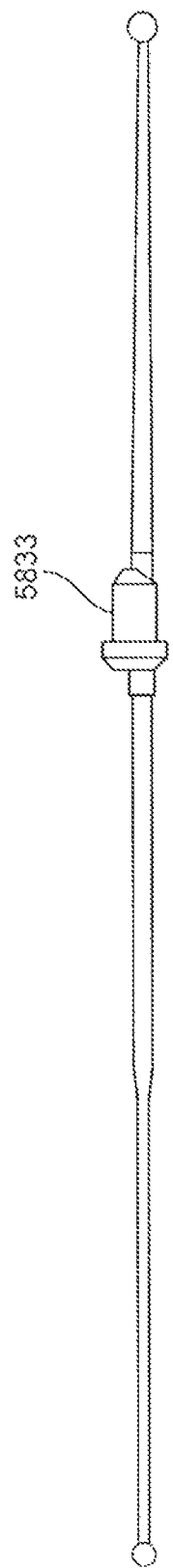

Referring to FIGS. 56A and 56B, the shape-locked configurations can be used to lock an anchor in a desired configuration as well. Thus, for example, the anchor 5601 can begin as a loose set of individuals segments 5621 connected, for example, by a tension cord 5623. The segments 5621 can include angled edges 5625 specifically configured to interact with one another to achieve the desired shape upon locking, as shown in FIG. 56B.

In these and other embodiments, additional alternative configurations and embodiments are possible. In one aspect, one or both of the proximal and distal ends of a device may include the same or different terminating ends. For example, many embodiments illustrate the proximal and distal ends each having a coiled end 61 as shown and described in FIG. 15. The ends may be terminated in a different way however in other embodiments. Any one of the terminal ends described above in, for example, in FIGS. 84A-88 may be used or no terminal end may be provided, such as in FIG. 72, 74 or 76 and others.

In other aspects, the cross sectional shape of the spine or central support may be circular, oval, oblong, rectangular, polygonal, or other shape selected to adjust the ability of the device to conform to the implant location or resist the forces caused by peristaltic action. In still other aspects, the cross section shape of the spine or central support is formed into sections having different shapes comporting to different anatomical implant locations. For example, a terminal end and proximal section that resides in the stomach may have one cross section shape that is different from the central portion and distal end of the same device that resides within the duodenum. Similarly, the cross section shape of the device may vary according to one or more of the portions of the duodenum 10 such as the bulb, descending, horizontal, ascending or even the jejunum or between one or more of the transition areas between these portions.

In many of the illustrative embodiments of the device described herein, the device is illustrated with or described as including a spine 50. It is to be appreciated that the spine 50 may be used with or without flow reduction elements or other capabilities such as those described herein such as for drug delivery, stimulation, flow obstruction, lipid retention or other capabilities as described above. Likewise, in the illustrative embodiments of the device having one or more flow reduction elements, it is to be appreciated that the spine 50 may be used with more or fewer flow reduction elements or without flow reduction elements. Additionally or alternatively, a device may include one or more of the other additional capabilities such as, for example, drug delivery, application of stimulation or modulation signals, flow obstruction through a portion of the alimentary canal where the device is placed, lipid retention or other capabilities described herein. Moreover, while the spine is illustrated in some embodiments as a solid wire, alternative embodiments are possible and within the scope of the invention. In some embodiments, the spine may be a hollow, flexible tube such as illustrated in, for example, FIGS. 3, 4, 5, 7, 9, 10, and 11. In another embodiment, the spine can be a hollow, flexible tube in any of a number of different sizes, shapes or diameters. For example, the spine may be a flexible tube of a larger diameter, such as those found in a duodenal sleeve. In one aspect, the diameter of the spine is about the same size and the internal diameter of a duodenum, a portion of a duodenum or a portion of the alimentary canal where the spine is positioned. In still another embodiment, the spine may be a hollow tube of a smaller diameter such as in a configuration similar to a flexible cord, such as a string. Still further spine alternatives the spine includes any structure attached to an embodiment of an anchor that suspends itself or any other device attached to it intended to remain and/or hang in the duodenum, or portion of an intestine and/or a portion of the alimentary canal. In still further configurations, the spine, hollow tube, flexible cord or string is sized and shaped for placement in the desired therapy location and is formed from any of the materials described herein.

In many of the illustrative embodiments of the device described herein, the device is illustrated having one or more flow reduction elements or other structure to modify the passage of a fluid around or through the device as shown, for example, in FIGS. 3, 4, 5, 6, 9, 10, 11, 15, 17, 18, 22, 27A-27D 35A, 54 and 55. In some embodiments, a device may be illustrated and described with a bare spine such as, for example, in FIGS. 19, 20, 21, 23, 24, 25, 26A, 30A-34C, 45, 47C, and 48B. It is to be appreciated that various illustrative embodiments having a bare spine may be modified to include one or more elements alone or in any combination of the flow modifying elements shown and described in any one or more of FIGS. 3, 4, 5, 6, 9, 10, 11, 15, 17, 18, 22, 27A-27D 35A, 54 and 55.

In many of the illustrative embodiments of the device described herein, the device is illustrated having a particular type of anchor on one end or both ends of the device. In some illustrative embodiments, a portion of a device is shown without any anchoring device. It is to be appreciated that the various device embodiments described herein may be combined in a number of different ways depending upon the requirements of a specific application, therapy or anatomical site for delivery of therapy or anchoring the device. As such, the embodiments shown and described in, for example, FIGS. 3, 4, 5, 6, 7, 9, 10, 11 could be used with one or more of the anchors shown and described in any of FIGS.

15-23, 25A, 25B, 27A-27D or as shown and described in FIGS. 32A-35D, and 45-50. In still other alternative configurations, the proximal portion, anchor or section 20P may be removed, modified or replaced by an anchor embodiment as shown and described, for example, in one or more of FIGS. 32A-35D, and 45-50.

Terms and Conventions

Unless defined otherwise, all technical terms used herein have the same meanings as commonly understood by one of ordinary skill in the art of gastrointestinal interventional technologies. Specific methods, devices, and materials are described in this application, but any methods and materials similar or equivalent to those described herein can be used in the practice of the present invention. While embodiments of the invention have been described in some detail and by way of exemplary illustrations, such illustration is for purposes of clarity of understanding only, and is not intended to be limiting. Still further, it should be understood that the invention is not limited to the embodiments that have been set forth for purposes of exemplification, but is to be defined only by a fair reading of claims that are appended to the patent application, including the full range of equivalency to which each element thereof is entitled.

What is claimed is:

1. An intragastric device comprising:
   an elongated member having a proximal end and a distal end; and
   an anchor connected to the elongated member, the anchor comprising:
   a stem having a proximal end and a distal end, the distal end of the stem attached to the proximal end of the elongated member;
   a first arch and a second arch, each arch having a general U-shape with a first leg and a second leg and a proximal peak therebetween, the first leg of the first arch is connected to the stem and the first leg of the second arch is continuous with, the proximal end of the stem, and the second legs of each arch are located radially away from the stem; and
   a curvilinear element being continuous with the second legs of the first and second arches, wherein the first and second arches, the stem and the curvilinear element are formed as a continuous single wire.

2. The intragastric device of claim 1, wherein the curvilinear element includes at least one coil that loops around and substantially perpendicular to the stem.

3. The intragastric device of claim 2, wherein the coil forms at least one complete loop around the stem.

4. The intragastric device of claim 2, wherein a distance between the second leg of the first arch and the second leg of the second arch is greater than a diameter of the coil.

5. The intragastric device of claim 1, wherein the second leg of the first arch curves in the same clockwise or counterclockwise direction as the second leg of the second arch.

6. The intragastric device of claim 1, wherein the first arch and second arch extend in substantially opposite radial directions.

7. The intragastric device of claim 1, wherein the curvilinear element includes a pull loop extending proximal to the proximal end of the stem and between the first and second arches.

8. The intragastric device of claim 7, wherein the pull loop is configured such that, when the pull loop is moved proximally away from the stem, the curvatures of the first arch and the second arch are reduced.

9. The intragastric device of claim 1, wherein the curvilinear element is substantially in a plane that is substantially perpendicular to the first and second arches.

10. The intragastric device of claim 9, wherein the curvilinear element comprises a first counterarch and a second counterarch, the first counterarch being continuous with the second leg of the first arch and the second counterarch being continuous with the second leg of the second arch, and the first counterarch being continuous with the second counterarch.

11. The intragastric device of claim 1, wherein, in use within a gastrointestinal tract, a diameter of the anchor is larger than an opening through which the elongated member passes.

12. The intragastric device of claim 11, wherein the opening is a pylorus.

13. The intragastric device of claim 1, wherein the arches and curvilinear element are configured to be unwound to form a straightened anchor for delivery or removal of the anchor from the gastrointestinal tract.

14. The intragastric device of claim 13, wherein the straightened anchor comprises two substantially parallel and straight wires for delivery or removal.

15. The intragastric device of claim 1, further comprising a fastening element configured to fasten at least one portion of the anchor to another portion of the anchor to hold the shape of the anchor during use in the gastrointestinal tract.

16. The intragastric device of claim 1, wherein the first arch, the second arch, and the curvilinear element form a figure 8 shape.

* * * * *